United States Patent [19]
Storkus et al.

[11] Patent Number: 6,077,519
[45] Date of Patent: Jun. 20, 2000

[54] METHODS FOR ISOLATION AND USE OF T CELL EPITOPES ELUTED FROM VIABLE CELLS IN VACCINES FOR TREATING CANCER PATIENTS

[75] Inventors: Walter J. Storkus, Glenshaw; Michael T. Lotze, Pittsburgh, both of Pa.

[73] Assignee: University of Pittsburgh, Pittsburgh, Pa.

[21] Appl. No.: 08/785,831

[22] Filed: Jan. 15, 1997

Related U.S. Application Data

[63] Continuation-in-part of application No. 08/474,120, Jun. 7, 1995, which is a continuation-in-part of application No. 08/011,007, Jan. 29, 1993, abandoned.

[51] Int. Cl.⁷ .......................... A61K 35/12; A61K 38/00; C12N 15/85; C07K 5/00
[52] U.S. Cl. .................. 424/277.1; 424/85.1; 424/93.71; 435/70.1; 435/70.3; 435/325; 435/372; 435/384; 435/385; 435/386; 514/2; 514/21; 530/344
[58] Field of Search ................................ 424/277.1, 85.1, 424/93.71; 435/70.1, 70.3, 325, 372, 384, 385, 386; 514/2, 21; 530/344

[56] References Cited

PUBLICATIONS

Zinkernagel, R.M., et al., *Adv. Immunol.* 27:51 (1979).
Doherty, P.C., et al., *Adv. Cancer Res.* 42:1 (1984).
Zinkernagel, R.M., et al., *Nature* 248:701 (1974).
Townsend, A., el al., *Cell* 42:457 (1985).
Townsend, A., et al., *Cell* 44:959 (1986).
Yewdell, J.W., et al., *Scince* 244:1072 (1989).
Townsend, A., et al., *Cell* 62:285 (1990).
Nuchtern, J.G., et al., *Nature* 339:223 (1989).
Rotzschke, O., et al., *Nature* 348:252 (1990).
Van Bleek, G.M., et al., *Nature* 348:213 (1990).
Rotzschke, O., et al., *Science* 249:283 (1990).
Falk, K., et al., *Nature* 348:248 (1990).
Jardetsky, T.S., et al., *Nature* 351:326 (1991).
Falk, K., et al., *Nature* 351:290 (1991).
Nikolic–Zugic, J., et al., *Immunol, Rev.* 10:54 (1991).
Kornstein, M.J., et al., *Cancer Res.* 43:2749 (1983).
Van Duinen, S.G., et al., *Cancer Res.* 48:1019 (1988).
Lotze, M.T., *Pigment Cell* 10:163 (1990).
Rosenberg, S.A., et al., *N. Eng. J. Med.* 319:1676 (1988).
Parmiani, G., et al., *J. Natl. Cancer Inst.* 82:361 (1990).
Van den Eynde, B., et al., *Int. J. Cancer* 44:634 (1984).
Anichini, A., et al., *J. Immunol.* 142: 3692 (1989).
Wolfel, T., et al., *Eur. J. Immunol.* 24:759 (1994).
Crowley, N.J., et al., *J. Immunol.* 146:1692 (1991).
Traversari, C., et al., *J. Exp. Med.* 176:1453 (1991).
Kawakani, Y., et al., *J. Exp. Med.* 180:347 (1994).
Hom, S.S., et al., *J. Immunother.* 10:153 (1991).
Huang, A.Y.C., et al., *Science* Wash., D.C. 264:961 (1994).
Becker, Y., *In Vivo* 7:187 (1993).
Steinmen, R.M., et al., *J. Exp. Med.* 137:1142 (1973).
Levin, D., et al., *J. Immunol.* 151:6742 (1993).
Constant, S., et al., *J. Immunol.* 154:4915 (1995).
Cohen, P.J., et al., *Eur. J. Immunol.* 24:315 (1994).
Porgador, A., et al., *J. Exp. Med.* 182:255 (1995).
Takahashi, H.Y., et al., *Int. Immunol.* 5:849 (1993).
Flamand, V., et al., *Eur. J. Immunol.* 24:605 (1996).
Mayordomo, J.I., et al., *Nature Med.* 1:1297 (1995).
Celuzzi, C.M., et al., *J. Exp. Med.* 183:283 (1996).
Storkus, J.W., et al., *Biologic Therapy of Cancer* 2nd ed DeVita, V.T. ed., J.B. Lippencott Co., Phila. 66–77 (1995).
McMichael, A.J., et al., *Eur. J. Immunol.* 8:705 (1978).
Suguwara, S., et al., *J. Immunol Meth.* 100:83 (1987).
Gillet, A.C., et al., *Eur J. Immunol.* 20:759 (1990).
Biddison, W.E., et al., *J. Immunol.* 129:730 (1982).
Mitchell, M.S., et al., *J. Clin. Oncol.* 10:1158 (1992).
Gorga, J.C., et al., *Crit Rev. Immunol.* 11:305 (1992).
Storkus, W.J., et al., *Proc. Nat. Acad. Sci. USA* 88:5989 (1991).
Storkus, W.J., et al., *Proc. Nat. Acad. Sci. USA* 86:2361 (1989).
Carbone, F.R., et al., *J. Exp. Med.* 167:1767 (1988).
Kawakami, Y., et al., *J. Immunol.* 148:638 (1992).
Storkus, W.J., et al., *J. Immunol.* 143:3853 (1989).
Wolfel, T., et al., *Immunogenet.* 26:178 (1987).
Anichini, A., et al., *J. Exp. Med.* 177:989 (1993).
Whiteside, T.L., et al., *J. Immunol. Methods* 90:221 (1981).
McMichael, A.J., et al., *Hum. Immunol.* 1:121 (1980).
Zeh, H.J., et al., *Hum. Immunol* 39:79 (1994).
Salter, R.D., et al., *Immunogenetics* 21:235 (1985).
Cox, A.L., et al., *Science* Wash., DC 264:716 (1994).
Culmann, B.E., et al., *Eur. J. Immunol.* 19:2383 (1989).
Kawakami, Y., et al., *Proc. Nat. Acad Sci USA* 91:3515 (1994).
Nijman, H.W., et al., *Eur. J. Immunol.* 23:1215 (1993).
Boyd, L.F., et al., *Proc. Nat. Acad Sci USA* 89:2242 (1992).
Bodmer, H.G., et al., *Nature (Land.)* 342:443 (1989).
Wolfel, T., et al., *Eur. J. Immnunol.* 24:759 (1994).
Nanni, P., et al., *Clin Exp. Metastis.* 1:373 (1983).
Frassanito, M.A., et al., *Cancer Res.* 55:124 (1995).
Linsley, P.S., et al., *Science* Wash., DC 257:792 (1992).
Sheehan, K.C.F. et al., *J. Immunol.* 142:3884 (1989).
Finkelman F.D. et al., *P.N.A.S. USA* 83:9675 (1986).
Wilde, D.B., et al., *J. Immunol.* 131:2178 (1978).
Sarmiento, M., et al., *J. Immunol.* 125:2665 (1980).
Macatonia, S.E., et al., *J. Immunol.* 154: 5071 (1995).
Zitvogel, L., et al., *Eur. J. Immunol.* 26:1335 (1996).
Kennedy, M.K., et al., *Eur. J. Immunol.* 24:2271 (1994).
Storkus, W.J., et al., *J. Immunol.* 151:3719 (1993).
Jung, T., et al., *J. Immunol. Meth.* 159:197 (1993).

*Primary Examiner*—Sheela Huff
*Assistant Examiner*—Geetha P. Bansal
*Attorney, Agent, or Firm*—Reed Smith Shaw & McClay LLP

[57] ABSTRACT

Methods are provided for eluting peptides that are bound to major histocompatibility complex ("MHC") molecules expressed on the cell surfaces of viable cells that have at least one MHC-peptide complex on the surfaces of the cells. Methods are provided for using such acid-eluted T cell epitopes, preferably obtained from a patient's tumor, and autologous dendritic cells as the basis for antitumor vaccines.

24 Claims, 28 Drawing Sheets

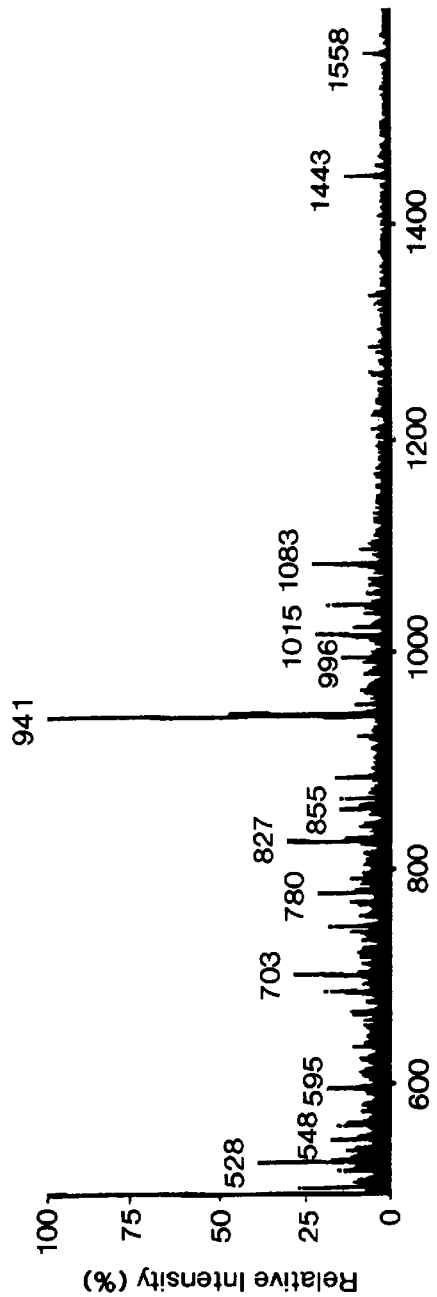
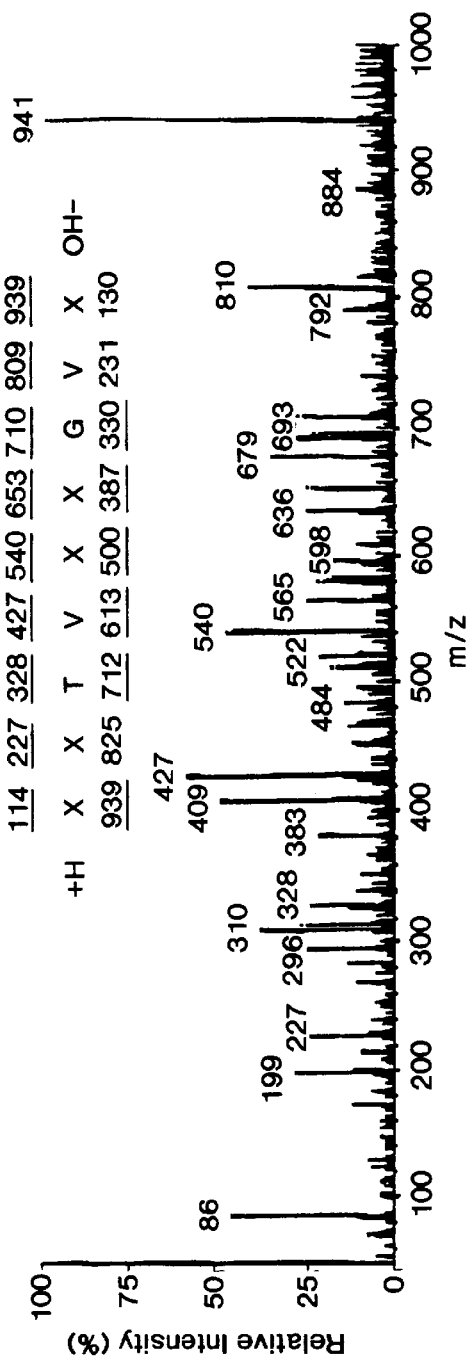
FIG. 10A
FIG. 10B

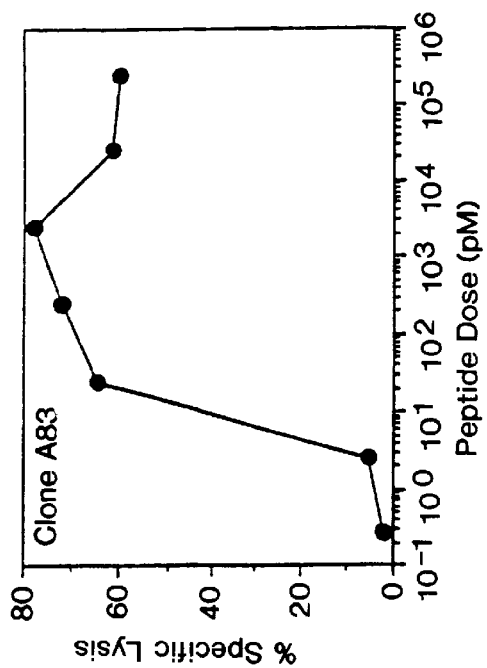
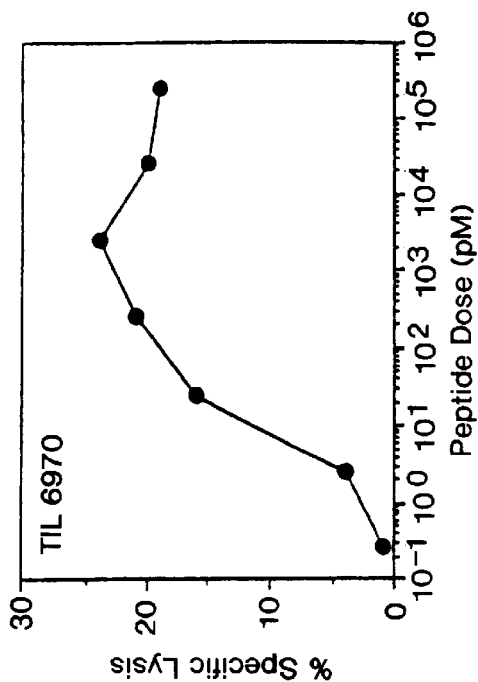
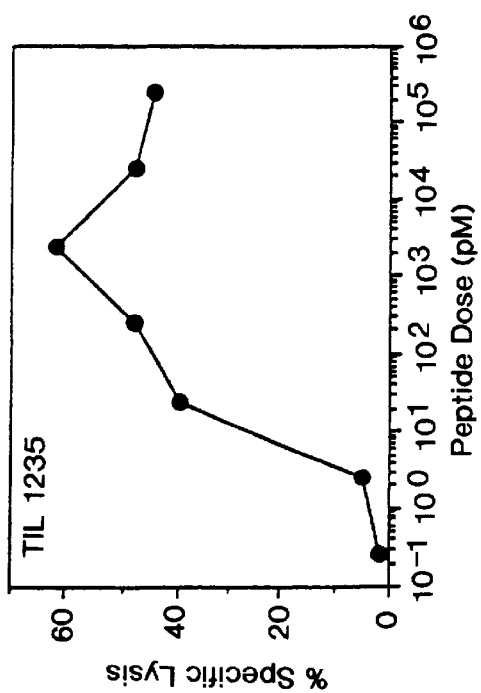
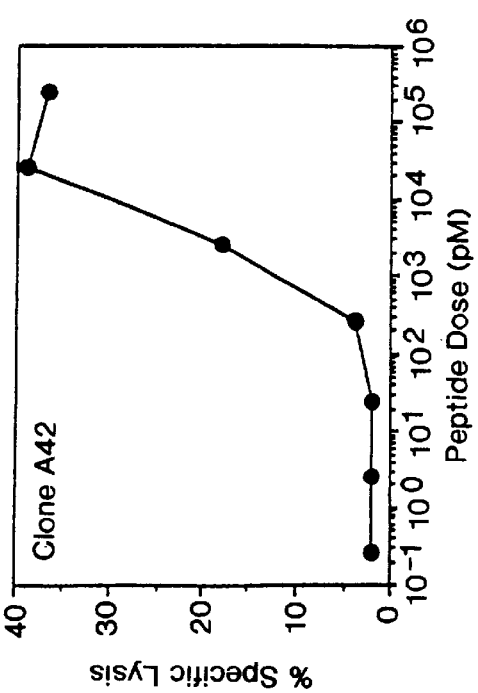

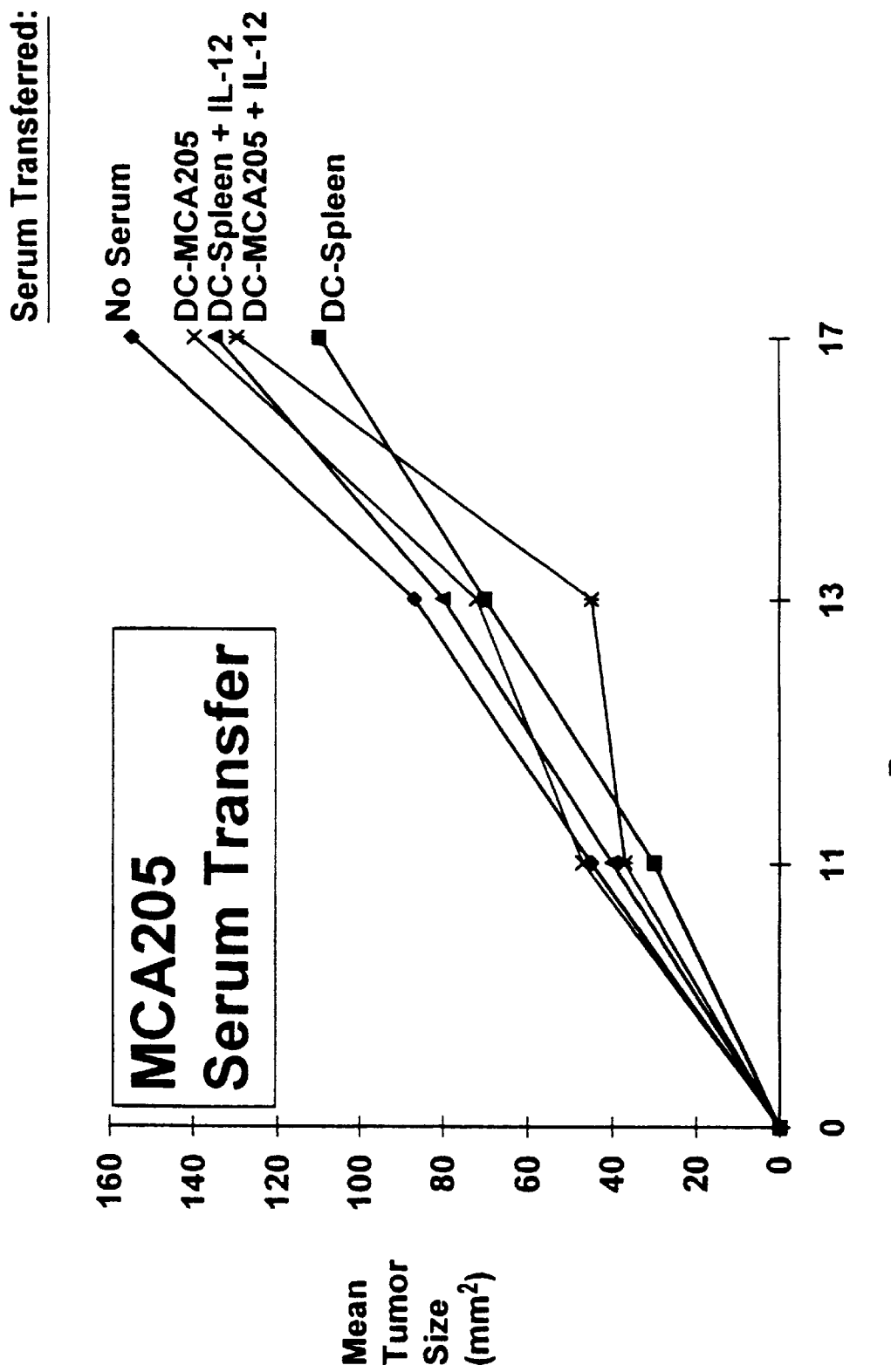

"Normal" HLA-A2+ Responders:

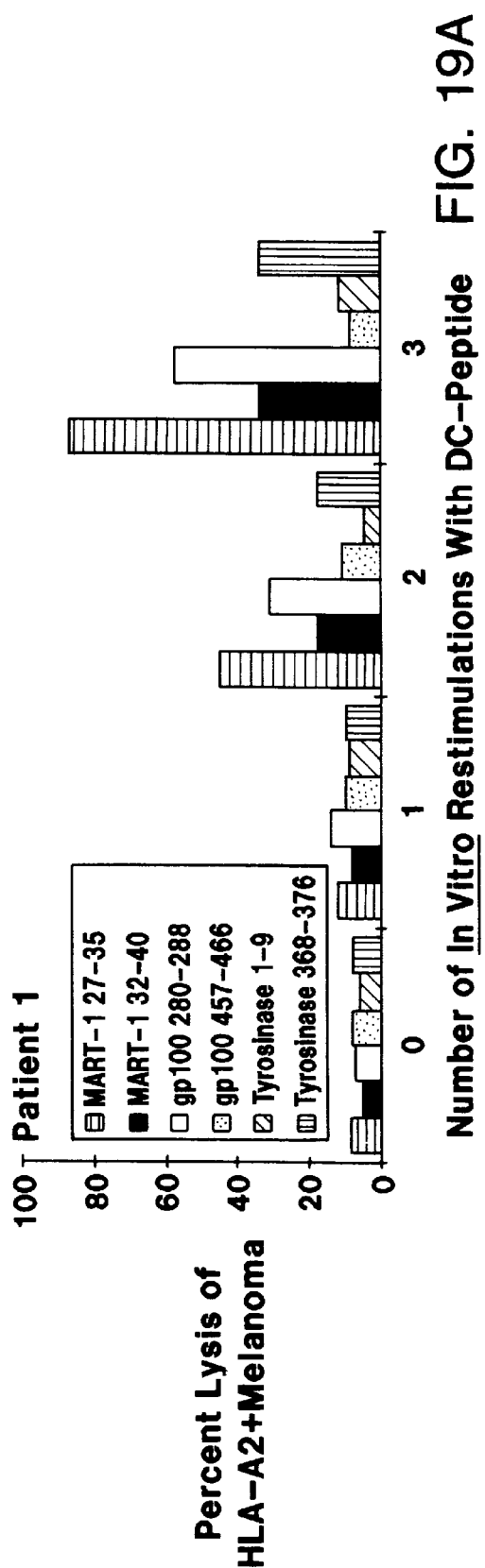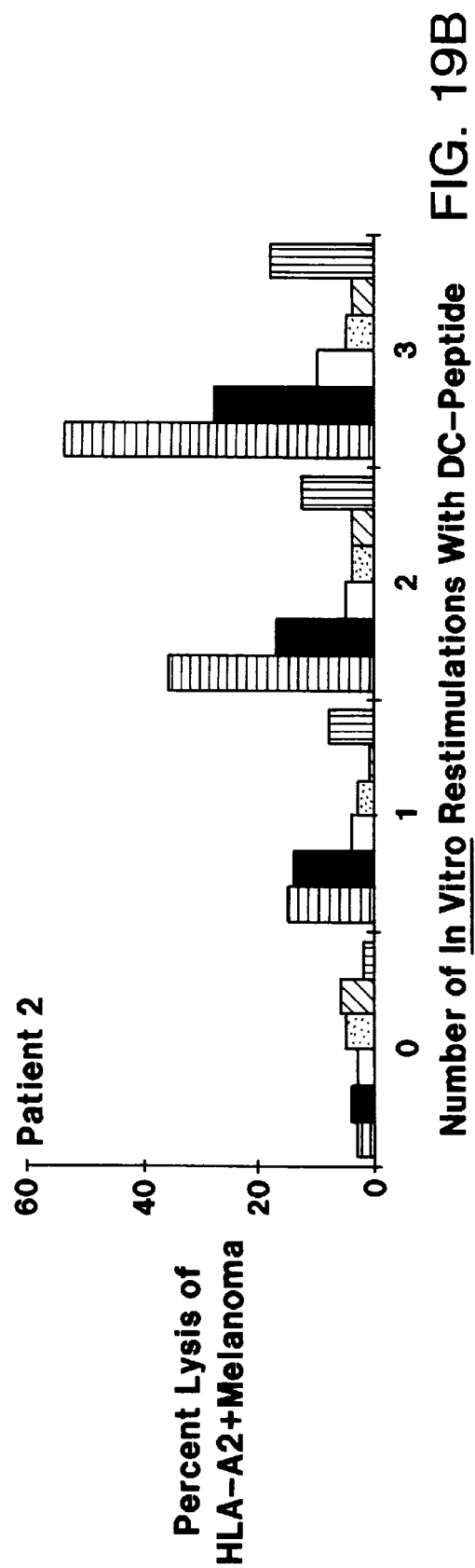
FIG. 19A
FIG. 19B

METHODS FOR ISOLATION AND USE OF T CELL EPITOPES ELUTED FROM VIABLE CELLS IN VACCINES FOR TREATING CANCER PATIENTS

This is a continuation-in-part of application(s) Ser. No. 08/474,120 filed on Jun. 7, 1995, which in turn is a continuation-in-part of Ser. No. 08/011,007 filed on Jan. 29, 1993 (now abandoned).

The present invention was developed in part with government support under grant numbers CA-57840 and POI-CA-59371 awarded by the National Institutes of Health. The government has certain rights in this invention.

FIELD OF THE INVENTION

The present invention relates generally to the elution of certain, preferably, immunogenic peptides and more particularly relates to the isolation of peptides associated with major histocompatibility complexes that are expressed at the cell surface of viable cells. Peptides eluted according to the invention may find use in the development of viral or tumor vaccines, or alternatively, as a means to treat autoimmune diseases. In particular, a naturally processed melanoma peptide recognized by CD8$^+$ cytotoxic T lymphocytes has been identified according to the present invention. The present invention further relates to use of autologous dendritic cells pulsed with acid-eluted peptides derived from autologous tumors as a vaccine for treatment for both well defined tumors such as melanoma and for tumors expressing as yet uncharacterized epitopes.

BACKGROUND OF THE INVENTION

T lymphocyte ("T cell") antigen receptors ("TCR") recognize endogenously processed fragments of antigens that are presented to T cells in association with major histocompatibility complex ("MHC") class I or class II molecules.

An individual's T cells recognize and are activated by protein antigens only if a fragment of the antigen is properly presented on the surface of a target cell. The antigen presentation process that allows an antigen to be recognized by a T cell requires that the antigen be associated with either (MHC) class I histocompatibility molecules for presentation to cytotoxic T lymphocytes ("CTLs") or class II histocompatibility molecules for presentation to helper T cells. Other T cell subsets such as γ/δ (gamma-delta) T cells (CD4$^-$, CD8$^-$) may recognize alternate "peptide presenting" molecules not encoded in the MHC, such as CD1, etc. The subset of T cells denoted CD8$^+$ recognize antigenic determinants/epitopes that are associated with class I histocompatability molecules. The other subset of T cells, CD4$^+$ cells, recognize antigenic determinants/epitopes that are associated with class II histocompatibility molecules. The antigenic determinants/epitopes that are presented on the surface of cells in association with MHC molecules are also known as T cell epitopes.

The study of CD8$^+$ T cell recognition of target cells has been extensive since the early 1970's when Zinkernagel and Doherty demonstrated that CTL recognition of viral-infected autologous target cells requires the presence of self class I MHC molecules. Thus such recognition of target cells by CD8$^+$ T cells is referred to as being MHC class I-restricted. Zinkernagel, R. M., et al., *Adv. Immunol.* 27:51 (1979); Doherty, P. C., et al., *Adv. Cancer Res.* 42:1 (1984); and Zinkernagel, R. M., et al., *Nature* 248:701 (1974), the disclosures of which are incorporated herein by reference. It was later shown that virus-specificity of CTL's is directed against viral protein-derived peptide sequences that are presented by infected cell MHC class I molecules to CD8$^+$ T cells. See, for example, Townsend, A., et al., *Cell* 42:457 (1985) and Townsend, A., et al., *Cell* 44:959 (1986), the disclosures of which are incorporated herein by reference.

As noted above, it is not the entire antigen that is presented by target cells and recognized by CD8$^+$ cells, but rather what is presented and recognized are small endogenously processed peptides that are generated from antigens by intracellular degradation pathways in either the cytosol or the endoplasmic reticulum ("ER") of the target cell. Such processed peptides bind to newly synthesized class I heavy chain-$\beta_2$-microglobulin heterodimers in the ER. See, for example, Yewdell, J. W., et al., *Science* 244:1072 (1989); Townsend, A., et al., *Cell* 62:285 (1990); and Nuchtern, J. G., et al., *Nature* 339:223 (1989), the disclosures of which are incorporated herein by reference. The processed peptide is bound to the class I heavy chain-light chain dimer molecule via the class I antigen binding site/peptide cleft. The complex thereby generated is a transport competent trimer as reported by Yewdell, J. W., et al., *Science* 244:1072 (1989); Townsend, A., et al., *Cell* 62:285 (1990); and Nuchtern, J. G., et al., *Nature* 339:223 (1989). This class I histocompatibility molecule-processed peptide complex is then expressed on the surface of the target cell where it may be ultimately recognized by T cell clonotypic receptors on CD8$^+$ cells in conjunction with CD8 accessory molecules. See, Rotzschke, O., et al., *Nature* 348:252 (1990); Van Bleek, G. M., et al., *Nature* 348:213 (1990); Rotzschke, O., et al., *Science* 249:283 (1990); and Falk, K., et al., *Nature* 348:248 (1990), the disclosures of which are incorporated herein by reference.

Recently, peptides have been isolated from the antigen binding sites of human and murine class I and class II molecules and directly sequenced. Two principal methods have been used to isolate such peptides. In one of the two methods total cellular extraction of such peptides is carried out in pH 2.0 trifluoroacetic acid ("TFA"). This method results in cell cytolysis and release of total cytosolic peptides, only a fraction of which are actually class I-related. This method also typically employs protease inhibitors since cell cytolysis results in the release of proteolytic enzymes that can alter or destroy peptides of potential interest. See, Rotzschke, O., et al., *Nature* 348:252 (1990), and Falk, K., et al., *Nature* 348:248 (1990), the disclosures of which are incorporated herein by reference. The second isolation method entails acid denaturation of immunoaffinity purified class I-peptide complexes. By contrast with the first method, the second method of peptide isolation is highly class I selective, and even class I allele specific since monoclonal antibodies directed against individual class I allotypes can be used to immunopurify class I complexes. By this latter approach, the majority of known class I-bound peptide sequence data has been acquired. See, for example, Van Bleek, G. M., et al., *Nature* 348:213 (1990); Rotzschke, O., et al., *Science* 249:283 (1990); Madden, D. R., et al., *Nature* 353:326 (1991); Jardetzky, T. S., et al., *Nature* 351:290 (1991); and Nikolic-Zugic, J., et al., *Immunol Rev.* 10:54 (1991), the disclosures of which are incorporated herein by reference.

The main drawback of these two methods is that since both require cell cytolysis, a large number of starting cells ($10^9$–$10^{11}$) are required from which peptides are extracted after cellular cytolysis in order to obtain sequence grade quantities (approximately 1 pM) of specific peptide. Therefore the application of such techniques are limited to cell types which readily adapt to in vitro cell culture and which proliferate sufficiently well to allow such high cellular yields.

Methods of isolating class I peptide complexes are additionally relevant because CD8$^+$ lymphocytes have emerged as being potentially useful in the development of anti-tumor vaccines, which vaccines will ideally provoke anti-tumor immune responses in individuals. To that end, tumor infiltrating lymphocytes (TILs) have been found to be important agents in the generation of cellular immunity through their identification in spontaneously regressing lesions in some patients as reported by Kornstein, M. J., et al. *Cancer Res.* 43:2749 (1983), the disclosure of which is incorporated herein by reference. TILs are also frequently found in non-regressing lesions and when present in high numbers are correlated with a better clinical prognosis. Van Duinen, S. G., et al., *Cancer Res.* 48:1019 (1988), the disclosure of which is incorporated herein by reference. Numerous studies have shown that such TILs display potent anti-melanoma cytolytic activity when they are cultured in vitro with interleukin-2. See, for example, Lotze, M. T., *Pigment Cell* 10:163 (1990), and Rosenberg, S. A., et al., *N. Eng. J. Med.* 319:1676 (1988). Anti-melanoma cytolytic activity is typically associated with CD8$^+$ TIL subpopulations which recognize tumor cells in a class I—restricted manner. The HLA class I antigen, HLA-A2, appears to represent the most common class I restriction element for human melanoma TIL, however, other HLA class I antigens such as HLA-A1, -A10, -A24, -A31, -B44, -B50, and -CW7 have also been identified. The identification of such restriction elements may be important in the development of effective melanoma vaccines.

During the last several years, a number of further studies have been conducted on the autologous CD8$^+$ T cell-mediated response to human melanoma. See, for example, Parmiani, G., et al., *J. Natl. Cancer Inst.* 82:361 (1990) and Van den Eynde, B., et al., *Int. J. Cancer* 44:634 (1984), the disclosures of which are incorporated herein by reference. The emerging picture indicates that melanomas express multiple T cell epitopes, some of which are unique to a given tumor, while others are shared by allogeneic, HLA-matched melanomas. See, for example, Anichini, A., et al., *J. Immunol* 142:3692 (1989); Wolfel, T., et al., *Eur. J. Immunol.* 24:759 (1994); and Crowley, N. J., et al., *J. Immunol.* 146:1692 (1991), the disclosures of which are incorporated herein by reference. These epitopes appear to represent short 9–10 amino acid peptides derived from tumor-associated antigens that are presented by MHC class I antigens to CD8$^+$ T cells. See, for example, Traversari, C., et al., *J. Exp. Med.* 176:1453 (1991) and Kawakami, Y., et al., *J. Exp. Med.* 180:347 (1994), the disclosures of which are incorporated herein by reference. While many class I alleles have been reported to represent restriction elements for tumor-reactive CD8$^+$ T cells, as reported by Hom, S. S., et al., *J. Immunother.* 10:153 (1991), the disclosure of which is incorporated herein by reference, the HLA-A2.1 allele, which is expressed by 45% of melanoma patients, appears to play an immunodominant role in presenting melanoma epitopes as reported by Crowley, N. J., et al., *J. Immunol.* 146:1692 (1991). As will be shown herein, at least six different CD8$^+$ T cell-defined epitopes appear to be expressed by multiple HLA-A2$^+$ melanomas. The identification and sequencing of these individual epitopes should allow for the design and testing of peptide-based immunotherapies for the treatment of melanoma.

Presentation of MHC class I-restricted tumor antigens to CD8$^+$ T lymphocytes was classically assumed to be presented by the cell naturally expressing the antigens, such as the tumor cell itself. However, recent studies suggest that tumor cells are poor antigen presenting cells, and "professional" antigen presenting cells may be essential for induction of not only CD4$^+$ T cells but also for a CD8$^+$ T cell-mediated antitumor response. Huang, A. Y. C., et al., *Science (Wash. DC)* 264:961 (1994), the disclosure of which is incorporated herein by reference, reported that the in vivo priming of MHC class I-restricted responses involves a transfer of tumor antigens to a host bone marrow-derived dendritic cell ("IBM-DC") and subsequent presentation to CD8$^+$ T cell effectors. A correlation between the number of presumptive dedritic cells ("DC") infiltrating a cancer and longer patient survival or reduced frequency of metastatic disease have been observed for a variety of cancer types. See, Becker, Y., *Vivo* 7:187 (1993), the disclosure of which is incorporated herein by reference. DC were first described by Steinman, R. M., et al., *J. Exp. Med.* 137:1142 (1973), the disclosure of which is incorporated herein by reference, and are known to be highly specialized antigen-presenting cells and to be the principal activators of resting, naive T cells in vitro and in vivo. DC are further capable of efficiently transporting antigens from the periphery to lymphoid organs. See, Levin, D., et. al., *J. Immunol* 151:6742 (1993); Constant, S., et al., *J. Immunol* 154:4915 (1995); and Cohen, P. J., et al., *Eur. J. Immunol* 24:315 (1994), the disclosures of which are incorporated herein by reference. DC pulsed with ovalbumin or viral peptides, lymphoma-derived surface Ig, or tumor-derived synthetic epitopes and then injected as a vaccine have been shown to immunize naive animals against a subsequent viral or tumor challenge. See, Porgador, A., et al., *J. Exp. Med.* 182:255 (1995); Takahashi, H. Y., et al., *Int. Immunol.* 5:849 (1993); Flamand, V., et al., *Eur. J. Immunol* 24:605 (1994); Mayordomo, J. I., et al., *Nature Med.* 1:1297 (1995); and Celuzzi, C. M., et al., *J. Exp. Med.* 183:283 (1996), the disclosures of which are incorporated herein by reference.

Development of antitumor vaccines based on MHC-presented tumor peptide epitopes capable of being recognized by T cells is limited due to the fact that defined tumor-derived T cell epitopes are currently available for study in only a limited number of human tumor types (i.e., melanoma, ovarian, and breast carcinoma) as reported by Storkus, W. J., et al., *Biologic Therapy of Cancer* 2nd ed. DeVita, V. T., et al., editors. J. B. Lippincott Co., Philadelphia, Pa. 66–77 (1995), the disclosure of which is incorporated herein by reference. Additionally, the vast majority of the histologic subtypes of cancers express as yet undefined shared tumor epitopes and individual patients may also express idiotypic determinants unique to that patient.

It is also difficult to extend the range of the search for biologically relevant allo-, viral-, and tumor-specific T cell epitopes to cell types that adapt poorly to tissue culture or which proliferate slowly in vitro. Accordingly there is a need for methods that will remove T cell epitopes from a greater range of cell types. In doing so, the development of peptide-based immunotherapies for the treatment of patients with melanoma and other diseases may be furthered. In particular, there is a need for methods to develop protocols to treat cancer patients whose tumors express as yet uncharacterized T cell epitopes.

SUMMARY OF THE INVENTION

Accordingly, it is a primary object of the present invention to provide a method of eluting MHC-bound peptides from the cell surface of viable cells that is non-toxic to the cells so that the cells can regenerate their MHC-peptide complexes.

Another object of the present invention is to provide a method of obtaining MHC-bound peptides that have a low affinity for MHC molecules.

Another object of the present invention is to provide a rapid method of removing MHC-bound peptides from viable cells.

Yet another object of the present invention is to provide a method of isolating MHC bound peptides from cells which are difficult to culture or propagate.

Still another object of the present invention is to provide a method of deriving multiple cell equivalents of MHC-bound peptides from a single cell.

Still yet another object of the present invention is to biochemically identify and characterize endogenously processed peptides presented by HLA-A2+ melanomas that are recognized by class I-restricted, melanoma-specific CD8+ T cells.

Another object of the present invention is to generate sufficient quantities of peptides eluted from MHC complexes for mass spectrometric sequencing and subsequent synthesis for vaccine development.

Another object of the present invention is to biochemically identify acid-eluted tumor derived peptides.

Yet another object of the present invention is to provide a method for treating cancer patients whose tumors express MHC class I-presented T cell epitopes.

Another object of the present invention is to provide a method for treating cancer patients whose tumors express uncharacterized MHC class I-presented T cell epitopes.

Still yet another object of the present invention is to provide autologous dendritic cell and acid stripped peptide-based vaccines for treatment of cancer patients.

Another object of the present invention is to provide vaccines for treatment of a cancer patient whose tumors express uncharacterized T cell epitopes based on allogeneic MHC class I-eluted tumor peptides pulsed onto autologous bone marrow- or peripheral blood-derived dendritic cells.

These and other objects of the present invention are achieved by one or more of the following embodiments.

In one aspect, the invention features a method of eluting peptides that are bound to major histocompatibility complex ("MHC") molecules expressed on the cell surfaces of viable cells that have at least one MHC-peptide complex presented on the surfaces of said cells, said method comprising:

incubating said cells in the presence of peptide elution buffer, and recovering said peptides from said peptide elution buffer.

In another aspect, the invention features a method of eluting increased amounts of MHC-associated peptides from one or more viable cells in culture that have expressed on their surfaces at least one MHC-peptide complex, comprising:

a. incubating said cells in the presence of peptide elution buffer at a pH in the range of about 2.7 to about 5.0 to elute said MHC-associated peptides from said cells;

b. harvesting the buffer eluate peptide-containing solution from step a);

c. neutralizing the acid remaining on said cell from said incubation;

d. reculturing said cell until such time that said cells have regenerated their MHC-peptide complexes; and e. repeating steps a-d one or more times to obtain additional amounts of MHC-associated peptides from said cells.

In preferred embodiments of the method, the peptide elution buffer comprises citrate-phosphate buffer with a pH in the range of about 2.5 to about 5.0, and more preferably, is iso-osmotic with a pH of about 3.3.

In other preferred embodiments of the invention, the incubation time is about 15 seconds to about 5 minutes, and more preferably, is about 15 seconds to one minute.

In another aspect, the invention features a vaccine for treating a cancer patient who has at least one resectable tumor, comprising a composition of an immunologically effective amount of T cell epitopes recovered through acid elution of the T cell epitopes from the patient's resected tumor tissue.

In preferred embodiments, the vaccine further comprises a pharmaceutically acceptable adjuvant wherein said adjuvant is selected from the group consisting of dendritic cells and cytokines and any combination thereof.

In another aspect, the invention features a vaccine for treating a cancer patient, comprising a composition of an immunologically effective amount of T cell epitopes derived from allogeneic but HLA-matched tumor of the same histologic type present in the patient by acid elution of the T cell epitopes from the tumor tissue.

In preferred embodiments, the vaccine further comprises a pharmaceutically acceptable adjuvant wherein the adjuvant is selected from the group consisting of dendritic cells and cytokines and any combination thereof.

Other features and advantages of the invention will be apparent from the following description of the preferred embodiment, and from the claims.

DESCRIPTION OF THE DRAWINGS

FIGS. 7A-1–7A-3 and 7B-1–7B-3 are graphs showing the presence or absence of individual T cell epitopes that were eluted from three melanoma cell lines and then recognized by TIL 1074 (FIG. 7A-1–7A-3) or TIL 1128 (FIG. 7B-1–7B-3) mediated cytolysis of K4B target cells. The percent specific lysis of target cells is shown as a function of the individual HPLC fractions eluted from Mel 526, Mel 624, and Mel 397 human melanoma cell lines according to the present invention and loaded onto the target cells.

FIGS. 10A and 10B are mass spectra of HPLC peptide fractions 47 and 48 obtained from Mel 9742. FIG. 10A shows summation of the mass spectra obtained in the 500–1,600 m/z range. The $(M+H)^+$ ion at m/z=941 was selected for fragmentation to generate sequence data and used to generate a similar CID spectrum shown in FIG. 10B. Predicted and actual (underlined) masses for the fragments of the type b (carboxyl terminal cleavage) are shown above and type y (amino terminal cleavage) below the deduced sequence shown where X=isoleucine or leucine (SEQ. ID. Nos: 6–37)

FIGS. 12A–12D show epitope reconstitution with peptide p939. Melanoma-specific CTL: cultured TIL 1235 (FIG. 12A); clone A83 (FIG. 12B); clone A42 (FIG. 12C); and fresh TIL 6970 (FIG. 12D) were assayed in standard cytotoxicity assays against $^{51}$Cr-labeled T2 cells pulsed with p939 at the indicated concentrations.

In FIG. 13A, the effect of DC-tumor peptide vaccine was also assessed for more established d8 MCA205 tumors ("DC-MCA205 d8 model"). Animal negative control groups of animals received BM-DC that were not pulsed with peptide are shown as "DC-No peptide". The mean tumor size±SE of five mice per group, pooled from three different experiments, are depicted over time. Significant results at 95% (Fisher's exact test) confidence are indicated by an asterisk (*) in the individual panels.

FIGS. 14A–14D show that co-administration of low doses of recombinant murine interleukin 12 (rmIL-12) does not significantly enhance the ability of DC-MCA205 vaccines to stimulate an effective anti-tumor immune response but does augment the ability of immune cells taken from vaccinated animals to protect naive syngeneic animals from tumor challenge.

In FIGS. 14A and 14B 50 ng of rmIL-12 was administered i.p. on the day of DC-peptide vaccination and 1 day after DC injections into mice bearing established 4 day old "d4 model" (FIG. 14A) or 8 day old "d8 model" (FIG. 14B) s.c. MCA205 tumors. The animal vaccine treatment groups are as indicated in FIGS. 14A and 14B. ("DC-MCA205" indicates DC-peptide vaccine prepared with acid-eluted MCA205 peptides and "DC-MCA205+IL-12" indicates the same plus rmIL-12; "DC-Spleen" indicates DC-peptide vaccine prepared with control peptides obtained by acid-elution of normal syngeneic splenocytes and "DC-Spleen+IL-12" indicates the same plus rmIL-12.) Mean tumor size±SE of five mice per group, pooled from three different experiments, are depicted over time. Statistically significant results at 95% confidence (Fisher's exact method) are indicated with an asterisk (*).

FIG. 14C shows that DC-MCA205 vaccine-induced anti-tumor immunity does not depend on humoral immunity such as antibodies found in the serum of treated animals. Serum was obtained from vaccinated (3–4 immunizations) animals and pooled, prior to injection of 200 microliters of this material into syngeneic, naive mice that had been sublethally irradiated (500 rad) 2 days earlier. Naive mice were either not injected ("No Serum") or were injected with serum obtained from animals vaccinated with DC alone±rmIL-12, DC-spleen±rmIL-12 ("DC-Spleen+IL-12"; "DC-Spleen"), or DC-MCA205±rmIL-12 ("DC-MCA205+IL-12"; "DC-MCA205"), and subsequently inoculated s.c. with a normally lethal dose of MCA205 tumor cells. Tumor growth was then monitored to assess the protective impact of pre-treating the mice with the different serum groups. No statistically significant differences were noted in any of the treatment groups suggesting that humoral immunity was not important for effective anti-tumor immunity.

FIG. 14D shows that splenocytes derived from DC-MCA205 vaccinated animals can transfer immunity against MCA205 challenge to naive animals. Splenocytes were obtained from vaccinated (3–4 immunizations) animals and pooled, prior to injection of 10 million cells into syngeneic, naive mice that had been sub-lethally irradiated (500 rad) 3 days earlier. Naive mice were either not injected ("No Splenocytes") or were injected with splenocytes obtained from animals vaccinated with DC alone±rmIL-12, DC-spleen±rmIL-12 ("DC-Spleen+IL-12"; "DC-Spleen"), or DC-MCA205±rmIL-12 ("DC-MCA205+IL-12"; "DC-MCA205"), and subsequently inoculated s.c. with a normally lethal dose of MCA205 tumor cells. Tumor growth was then monitored to assess the protective impact of pre-treating the mice with the different splenocyte populations. Only animals receiving splenocytes derived from syngeneic mice vaccinated with DC-MCA205±rmIL-12 were protected against MCA205 challenge to a statistically significant degree (95% confidence by Fisher's exact method, indicated by asterisk (*)).

FIG. 16A shows that the costimulatory molecules B7 (CD80 and CD86) expressed by the DC used in vaccines are critical for the promotion of therapeutic anti-tumor immunity. DC-MCA205 vaccine-induced immunity is completely abrogated by co-injection of the B7 antagonist CTLA4-Ig. Fifty micrograms of CTLA4-IgG1 was admixed with DC-MCA205 and administered to mice bearing established 4 day old tumors on days 0, 4, 8, and 12 ("DC-MCA205+CTLA4-Ig"). For FIGS. 16A–16D, DC pulsed with MCA205 tumor-derived peptides is "DC-MCA205"; DC pulsed with normal spleen peptides is ("DC-Spleen").

FIG. 16B shows that DC-MCA205 vaccine-induced anti-tumor immunity is partially or completely abrogated by the neutralization of the Th1-associated cytokines interferon-gamma (IFN-γ), tumor necrosis factor-alpha (TNF-α), and IL-12 in vivo. One milligram of neutralizing anti-mIL-12 (C17.8, rat IgG2a) ("DCMCA205+Anti-IL-12") or 350 micrograms of neutralizing anti-mTNF-α+anti-mIFN-γ ("DC-MCA205+Anti-IFN/TNF") were injected i.p. into mice 1 hour before the first and second DC-MCA205 vaccinations given on days 3, 10, and 17.

FIG. 16C shows that a similar neutralization of the Th2-associated cytokine mIl-4 using 300 micrograms of anti-mIL-4 (11B11, rat IgG2a) ("DC-MCA205+Anti-IL-4") similarly partially abrogates the anti-tumor efficacy of DC-MCA205 vaccines.

FIG. 16D shows that DC-MCA205-induced anti-tumor effects are completely inhibited by the in vivo depletion of either the CD4+ or CD8+ T cell subsets. One milligram of depleting anti-CD4 ("DC-MCA205+Anti-CD4") or anti-CD8 ("DC-MCA205+Anti-CD8") or both, ("DC-MCA205+Anti-CD4/CD8") was injected i.p. into mice 2 days before the first vaccination with DC-MCA205 and was repeated 10 days later.

FIGS. 19A and 19B are graphs for 2 patients showing anti-melanoma CTL may be generated in vitro from melanoma patient peripheral blood responders stimulated with autologous dendritic cells pulsed with the indicated synthetic melanoma peptides. Results are shown as percent lysis of HLA-A2+ Mel 624. For each patient bar 1 is MART-1 27–35; bar 2 is MART-1 32–40; bar 3 is gp100 280–288; bar 4 is gp100 457–466; bar 5 is Tyrosinase 1–9; and bar 6 is Tyrosinase 368–376.

DETAILED DESCRIPTION OF THE INVENTION

I. Definitions

Figure 1:
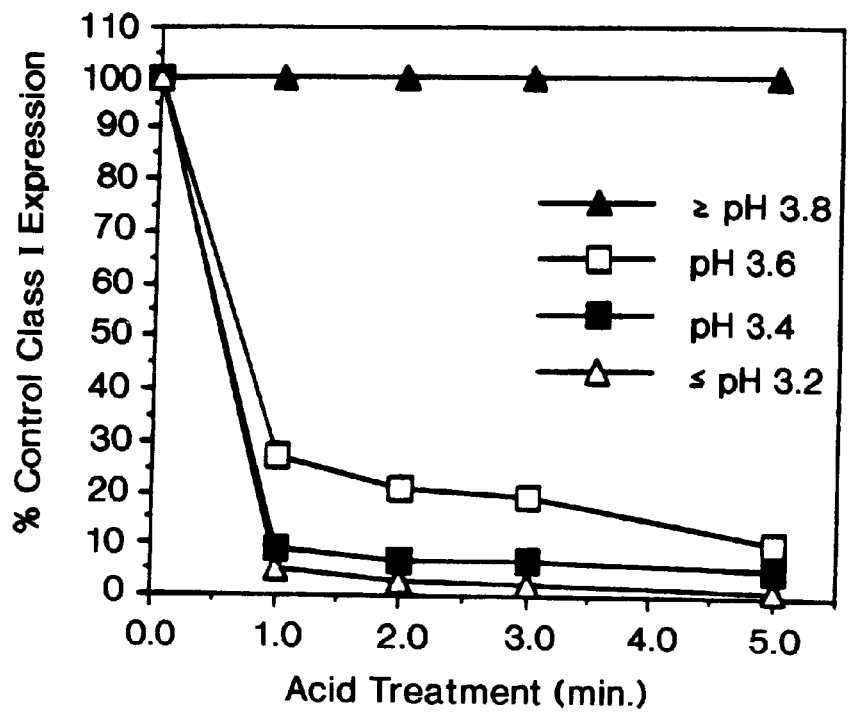
FIG. 1 shows the results of flow cytometry analysis of Mel 624 target cells that were treated with citrate-phosphate buffer at various pHs (3.0, 3.2, 3.4, 3.6, 3.8, 4.0 and 5.0) and assayed for class I molecule expression in indirect immunofluorescence assays using W6/32 monoclonal antibody. The results shown are the percentage of the W6/32 reactivity of peptide elution buffer-treated Mel 624 cells versus the W6/32 reactivity of control (untreated) Mel 624 cells.

As used herein, the term "Major Histocompatibility Complex (MHC)" refers to a genetic region found in all mammals whose products, including but not limited to class I and class II molecules, function in the presentation of peptides to effector T lymphocytes. In the human, this complex is denoted as HLA. In the mouse, this complex is denoted as H-2. Effector T cells are restricted by, and react to, autologous (self) MHC products. MHC molecules expressed on cells contain an antigen-binding site (ABS) in which peptides may be bound and presented to form "MHC-peptide complexes" and constitute "MHC-bound peptides." For example, "class I molecules" are presented to T cells and T cell recognition of such peptides is considered to occur in the context of such MHC molecules/complexes.

The term "antigen" is defined as a molecule which induces clonal lymphocytic proliferation and the generation of antigen-specific immunoglobulin from B lymphocytes and/or the generation of antigen-specific effector T lymphocytes.

"Epitope" or "antigenic determinant" refer to the relevant portion of an antigen that is recognized by effector cell receptors (i.e., immunoglobulin or T cell receptors). "T cell epitope" refers to a peptide that is presented on the cell surface of a target cell that is bound to an MHC gene product/molecule and is recognized by a T cell.

"Immunogenic" refers to the capacity of a substance or molecule (generally a protein or protein fragments (peptides)) to serve as an antigen.

"Peptide elution buffer" as used herein refers to the reagent solution that, when incubated in the presence of cells, results in the elution of previously MHC-bound T cell epitopes, i.e., peptides. In the present invention, the peptide elution buffer preferably is acidic, and more preferably has a pH of between about 2.7 and about 5.0. In the preferred embodiment, the peptide elution buffer is iso-osmotic, phosphate-citrate buffer of pH 3.3. Such extracted peptides may be subsequently isolated and analyzed biochemically.

The terms "peptide-loading" and "peptide pulsing" refer to the process by which exogenous peptides are incubated in the presence of target cells in order to establish an equilibrium that results in the occupation of MHC molecule antigen binding sites by these same exogenous peptides.

A "target" is a cell that elicits an effector cell response. Positive T effector cells only respond to target cells that express the relevant MHC-encoded gene products presenting relevant T cell epitopes.

The term "effector" or "effector cell" refers to a lymphocyte that mediates an antigen-specific response. The effector cell responses may include, but are not limited to, proliferation, cytotoxicity, and/or secretion of factors (immunoglobulin or cytokines by B cells, cytokines by T lymphocytes).

The terms "elute", "remove" "extract", and "strip" are used interchangeably to mean the physical removal or dissociation of T cell epitopes/peptides from MHC molecules expressed on the surface of viable cells.

"Viable" or "viability" refers to the maintenance of physical integrity of a cell and the ability of the cell to metabolically regenerate membrane components including MHC molecules after treatment with peptide elution buffer.

"Antigen presenting cell" refers to a cell capable of presenting T cell epitopes to T cells, and more specifically, a cell that has the capability of stimulating naive T cells to responding in an antigen-specific manner.

An "adjuvant" refers to any substance that facilitates or enhances the generation of an antigen specific T cell immune response when coinoculated with a given antigen in vivo.

A "dendritic cell" or "DC" is an antigen presenting cell with morphologic characteristics, including extensive membrane ruffling and dendrites, with the capability to migrate within the body to lymphoid organs. DC's are considered to be a biologic adjuvant.

A "naive T cell" is one that has never encountered the antigen for which it is specific.

II. Methods—Acid Elution of Peptides

According to the present invention there is an improved and novel method of eluting MHC-bound peptides from the cell surface of viable cells which is rapid and which is non-toxic to the cells. Since cells are not killed in this process, they are able to regenerate their MHC-peptide complexes so that the regenerated MHC-bound peptides may be subsequently reeluted. The method uses far fewer cells than methods that employ cell cytolysis thereby expanding the range of cells from which such peptides may be isolated to cells which do not grow well in tissue culture or in vitro.

The method of the present invention may be carried out using any reagent solution that is capable of eluting MHC-bound peptides/T cell epitopes from the surface of viable cells without significantly affecting the viability of the cells (non-toxic). Therefore, cells so treated are able to reexpress MCH-peptide complexes. Preferably, the reagent solution is a peptide elution buffer which has an acidic pH, preferably between about 2.7 to about 5.0. Most preferably, the peptide elution buffer is iso-osmotic, citrate-phosphate buffer with pH 3.3. The MHC-bound peptides that are ultimately expressed on the surface of target cells are the result of either pulsing peptides onto the targets or infecting the target cells with a virus as described in detail below.

It is known, for example, that $CD8^+$ CTL's recognize HLA-A2 class I-presented immunogenic melanoma-specific peptide or peptides on the surface of HLA-A2$^+$ melanoma target cells. $CD4^+$ T cells may similarly recognize melanoma-specific peptides presented in the context of tumor class II molecules. Therefore the isolation and characterization of such melanoma-presented peptides may lead to the development of synthetic peptide vaccines capable of being used as an immunogen to elicit anti-melanoma T cell responses. Additionally, approaches to identify such peptides may have relevance in studies of immune reactivity to other tumor, viral or autoimmune systems where clear MHC-restricted T cell reactivities can be identified.

Another aspect of the present invention is the use of acid-eluted peptides/T cell epitopes from a patient's tumor cells that are pulsed onto autologous dendritic cells to treat that particular patient. Alternatively, acid-eluted peptides can be obtained from HLA matched allogeneic tumor cell lines to serve as antigen pulsed onto autologous antigen presenting cells, preferably dendritic cells, for treating patients with cancer. Preferably such acid-eluted peptides would come from the same individual who is to be treated and such peptides are administered as a vaccine in conjunction with a pharmaceutically accepted and approved adjuvant, preferably autologous dendritic cells.

In the following example melanoma cells were treated with iso-osmotic, citrate-phosphate buffer at various acidic pHs to determine the kinetics and pH dependency of class I molecule expression. However, it should be readily apparent that the method of the present invention is not limited to use with melanoma cells. Indeed, the present invention may be employed with any cell bearing MHC determinants, such as, for example, colon, squamous cell, gastric, breast, prostate, lung, cervical and ovarian carcinomas.

EXAMPLE 1

Elution With Peptide Elution Buffer

The metastatic human melanoma Mel 624 (HLA-A2$^+$) cell line (a gift, available on request, from Dr. S. Rosenberg, National Institute of Health, Bethesda, Md.) (Mel 624 cell line was deposited with the American Type Culture Collection, of 10801 University Blvd., Manassas, Va. 20110-2209 on Jan. 15, 1999 under ATCC accession number CRL-12642.) was used as the prototypic target cell for treatment with the method of the present invention. This technique has been determined to be equally effective for elution of peptides from cultured cell lines as well as from fresh tissues.

The Mel 624 cells were cultured in tissue culture media ("TCM") consisting of RPMI-1640 media that was supplemented with 2mM L-glutamine, 100 U/ml penicillin, 100 μg/ml streptomycin, 50 μg/ml gentamycin, and 10% heat-inactivated fetal calf serum. All regents were from Gibco, Grand Island, N.Y. The cells were incubated at 37° C. at 5% $CO_2$ in a humidified incubator. Mel 624 cells were grown in T225 flasks (Costar, Cambridge, Mass.). Single cell suspensions of the Mel 624 cells were generated by trypsinization of the cells using Trypsin-versene (Whittaker Bioproducts, Walkersville, Md.) followed by washing of the cells with TCM and Hank's Buffered Saline Solution ("HBSS") (Gibco). Adherent cell cultures may be treated either in situ in flasks or after adherent cells have been trypsinized and pelleted. Cells grown in suspension or cells derived from fresh tissue were pelleted and treated with peptide elution buffer. Trypsinization of target cells had no effect on the expression level of class I molecules prior to extraction or the sensitivity of cellular viability.

In order to cause virus-derived, class I-presented peptides to be expressed at target cell surfaces, Mel 624 target cells were infected with influenza A/UDORN. Influenza A/UDORN was a gift, and available upon request, from Dr. W. Biddison, National Institute of Health ("NIH") Bethesda, Md. and was grown in the allantoic sac of fertilized chicken eggs according to the method of McMichael, A. J., et al., *Eur. J. Immunol.* 8:705 (1978), the disclosure of which is incorporated herein by reference. The resulting harvested fluid contained influenza virus at a titer of $2 \times 10^8$ PFU/ml when it was assayed for cytopathic plaque formation on confluent monolayers of MDCK cells (ATCC accession No. CCL 34). Mel 624 tumor cells were infected with influenza A/UDORN at 1 PFU/cell in serum-free TCM for 1 hour. Heated-inactivated fetal calf serum was then added to the reaction mixture to a final concentration of 10%. The infected cultures were then incubated for an additional 18 hours at 37° C. in order to allow expression of virus-derived, class I-presented peptides at the target cell surface. At the end of the incubation time the cells were washed twice with HBSS.

Individual samples of $10^5$ trypsinized cells/sample were pelleted by centrifugation at 500×g for 5 minutes, or alternatively, cell lines to be extracted were left as adherent populations in T225 flasks. Target cell pellets or confluent flask-adherent cells ($2 \times 10^8$ total cells) were washed three times with 10 ml of HBSS in order to remove contaminant calf serum proteins. Residual HBSS was removed by aspiration after the final wash.

Citrate-phosphate buffers (0.131 M Citric Acid/0.061 M $Na_2HPO_4$, 290 mOsmol/kg $H_2O$ (iso-osmotic) was made essentially as outlined by the method of Suguwara, S., et al., *J. Immunol Meth.* 100:83 (1987), the disclosure of which is incorporated herein by reference, except that 1% (w/v) bovine serum albumin (BSA) was not added in order to avoid molar excesses of contaminant BSA-derived peptides. The pH of the citrate-phosphate buffer (stock, unadjusted pH 3.0) was adjusted with 5N NaOH or 5N HCl to the desired final pH (pH 2.7–5.0), depending on the need of the particular study conducted.

To each sample of resuspended cells 100 μl of citrate-phosphate buffer at room temperature was then added at a pH of 3.0, 3.2, 3.4, 3.6, 3.8, 4.0 or 5.0 for the indicated time period (0–60 minutes). The buffer treated cells and the cell pellets were resuspended by gentle pipetting or by gently rocking flasks (5 ml/flasks) by hand for approximately 5 minutes. At the end of incubation, 3 ml of TCM containing 10% FBS was added to neutralize the acid in order to maintain extended cell viability. These volumes were found not to be critical; any volume sufficient to completely coat all sample cells was found to be effective. The cell suspensions were then pelleted (500×g for 3 min.) and the cell resulting cell-free supernatant was harvested. Alternatively, cell-free supernatants were removed from adherent cell preparations by pipet and the supernatants which contained eluted peptides were stored at −70° C. until fractionation procedures were performed later.

It was found that target cells survived the aforedescribed buffer treatment with no or very little loss of viability, as assessed by trypan blue exclusion, by rapidly neutralizing the cell pellets or flask-adherent cells with a 15 ml wash of TCM. The cell pellets were then resuspended in TCM or, in the case of flask cultures, the cells were recultured in a second aliquot of TCM. Target cells treated in such a way regenerated their class I MHC-peptide complexes within approximately 10–18 hours at which time they could be subjected to another round of peptide elution buffer stripping.

Antibodies

Target cells and donor peripheral blood lymphocytes (PBL's) were phenotyped for HLA-A2 expression using the BB7.2 anti-HLA-A2 (polymorphic) monoclonal antibody (MAb). The MAb was obtained by culturing BB7.2 hybridoma-ATCC accession number HB82. Total class I expression was monitored by the W6/32 anti-class I (monomorphic) monoclonal antibody (W6/32 hybridoma obtained from ATCC (accession number HB9S)) The BBM.1 MAb was used to detect β-microglobulin, and the HC-10 MAb (Gillet, A. C., et al., *Eur. J. Immunol* 20:759 (1990), the disclosure of which is incorporated by reference) was used to measure free, non-$β_2$-microglobulin associated, class I heavy chains (HC-10 hybridoma obtained from Dr. H. Ploegh, Massachusetts Institute of Technology, Cambridge, Mass., and available upon request. Total class II expression was determined using the L243 anti-HLA-DR (monomorphic) MAb. All MAbs, except for HC-10, were derived from hybridoma culture supernatants.

Immunofluorescence Assays

The neutralized cells were then assayed for class I molecule expression in indirect immunoflorescence assays using the MAbs described above according to the methods of Biddison, W. E., et al., *J. Immunol* 129:730 (1982), and Mitchell, M. S. et al., *J. Clin. Oncol.* 10:1158 (1992), the disclosures of which are incorporated herein by reference. The W6/32 monoclonal antibody (anti-HLA class I, monomorphic determinant) was used along with a secondary FTIC-labeled goat anti-mouse IgG (F(ab$^1$) $_2$) (Organon Teknika, Durham, N.C.). HC-10 was used as a 1/500 dilution of ascites in HBSS. The assays were monitored by flow cytometry performed on a FACScan flow cytometer (Becton Dickinson, Mountainview, Calif.) with reactivity expressed in mean fluorescence channel (MFC) units. The gain setting (laser amplifier) is set by the operator each time the cytometer is run based on a negative control sample. Since this control varies from run to run, the MFC scale is arbitrarily set for each run, although within each run the fluorescense scale is uniform and proportional.

The results of treatment of Mel 624 cells with peptide elution buffer shown in FIG. 1 are reported as the percentage of the W6/32 MFC reactivity of treated cells versus the W6/32 MFC reactivity of control, untreated, Mel 624 cells. Treatment of Mel 624 cells with citrate-phosphate buffer with pH$≦$3.8 resulted in a rapid, $≦$1 minute, denaturation of class I complexes as measured by W6/32 reactivity. Treatment of Mel 624 target cells with citrate-phosphate buffer with a pH$≧$3.8 had minimal effect on the level of expression of W6/32 reactive class I species. Class II complexes undergo conformational changes at or below pH 4.5. Gorga, J. C., et al., *Crit. Rev. Immunol.* 11: 305 (1992), the disclosure of which is incorporated herein by reference.

In the following example the viability of cells treated with citrate-phosphate buffer was assessed.

EXAMPLE 2

Figure 2:
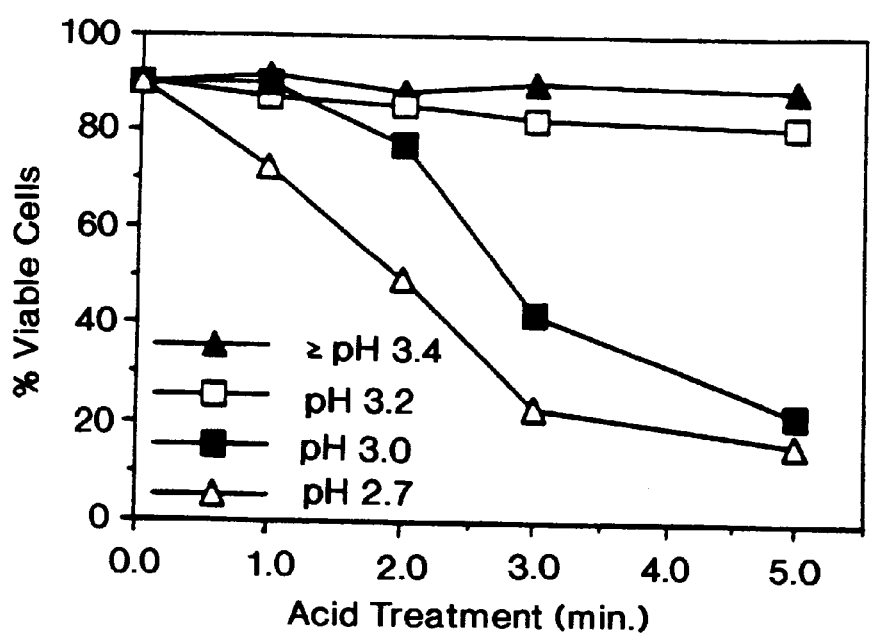
FIG. 2 is a graph showing results of studies of Mel 624 target cell viability upon treatment of the cells with citrate-phosphate buffer at pHs of 2.7, 3.0, 3.2, and $\geq 3.4$ (3.4, 3.6, 3.8, 4.0, 5.0) for time intervals up to five minutes.

Mel 624 target cells were treated as in Example 1 with iso-osmotic, citrate-phosphate buffer at pHs of 2.7, 3.0, 3.2, 3.4, 3.6, 3.8, 4.0, and 5.0. Cells were assessed for their viability by monitoring trypan blue dye exclusion in incubations of 1–2 minutes. As shown in FIG. 2, citrate-phosphate buffers with pH≦3.2 were toxic to Mel 624 target cells in incubations exceeding 1–2 minutes. Incubations carried out in buffers with pH≧3.2 were well tolerated by the cells and did not lead to significant cell death ever after 5 minutes of treatment. In order to optimize the class I denaturing effects as well as cell viability, iso-osmotic, citrate-phosphate buffer at a pH of 3.3 was used for all subsequent studies.

The sensitivity of class I molecules expressed by diverse cell types was determined in the following example.

EXAMPLE 3

Tumor cell lines used were melanoma cell lines Mel 397 (HLA-A2⁻) and Mel 624 (HLA-A2⁺) (gifts, available on request, from Dr. S. Rosenberg, NIH), PCI-50 squamous cell carcinoma, HR gastric carcinoma (gifts, available on request, from Dr. T. Whiteside, Pittsburgh Cancer Institute, Pittsburgh, Pa.) and the EBV-transformed B cell lines K4B (HLA-A2⁺ (gift, available on request, from Dr. Biddison, NIH), C1R.A2 (an HLA-A2⁺ transfectant of the HLA-A,B null C1R cell line as described by Storkus, W. J. et al., *Proc. Natl. Acad. Sci. USA* 88:5989 (1991), the disclosure of which is incorporated herein by reference, and C1R.Bw58 (an HLA-BW58⁺ transfectant of the HLA-A,B null C1R cell line as described by Storkus, W. J., et al., *Proc. Natl. Acad. Sci. USA* 86:2361 (1989). All tumor cell lines were cultured in TCM as described in Example 1.

Figure 3:
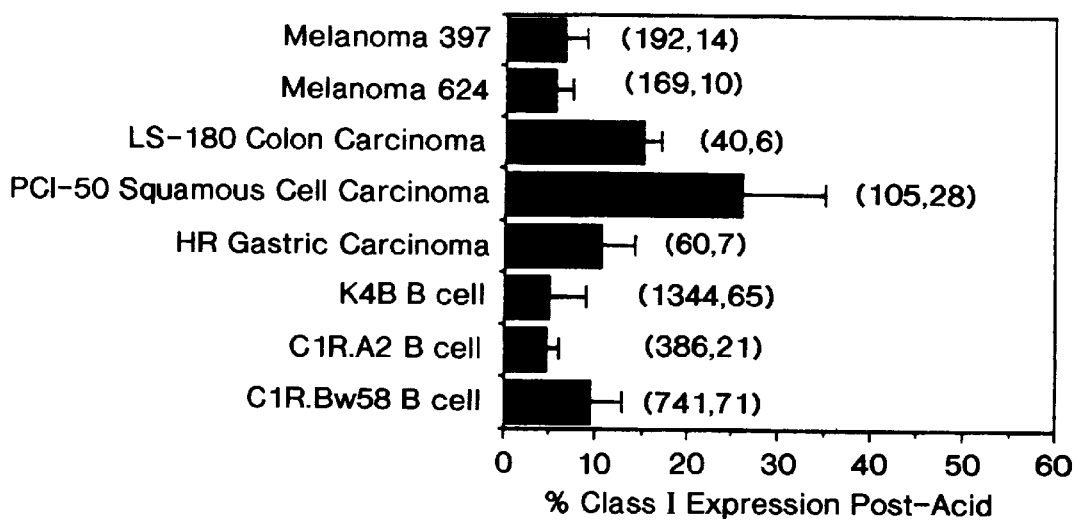
FIG. 3 is a graph showing results of flow cytometry analyses of various tumor cell lines that were treated with iso-osmotic, pH 3.3 citrate-phosphate buffer for 1 minute and then assayed for class I molecule expression in indirect immunofluorescence assays using W6/32 monoclonal antibody. The results shown are the mean standard deviation of the percentage of the W6/32 reactivity of the peptide elution buffer-treated cells versus the W6/32 reactivity of control cells. Pre-and post treatment W6/32 reactivity mean fluorescence channel values are in parenthesis.

The various tumor cells were treated with pH 3.3 iso-osmotic, citrate-phosphate buffer for one minute followed by neutralization and flow cytometric analysis of class I molecule expression using the W6/32 monoclonal antibody as described in Example 1. The results, shown in FIG. 3, show that in all cases, treatment greatly reduced cellular reactivity with the W6/32 monoclonal antibody within the 1 minute reaction time. Approximately 85–95% of W6/32 reactive class I species were removed on all the target lines that were tested, with the possible exception of the PCI-50 squamous cell carcinoma line which exhibited an approximately 74% reduction. Treatment with peptide elution buffer appeared to decrease the expression of both HLA-A and HLA-B locus class I determinants equally well since both the C1R.A2 and C1R.Bw58 transfected cell lines which express only the HLA-A2 or HLA-Bw58 class I molecules, respectively, appeared to be similarly affected by pH 3.3 treatment. Such lack of differential sensitivity of the present method of the claimed invention with respect to the type of class I molecule, HLA-A, HLA-B, or HLA-C was also supported in view of the near absolute reduction in W6/32 reactivity of heterozygous class I expressing target cells such as Mel 624 (HLA-A2, -A3, -B7, -B14, -Cw7) or K4B (HLA-A1, -A2, -B7, -B8) after these cells were treated for 1 minute at pH 3.3.

While the foregoing results show that treatment with peptide elution buffer greatly reduces cellular reactivity with the W6/32 Ab which recognizes a monomorphic combinatorial determinant requiring class I heavy chain-$\beta_2$-microglobin ($\beta_2$M), it was not clear whether the individual class I heavy and light chains ($\beta_2$m) remained cell associated. In the following example the association of the heavy and light chains was determined upon treatment.

EXAMPLE 4

Single cell suspensions of Mel 624 cells were generated by trypsinization and washing as described in Example 1. The resulting cells were partitioned into four $10^6$ cell frac-tions and treated with pH 3.3 iso-osmotic, citrate-phosphate buffer for 0, 15, 30, or 60 seconds. The samples were then neutralized by addition of TCM and washing and pelleted by centrifugation at 500×g for 5 minutes. Indirect immunofluorescense assays were performed as in Example 1 using primary monoclonal reagents and a FITC-conjugated F(ab')₂ goat anti-mouse IgG (Organon Teknika). The following primary monoclonal reagents were used: W6/32, HC-10, BBM-1, L234, and a negative control, primary antibody OKT3 which is non-reactive with the Mel 624 target cells. HC-10 was used as 1/500 dilution of ascites in HBSS. Indirect immunofluorescence assays were performed as described in Example 1. The results shown below in Table 1 are reported as mean fluorescence channel number (MFC) units.

TABLE 1

| Time of pH 3.3 Treatment | MAb Reactivity (MFC) | | | | |
|---|---|---|---|---|---|
| (control) (sec) | W6/32 (H + $\beta_2$m) | BBM-1 ($\beta_2$m) | HC-10 (free H) | L243 | OKT3 |
| | | | | (HLA-DR) | |
| 0 | 169 | 67 | 9 | 477 | 8 |
| 15 | 36 | 18 | 60 | 565 | 10 |
| 30 | 18 | 19 | 60 | 522 | 10 |
| 60 | 18 | 17 | 71 | 529 | 9 |

H = heavy chain; $\beta_2$m = $\beta_2$ microglobulin; HLA-DR = class II molecule.

The above results show that treatment of Mel 624 target cells with pH 3.3. citrate-phosphate buffer led to the rapid loss of reactivity (15–30 seconds) with both the W6/32 and BBM-1 MAbs, the gain of reactivity with HC-10, and no change of reactivity with the L234 monoclonal reagent. Longer buffer treatments were not determined to lead to any significant further denaturation of class I complexes. Such results indicate that class I heavy chains remain associated with the cell surface in pH 3.3 buffer, but that $\beta_2$m is lost into the cell-free supernatant. As previously reported by Suguwara, S., et al., *J. Immunol Meth.* 100:83 (1987), the disclosure of which is incorporated herein by reference, class II molecules that are recognized by the L243 reagent were not affected by cellular peptide elution buffer treatments as low as pH 3.0.

While the foregoing results suggest that there is a qualitative loss of native class I molecules on peptide elution buffer-treated target cell membranes, CD8⁺ T cell recognition of target cells bearing the appropriate class I restricting element serves as a much more sensitive index of limiting class I molecule expression. In the following example cytotoxic T lymphocyte (CTL) recognition of target cells after treatment according to the methods of the present invention was examined.

EXAMPLE 5

Anti-influenza peptide CTL lines were generated by the method of Carbone, F. R., et al., *J. Exp. Med.* 167:1767 (1988), the disclosure of which is incorporated herein by reference. Briefly, 40–60×10⁶ peripheral blood lymphocytes (PBLs) were obtained from normal, healthy HLA-A2⁺ donors by venipuncture. Ficoll-Hypaque separations were then performed using the lymphocyte separation medium (LSM) kit according to the manufacturer's protocol (Organon Teknika). Peripheral blood primary stimulations were performed as follows: the lymphocytes were cultured in 10 ml of AIM-V media (Gibco) for 7 days that contained 25 µg/ml of the synthetic influenza matrix nonameric peptide Flu M1 57–68 (KGILGFVFTLTV-Lys-Gly-Ile-Leu-Gly-Phe-Val-Phe--Thr-Leu-Thr-Val) (SEQ ID NO: 1) which was synthesized by the Peptide Synthesis Facility, Shared Resource, Pittsburgh Cancer Institute, Pittsburgh, Pa. Weekly restimulations were then performed by taking $5 \times 10^6$ viable responders and adding $10^7$ irradiated (3,000 rad) HLA-A2$^+$ allogeneic PBLs in 10 ml of AIM-V media supplemented with 25 µg/ml Flu M1 peptide plus 50 IU/ml rhIL-2 (Chiron, Emeryville, Calif.). Fresh AIM-V media with 50 IU/ml rhIL-2 was added to rapidly proliferating T cell cultures as was needed. The GL1 anti-Flu CTL line was selected for use after tertiary boosting and after display of specific recognition of Flu M1 peptide that was presented in the context of HLA-A2 expressed by melanoma or B cell targets. GL1 lysed both influenza A/UDORN infected HLA-A2$^+$ targets or Flu M1 peptide-pulsed HLA-A2$^+$ targets, but not control uninfected or non-peptide pulsed targets (data not shown).

The influenza A (Flu M1 57–68) peptide specific, HLA-A2-restricted CD8$^+$ CTL effector line (GL1) as generated according to the foregoing description was investigated to see if such a CTL effector line could recognize influenza infected Mel 624 target cells that were treated with peptide elution buffer according to the methods of the present invention.

Mel 397 (HLA-A2$^-$) and Mel 397 (HLA-A2$^+$) were mock infected (treated with TCM only) or infected with influenza A/UDORN at 1 pfu/cell for 18 hours at 37° C. as described above. 1–2×10$^6$ infected cells were then trypsinized, washed with TCM, and pelleted by centrifugation. The cells of both cell lines were then labeled with 100 µCi of Na$_2$$^{51}$CrO$_4$ (New England Nuclear, Boston, Mass.) by incubating for 1 hour at 37° C. The cells were then washed twice with HBSS to remove free label and treated with either HBSS at pH 7.4 or iso-osmotic, citrate-phosphate buffer at pH 3.3 for 1 minute. TCM was then added to the treated cells to neutralize the acid.

Some buffer-extracted targets were allowed to regenerate their class I-peptide complexes by subsequently culturing the cells at 37° C. for up to 18 hours in TCM that contained 100 µCi Na$_2$$^{51}$CrO$_4$. A portion of these regenerated target cells were treated a second time with pH 3.3 citrate-phosphate buffer.

Standard 4 hour cytotoxicity assays with GL1 CTL effector cells were then carried out on the various groups of treated target cells after the cells were neutralized of acid by washing with TCM followed by HBS. In order to perform the assays 100 µl of target cells were loaded into each assay well of 96-well U-bottomed microculture wells at $10^4$ targets/well. Direct target sensitivity to GL1 (anti-Flu M1 peptide-specific, HLA-A2-restricted) CTL was assessed by adding GL1 effector cells at an effector-to-target ratio of 1:1. The cells were then incubated for 4 hours at 37° C. The control, spontaneous release, constituted target cells and TCM only (for assays involving peptides this constituted 100 µl of target cells plus 125 µl of TCM; if no peptides were involved, targets and TCM were used at 100 µl each). The maximum release control consisted of $10^4$ target cells plus 100 µl of Triton X-100 (Sigma, St. Louis Mo. (10% in ddH$_2$O)) in directed assays or 125 µl of Triton X-100 in peptide pulsing assays. After the 4 hour incubation, the contents of the 96-well plates were centrifuged at 50×g for 5 minutes to pellet the cells, and 100 µl of supernatant was harvested for counting in an LKB gamma counter (Pharmacia, Piscataway, N.J.).

In the following table the percent specific lysis for these studies was calculated as (Experimental cpm-Spontaneous cpm)/(Maximum cpm-Spontaneous cpm)×100%. Spontaneous release in all cases was always less than 15% of the maximal release for all targets assessed.

TABLE 2

| Target | HLA-A2 (+/−) | Flu (+/−) | Primary pH 3.3 Treatment/ Regenerate for: | | | Secondary pH 3.3 Treatment | GL1 % Specific Lysis (E/21) |
|---|---|---|---|---|---|---|---|
| | | | 0h | 4h | 18h | | |
| Mel 397 | − | − | − | − | − | − | 4 |
| | − | + | − | − | − | − | 7 |
| | − | + | + | − | − | − | 1 |
| | − | + | − | + | − | − | 0 |
| | − | + | − | − | + | − | 1 |
| | − | + | − | − | + | + | 2 |
| Mel 624 | + | − | − | − | − | − | 5 |
| | + | + | − | − | − | − | 20 |
| | + | + | + | − | − | − | 1 |
| | + | + | − | + | − | − | 0 |
| | + | + | − | − | + | − | 26 |
| | + | + | − | − | + | + | 1 |

As shown in Table 2, Mel 624 (HLA-A2$^+$) targets were recognized and lysed by GL1 effector cells after influenza infection. Recognition of targets by the GL1 cells was destroyed by pH 3.3 treatment, but such recognition was regenerated after 18 hours of incubation in TCM at 37° C. Regeneration did not take place after only 4 hours of incubation. The regenerated recognition or sensitivity to GL1 CTL-mediated lysis was destroyed by a second pH 3.3 treatment. Mel 397 (HLA-A2$^-$) cells were not recognized by the HLA-A2 restricted GL1 CTL under any of the conditions the cells were subjected to.

As shown in the preceding example GL1 CTL were unable to recognize influenza-infected Mel 624 target cells that were treated with peptide elution buffer according to the methods of the present invention. This finding, coupled with the acid-associated loss of β$_2$m, suggested that the class I-bound peptides (CD8$^+$ T cell epitopes) might also be released from the surface of cells treated with peptide elution buffer as presently described. In the following example, this possibility was explored.

EXAMPLE 6

$2 \times 10^8$ Mel 624 cells in T225 culture flasks were infected with influenza A/UDORN at 1 pfu/cell for 18 hours at 37° C. as described in Example 1. The influenza-infected cells and control (uninfected) Mel 624 target cells were then treated with pH 3.3 iso-osmotic citrate-phosphate buffer for 1 minute as described in Example 1 in situ while still adherent to T225 culture flasks. The peptides in the resulting cell-free, buffer-extracted supernatant were isolated by concentrating and desalting the supernatant on SepPak C$_{18}$ cartridges (Millipore, Bedford, Mass.) according to the manufacturer's protocols. In brief, columns were attached to 5 cc syringes (Becton-Dickinson, Rutherford, N.J.) and prewashed with 2–3 ml of acetonitrile (Fisher Scientific, Pittsburgh, Pa.) and then washed with 2–3 ml of ddH$_2$O. Buffer extracts were then loaded into the syringes and the extracts were allowed to gravity elute through the SepPak cartridges. The peptide-loaded columns were then washed with 5 ml of ddH$_2$O and the bound material was eluted with 1–2 ml of 60% acetonitrile/40% ddH2O. The eluted material was then lyophilized in a Savant SpeedVac (Farmingdale, N.Y.) to near complete dryness with approximately 10 µl of residual fluid remaining, and then reconstituted in 0.5 ml of iso-osmotic, citrate-phosphate buffer at pH 3.3. Peptides that were ≦3,000 Mr. were then isolated by fractionation on Centricon-3 ultrafiltration devices (Amicon, Cambridge, Mass.) according to the manufacturer's protocols by centrifugation at 2000×g for 1–2 h. The resulting bulk peptides were then fractionated by liquid chromatography (LC), preferably reverse phase high performance liquid chromatography (RP-HPLC), as described herein.

Figure 4A:
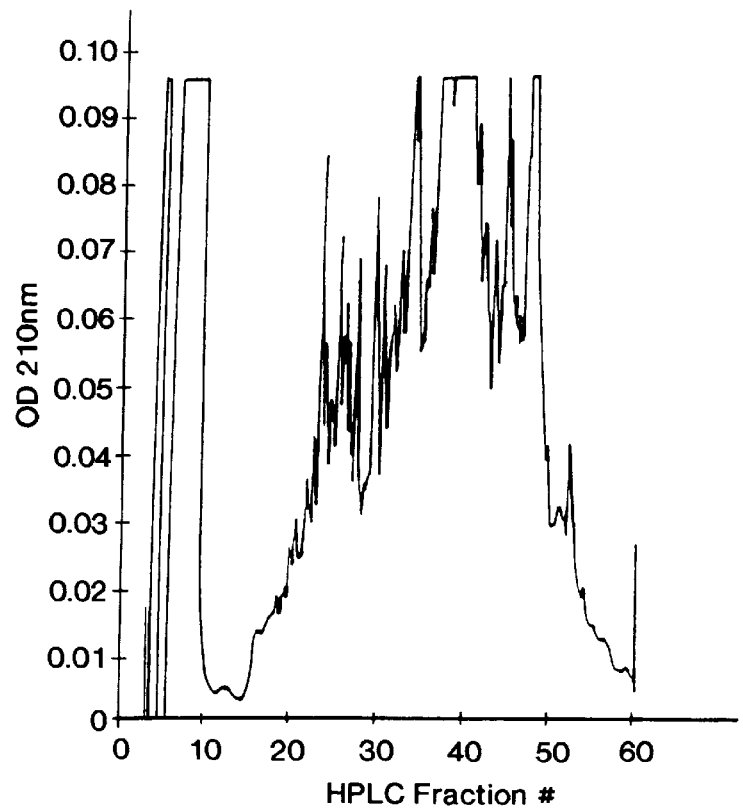
FIG. 4A is an RP-HPLC chromatogram of endogenously processed peptides that were eluted from influenza A/UDORN-infected Mel 624 cells that were treated with iso-osmotic, pH 3.3 citrate-phosphate buffer according to the present invention and monitored at 210 nm.

Briefly, the bulk peptides were fractionated on a $C_{18}$ reverse-phase (RP) column (Alltech, Deerfield, Ill.) using an Eldex, (San Carlos, Calif.) programmable pump in a 99.92% water/0.08% trifluoroacetic acid (TFA) to 39.935 water/0.07% TFA/60% acetonitrile gradient. The flow rate was maintained at 1.0 ml/minute and 1 ml fractions were collected. Each incremental gradient was linear. The HPLC runs were monitored for peptides species by monitoring the absorbence of the peptides at 210 nm using a multi-diode array detector (Linear UVIS, Reno, N.V.). The resulting HPLC fractions were transferred to Eppendorf polypropylene tubes and lyophilized. The results of the RP-HPLC are shown in FIG. 4A.

Figure 4B:
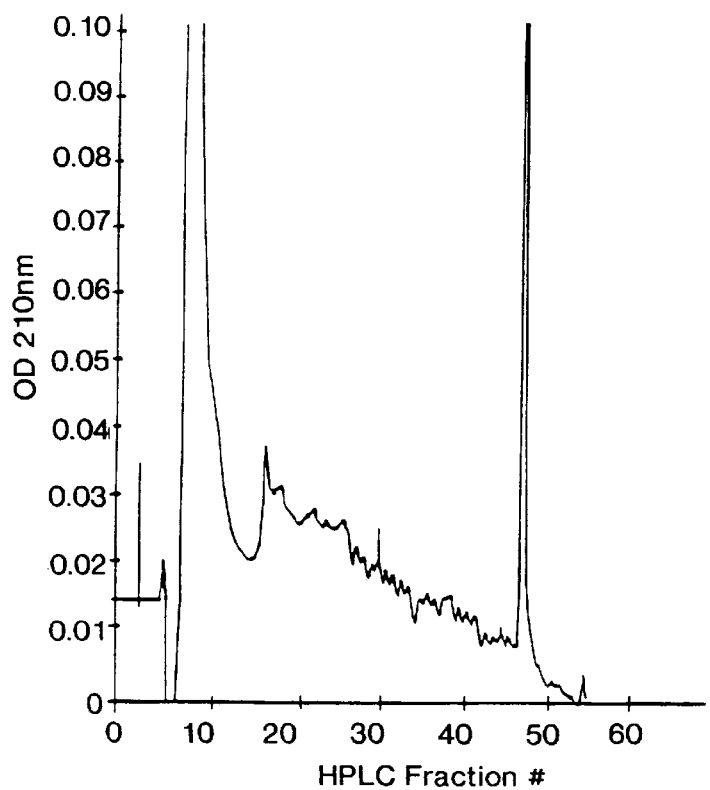
FIG. 4B is an RP-HPLC chromatogram of the synthetic peptide Flu M1 58–66.

Since influenza A infection of HLA-A2$^+$ target cells had been previously shown to result in the endogenous processing and presentation of the immunodominant Flu M1 58–66 sequence, and the GL1 CTL line was primed against a peptide containing this sequence (i.e., Flu M1 57–68), synthetic Flu M1 58–66 peptide was also fractionated by HPLC. The Flu M1 sequence eluted in HPLC fractions 47 and 48 (47–48% acetonitrile) is shown in FIG. 4B.

EXAMPLE 7

$2 \times 10^8$ Mel 624 cells were infected with influenza A/UDORN as described in the protocol for Example 5. The infected cells and an equivalent number of control cells (uninfected) were treated with pH 3.3 iso-osmotic, citrate-phosphate buffer. The eluted peptides were fractionated by HPLC as described in Example 6. The individual melanoma-derived HPLC peptide fractions were lyhophilized to remove organic solvents and then resuspended in pH 7.4 HBSS. Aliquots of these fractions were then pulsed onto K4B (HLA-A2$^+$) B cell targets that had previously been labeled with $^{51}$Cr. The K4B cells were then allowed to express class I molecules by incubation of the targets at 37° C. for 1 hour. GL1 (anti-Flu M1 56–68 peptide-specific, HLA-A2 restricted) CTL were added to microculture wells of 96 well microculture dishes at an effector-to-target cell ratio of 1:1. The CTL's and targets were incubated for 4 hours at 37° C. in cytotoxicity assays performed as described in Example 1.

Figure 5:
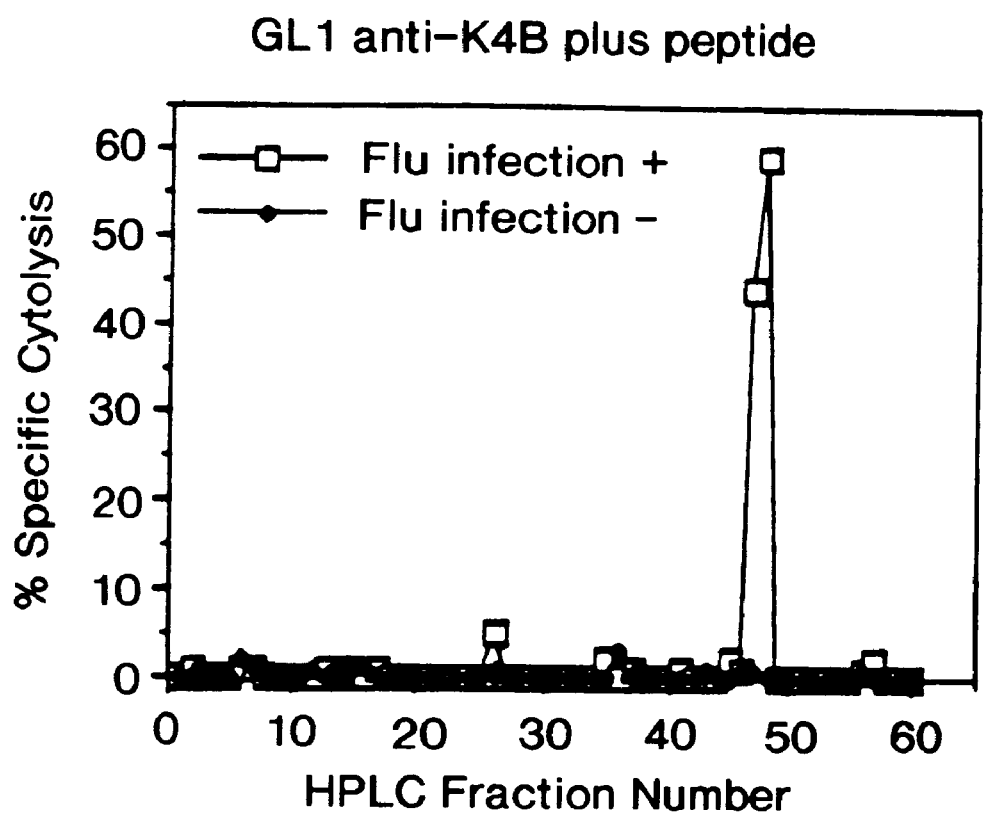
FIG. 5 is a graph showing the results of cytotoxicity assays in which iso-osmotic, pH 3.3 citrate-phosphate elution of influenza A/UDORN-infected Mel 624 cells was performed, the eluted peptides were fractionated by HPLC, the peptides from individual fractions were pulsed onto $^{51}$Cr-labeled K4B B cell targets, and GL1 CTL effector cells were added. Percent specific cytolysis as a function of HPLC fraction number is reported.

The results of these studies as shown in FIG. 5 are reported as percentage of specific K4B cytolysis. As can be seen, only K4B target cells that were incubated with peptides eluting in fractions 47 and 48 derived from influenza-infected Mel 624 cells were lysed by GL1 effector cells. The analagous fractions derived from uninfected Mel 624 cells were unable to confer susceptibility to GL1 CTL-mediated lysis on K4B target cells. The temporal co-elution of the synthetic Flu M1 57–68 peptide and the endogenously processed peptide derived from influenza-infected Mel 624 targets (recognized by GL1 CTL) in HPLC fractions 47/48 strongly suggests the identity of these peptide species. Additionally mass spectrometric analysis has showed that fraction 48 contained an endogenously processed peptide of molecular weight 968 having the sequence GXXGFVFTX (where X=I or L) (SEQ ID NOS: 2–5) which is completely consistent with the Flu M1 58–66 sequence.

The elution and identification of the endogenously processed, HLA-A2-presented Flu M1 58–66 sequence from HLA-A2$^+$ influenza virus-infected target cells indicates the feasibility and utility of using the present method for isolating and identifying other endogenously processed MHC-presented peptides.

The remaining examples in this section demonstrate that peptides eluted from class I molecules expressed by HLA-A2$^+$ melanoma cell lines according to the methods of the present invention contain tumor infiltrating lymphocyte (TIL) reactive T cell epitopes.

EXAMPLE 8

The tumor cell lines used were grown in T225 flasks in TCM and were maintained as described in Example 1. The metastatic melanoma cell lines included: Mel 397 (HLA-A2$^-$); Mel 526 (HLA-A2$^+$); Mel 624 (HLA-A2$^+$); Mel 392.A2 (an HLA-A2$^+$ transfectant of Mel 397 which was a gift, and available on request, from Dr. Yutaka Kawakami, NIH as described in Kawakami, Y., et al., *J. Immunol* 148:638 (1992), the disclosure of which is incorporated herein by reference); and WM35 (HLA-A2$^+$) which was a gift, and available on request, from Dr. M. Herlyn, Wistar Institute. The following EBV-transformed B cell lines were also used: K4B (HLA-A2$^+$), and the C1R series of class I transfectants C1R.A2, C1R.A3, C1R.Aw68, C1R.Aw69, C1R.B7, and C1R.Bw58. See, Storkus, W. J., et al., *Proc. Nat'l Acad. Sci. USA* 86:2361 (1989); Storkus, W. J., et al., *Proc. Nat'l Acad. Sci. USA* 88:5989 (1991); and Storkus, W. J., et al., *J. Immunol* 143:3853 (1989), the disclosures of which are incorporated herein by reference. The C1R transfectant cells express a class I molecule composition that is made up of approximately 90–97% of the transfected class I allele and 3–10% of the endogenous Cw4 allele.

Tumor infiltrating lymphocyte (TIL) lines were maintained in RPMI-1640 that was supplemented with 10% heat-inactivated human AB pooled serum (Gibco), the antibiotics used in TCM, and 6000 IU/ml rhIL-2 (Chiron). Oligoclonal TIL lines used in these studies were TIL 1074 and TIL 1128 which were provided by, and available on request, from Dr. Y. Kawakami, NIH, and the TIL E92-19 that was developed in the Immunologic Monitoring and Diagnostic Laboratory (IMDL) at the Pittsburgh Cancer Institute, and available on request. Each of these oligoclonal TIL lines (≧88% CD8$^+$) displayed HLA-A2 restricted, melanoma-specific cytotoxicity in 4 hour $^{51}$Cr-release assays.

Peptides were extracted from the melanoma cell lines as described in the previous examples. Briefly, melanoma cell lines were grown until they were approximated 80% confluent in T225 flasks with approximated 40–45×10$^6$ cells per flasks. TCM was then removed and the adherent monolayer of cells was washed 2–3 times with HBSS and removed by pipet, and 5 ml of pH 3.3 iso-osmotic, citrate-phosphate buffer was then added to the flasks, and the cells were incubated for 1 minute at room temperature. The peptide elution buffer solution containing the peptides previously bound to the class I molecules on the cell surfaces was harvested by pipet, centrifuged to remove any viable cells present and the resulting cell-free supernatant was stored at −70° C.

The treated cell monolayers were then briefly washed with 40–50 ml of serum-free TCM and then were decanted. The cells were recultured in 75 ml of TCM. The cells remained approximately 90–95% viable after treatment with peptide elution buffer and the cells regenerated their class I peptide complexes after an additional 10–18 hours of incubation at 30° C. The same flasks were routinely harvested for melanoma peptides on a daily basis by using the peptide elution buffer ("acid") elution protocol set forth herein. After 3–4 days, the cells were passaged ⅕ into new T225 flasks and the daily acid elutions were continued, resulting in multiple cell equivalents of class I-associated peptide being extracted from a single cell over the course of several days. In these studies, approximately $2 \times 10^9$ melanoma cells were repetitively stripped of their class I-associated peptides for 4 days and the resulting peptides were then fractionated. Day 2–3 yields of peptides resulting from stripping typically exceeded the day 1 yield by 9–116% as shown in Table 3.

TABLE 3

|   | Peptide Yield (µg) Per Day | % Day 1 Yield |
|---|---|---|
| Day 1 | 5.45 | 100 |
| Day 2 | 12.16 | 216 |
| Day 3 | 5.88 | 109 |
| Day 4 | 6.65 | 122 |

The daily buffer eluates that contained peptides derived from a single melanoma line were combined. The combined eluates were loaded onto $C_{18}$ SepPak devices as described above. The peptides were eluted from the columns by 1–2 ml of 60% acetonitrile in water and then lyophilized to remove the organic solvent. The samples were then reconstituted in 1 ml of pH 3.3 iso-osmotic, citrate-phosphate buffer and the reconstituted solution was fractionated on a Centricon-3 ultrafiltration device according to the manufacturer's protocol. The flowthrough from the Centricon-3 device consisted of peptides ≦3,000 Mr (approximately 30 amino acids in length) and the flowthrough was HPLC fractionated as described above. The solvents used for HPLC were A: 99.9% water/0.08% TFA, B: 99.94% acetonitrile/0.06% TFA. The gradients used in the HPLC were the following linear step intervals: isocratic A solvent for 0–5 minutes; 0% B (in A) to 10% B (in A) from 5–10 minutes; and 10% B (in A) to 35% B (in A) from 10–60 minutes. The flow rate used was 0.8 ml/minute and 0.8 ml fractions were collected. Individual HPLC fractions were lyophilized to remove organic solvents and then the fractions were reconstituted in 200 µl of HBSS and stored at −20° C. until the fractions were used in cytotoxicity assays.

Four or five hour cytotoxicity assays were performed as described above in Example 5. Briefly, melanoma cell lines were trypsinized, washed in TCM, pelleted by centrifugation, and labeled with 100 Ci of $Na_2{}^{51}CrO_4$ at 37° C. B cell lines were similarly pelleted and labeled with $^{51}Cr$. Labeled cells were washed twice with HBSS to remove unbound $^{51}Cr$ and the cells were then resuspended at $5 \times 10^4$/ml TCM. 100 µl of target cells were added to each assay well.

For peptide pulsing assays, 20 µl of individual HPLC fractions were added to wells containing $^{51}Cr$-labeled B cell target. The resulting peptide-target mixture was incubated for 1–2 hours at 37° C. to allow time for peptide charging of target cells. In those wells not receiving peptide, i.e., spontaneous release, experimental control, and maximal release wells, a 20 µl aliquot of TCM was used. 100 µl of TIL effector cells (5:1 effector-to-target ratio peptide-pulsing assays or various ratios from 20:1 to 5:1 for non-peptide pulsing assays) were added to assay wells and the contents of the 96 well plates were then incubated for 4 hours at 37° C. Spontaneous release wells received 100 µl TCM and maximum release wells received 100 µl of Triton X-100 (10% v/v in water). 100 µl of the resulting solution was harvested from each well and counted in a gamma-counter (LKB Pharmacia).

The results were reported in percent specific chromium release that was calculated as: % Specific Chromium elease= (Experimental cpm-Spontaneus cpm)/(Maximum cpm-Spontaneous cpm).

Spontaneous release was always less than 20% of the maximal release value. For some assays the assay results were reported in lytic units ($LU_{20}/10^7 EC$) based on 1 LU being equal to that number of TIL (EC (effector cells)) that were required to generate 20% specific lysis of the target.

The HLA-A2 status of all cell lines was assessed by indirect immunofluorescence assays as described above using the BB7.2 (anti-HLA-A2) monoclonal antibody and a fluorescein-labeled goat anti-mouse Ig (IgA+IgG+IgM) $F(ab')_2$ secondary reagent (Organon Teknika).

In the following example it is shown that treatment with peptide elution buffer according to the present invention diminishes melanoma class I expression and sensitivity to TIL.

EXAMPLE 9

$^{51}Cr$-labeled melanoma target cells (Mel 397 (HLA-A2⁻) and Mel 526 (HLA-A2⁺)) were treated with pH 3.3 iso-osmotic, citrate-phosphate buffer for 1 minute, neutralized with TCM, and used in 4 hour cytotoxicity assays with TIL 1128 effector cells. Alternatively, the buffer treated cells were neutralized and allowed to regenerate their class I-peptide complexes for 18 hours at 37° C. and the sensitivity to TIL 1128 was assessed in 4 hour cytolytic assays. The results are shown below in Table 4.

TABLE 4

| Target Melanoma | HLA-A2 (+/−) | Acid Treatment (+/−) | Culture for 18h past acid treatment (+/−) | TIL 1128 Lysis $LU_{20}/10^7$ EC |
|---|---|---|---|---|
| 526 | + | − | − | 168 |
|  | + | + | − | 8 |
|  | + | + | + | 152 |
| 397 | − | − | − | 14 |
|  | − | + | − | 4 |
|  | − | + | + | 12 |

As can be seen by the Table 4 results, acid treatment of the Mel 397 and Mel 526 target cells for 1 minute resulted in greater than 90–95% reduction of MHC class I molecule expression as monitored by the W6/32 (anti-class I monomorphic determinant), BB7.2 (anti-HLA-A2), or BBM-1 (anti-$\beta_2$-microglobin) MAb reagents and flow cytometry. As was to be expected, the level of class I complex denaturation rendered Mel 526 targets resistant to TIL 1128-mediated lysis in the 4 hour $^{51}Cr$-release assays. By comparison, Mel 397 (HLA-A2⁻) targets were not susceptible to TIL 1128 lysis under any conditions. Because the cells remained ≧90% viable after acid treatment, the targets were able to be recultured. Both class I expression (W6/32 reactivity) and sensitivity to TIL 1128 lysis returned to the control level by 18 hours in the Mel 526 targets, but not by 4 hours post-acid treatment, as demonstrated previously.

In the following example it is shown that the peptide buffer eluate resulting from treatment of melanoma target cells contains reactive peptide epitopes.

EXAMPLE 10

$10^8$ of each of Mel 397 (HLA-A2⁻), Mel 526 (HLA-A2⁻), and Mel 624 (HLA-A2⁺) cells were treated with iso-osmotic, pH 3.3 peptide elution buffer for 1 minute and the respective cell-free supernatants were collected. The individual supernatants were then desalted and concentrated on SepPak $C_{18}$ cartridges. The resulting peptides were then fractionated on Centricon 3 ultrafiltration devices in order to isolate peptides of molecular weight ≦3,000 Da. $10^6$ K4B cells (HLA-A2$^+$) B target cells were then incubated with either TCM or the bulk peptides from the Mel 397, Mel 526, or Mel 624 cells in TCM plus 100 μCi of $^{51}$Cr for 18 hours at 37° C. Mel 397, Mel 526, and Mel 624 target cells were also labeled for 1 hour with 100 μCi of $^{51}$Cr at 37° C. The target cells were then washed to free unbound peptides and examined for sensitivity to TIL 1074 and TIL 1128 (HLA-A2 restricted melanoma-specific) -mediated lysis in 5 hour cytolytic assays. The results of these studies are shown in Table 5 below.

TABLE 5

| Target Cell | HLA-A2 (+/−) | 18h incubation with peptides derived from: | TIL Reactivity TIL 1074 | $(LU_{20}/10^7 EC)$ TIL 1128 |
|---|---|---|---|---|
| K4B | + | — | 12 | 4 |
| K4B | + | Mel 397 (A2$^−$) | 21 | <4 |
| K4B | + | Mel 526 (A2$^+$) | 88 | 75 |
| K4B | + | Mel 624 (A2$^+$) | ND | 85 |
| Mel 397 | − | — | 10 | 6 |
| Mel 526 | + | — | 135 | ND |
| Mel 624 | + | — | ND | 85 |

ND = Not Done

As seen in Table 5, neither the TIL 1074 nor the TIL 1128 cells lysed the K4B control target cell line or the K4B target cells that were charged with peptides derived from the HLA-A2$^−$ Mel 397 tumor cell line. The K4B cells that were pre-incubated with peptides derived from the HLA-A2$^+$ melanoma targets (Mel 526 and Mel 624) however, were efficiently lysed by both TIL 1074 and TIL 1128 to a degree that was comparable to the parental Mel 526 and Mel 624 target cell lines. These findings support the hypothesis that TIL T cell epitopes were being eluted from HLA-A2 molecules that were expressed on the cell surface of melanoma cells by the pH 3.3 peptide elution buffer treatment.

In the following example the number and shared nature of HLA-A2-presented melanoma peptides were studied.

EXAMPLE 11

Figure 6A:
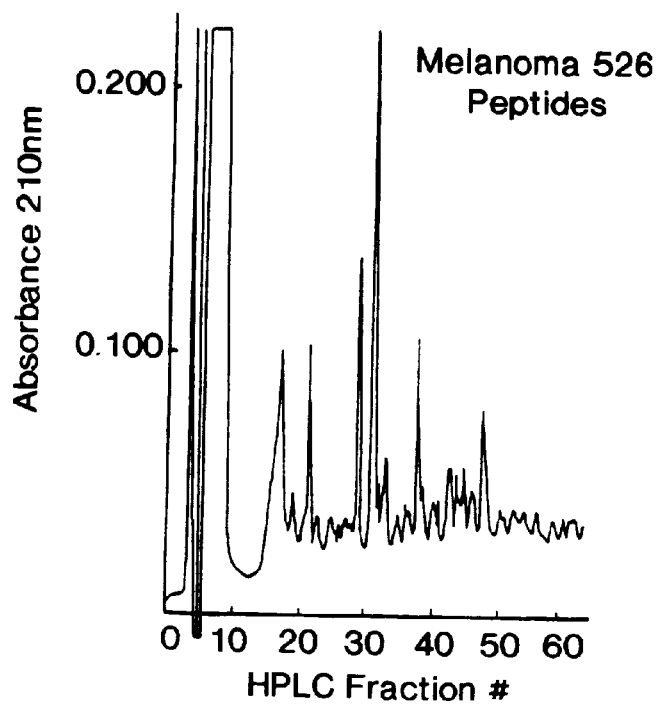
FIGS. 6A and 6B are RP-HPLC chromatograms of endogenously processed peptides that were eluted from Mel 526 (FIG. 6A) and Mel 624 (FIG. 6B) cells and monitored at 210 nm.
Figure 6B:
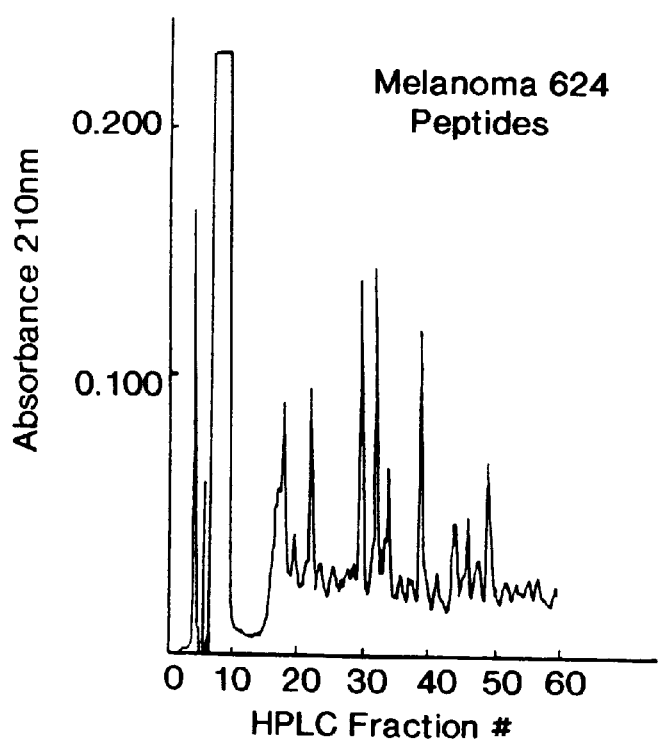
Figures 1, 7A:
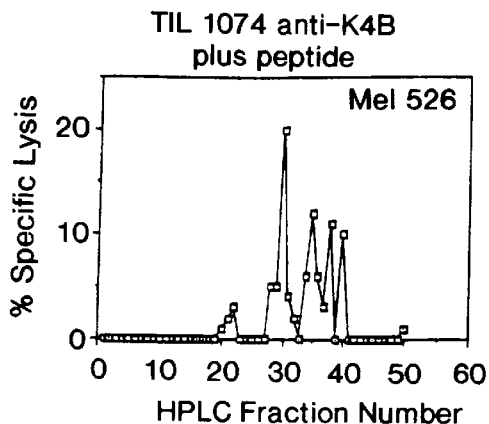
Figures 1, 7B:
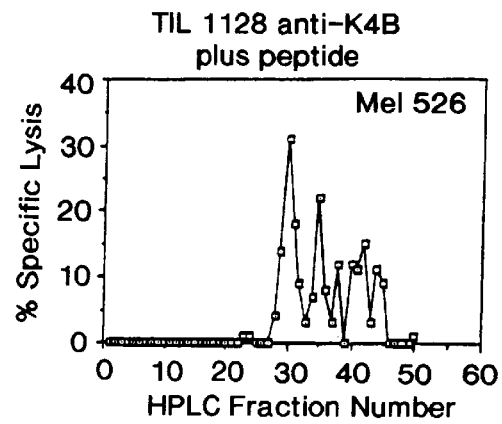
Figures 2, 7A:
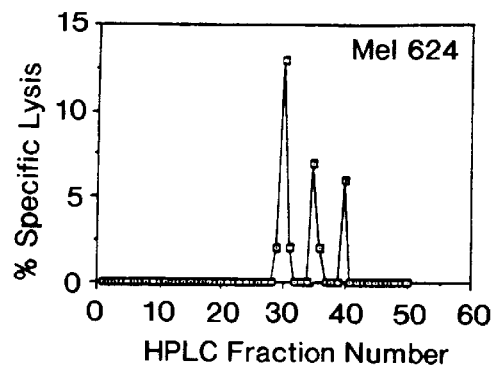
Figures 2, 7B:
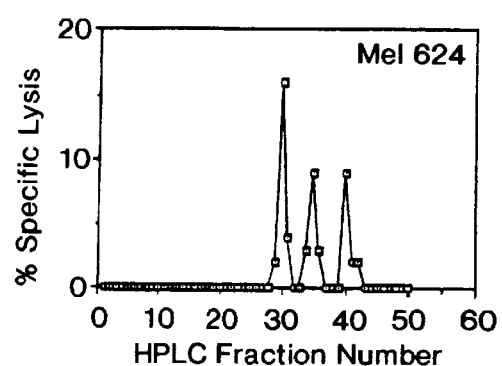
Figures 3, 7A:
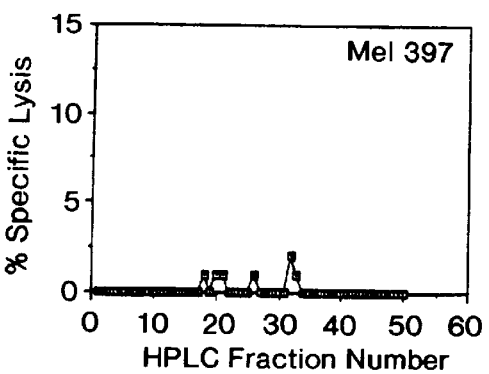
Figures 3, 7B:
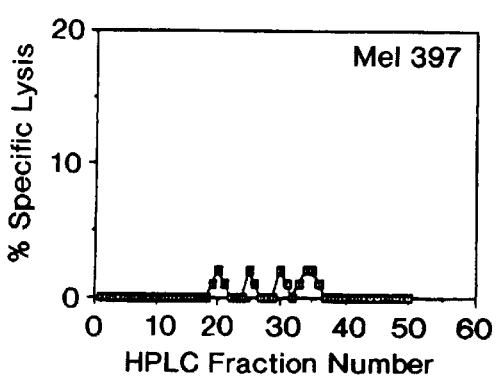

Peptides were eluted from 2×10$^8$ cells from the HLA-A$^+$ Mel 526 and 624 cell lines by treatment with pH 3.3 iso-osmotic, citrate-phosphate buffer for 1 minute at 37° C. as described previously. The treatments were repeated daily allowing the tumor cells to regenerate the class I-peptide complexes overnight. The approximately 2×10$^{10}$ cell equivalents of each peptide was obtained after 4 days. The eluted peptides were subjected to SepPak $C_{18}$ column chromatography and Centricon-3 ultrafiltration to select for peptides that were ≦3,000 Mr. Such peptides were then fractionated on RP-HPLC in a linear step gradient of 0%–35% acetonitrile (in water) monitored at 210 nm from water (containing 0.08% TFA) to 35% acetonitrile/64.93% water/0.07% TFA at a flow rate of 0.8 ml/minute. The results are shown in FIGS. 6A and 6B. Numerous peaks were identified based on absorbence at 210 nm for both cell lines.

The HPLC fractions from either Mel 526, Mel 624, or Mel 397 cells were then lyophilized to remove organic solvent, and resuspended in 200 μl of HBSS. 20 μl aliquots were used to pretreat $10^4$ previously $^{51}$Cr-labeled, washed K4B B cell targets (HLA-A2$^+$) in individual microwells of a 96-well U bottom assay plate and the solutions were incubated for 1 hour at 37° C. for peptide loading of HLA class I molecules. TIL 1074 or TIL 1128 effector cells (HLA-A2-restricted, melanoma-specific) were then added at an effector-to-target ratio 5:1. Five hour cytotoxicity assays were then performed.

The results which are shown in FIGS. 7A-1, 7A-2, 7A-3, 7B-1, 7B-2, and 7B-3 show there are six individual T cell epitopes (P1–P6) that were eluted from Mel 526 cells and which were recognized by TIL 1128 in TIL 1128-mediated cytolysis of K4B target cells in the following HPLC fractions: P1 (fraction 30); P2 (fraction 35); P3 (fraction 38); P4 (fraction 40); P5 (fraction 42); and P6 (fraction 44). Three of these TIL 1128-reactive peptides (P1, P2, P4) also appeared to be present in Mel 624 peptide preparations since Mel 624 HPLC fraction numbers 30, 35, and 40 contained peptides recognized by TIL 1128. Mel 397 (HLA-A2$^−$) HPLC fractions did not appear to contain any of the peptides significantly recognized by TIL 1128. In similar assays using TIL 1074, the TIL appeared to recognize P1–P4 derived from Mel 526 (but not P5 or P6); P1, P2, and P4 that were derived from Mel 624; but no HPLC fractions derived from Mel 397. No TIL reactive peptides could be demonstrated in HPLC fractions derived from acid extracted HLA-A2$^+$ B cell lines (data not shown). HLA-A2$^+$ B cells were not recognized or lysed by either TIL 1074 or TIL 1128 peptides derived from these cells and peptides derived from these cells are not recognized by these TIL.

In the following example it is shown that P1, P2, and P4 represent "shared" melanoma determinants.

EXAMPLE 12

In this example an additional HLA-A2 restricted (oligoclonal) TIL (E92–19 was included along with two additional HLA-A2$^+$ melanoma target cell lines, Mel 397.A2 (an HLA-A2$^+$ transfectant of Mel 397 available from Yataka Kawakami, NIH and described in Kawatami, Y., et al., J. Immunol. 148:638 (1992), the disclosure of which is incorporated herein by reference), and WM35 a gift of Dr. M. Hertlyn, Wistar and generally available. As shown below in Table 6 HPLC fractions derived from Mel 526 buffer extracts that contained TIL 1128 reactive epitopes (P1–P6) were incubated with $10^4$ K4B (HLA-A2$^+$) target cells that were previously incubated with $^{51}$Cr for 1 hour at 37° C. These peptide-pulsed targets were then used in 5 hour cytolytic assays with TIL 1074, TIL 1128, and TIL E92-19 effector cells. The results shown below in Table 6 were reported as (+) if TIL lysis of peptide-pulsed targets exceeded TIL lysis of TCM (control) treated K4B cells by more than 2 standard deviations. A pattern of TIL reactivity to P1–P6 was established as seen below.

TABLE 6

| | Bioactive HPLC Peak Fractions | | | | | |
|---|---|---|---|---|---|---|
| TIL | P1 (25) | P2 (30) | P3 (35) | P4 (40) | P5 (42) | P6 (44) |
| 1074 | + | + | + | + | − | − |
| 1128 | + | + | + | + | + | + |
| E92-19 | + | + | − | + | + | + |

As seen above, 3 out of 3 HLA-A2 restricted melanoma-specific TIL cell lines recognized P1, P2, and P4. TIL 1074 and TIL 1128, but not TIL 392–19, recognized P3. Only TIL 1128 recognized P5. TIL 1128 and TIL 392–19 but not TIL 1074, recognized P6.

In the following example a heterogeneous response to P1–PG to oligoclonal TIL populations was exhibited.

EXAMPLE 13

Peptides were extracted from $10^8$ cells of each of the following melanoma cell lines by iso-osmotic, pH 3.3 peptide elution buffer treatment: Mel 397, Mel 397.A2, Mel 526, Mel 624, and WM35. After extraction, the peptides from each cell line were individually subjected to fractionation on reverse-phase HPLC as described previously. The fractionated peptides were then lyophilized and reconstituted in HBSS as also described above. The individual fractions from the various cell lines were then pulsed onto $^{51}$Cr-labeled K4B targets for 1 hour at 30° C. TIL 1128 which were shown to recognize P1–P6 in Example 11 were then used as effector cells against these peptide-pulsed targets in 5 hour chromium release assays. In the results shown below in Table 7, peptides in HPLC fractions 30 (P1), 35 (P2), 38 (P3), 40 (P4), 42 (P5) or 44 (P6) that were capable of inducing K4B lysis greater than 2 standard deviations above the TCM control treated K4B target cells were denoted as (+)

TABLE 7

Expression of TIL 1128 reactive:

| Melanoma Line | HLA-A2 (+/) | P1 | P2 | P3 | P4 | P5 | P6 |
|---|---|---|---|---|---|---|---|
| Mel 397 | − | − | − | − | − | − | − |
| Mel 397.A2 | + | + | + | − | + | − | − |
| Mel 526 | + | + | + | + | + | + | + |
| Mel 624 | + | + | + | − | + | − | − |
| WM 35 | + | + | + | − | + | − | + |

These results show a heterogeneity at both the level of the melanoma cell line (peptide producer) and the oligoclonal TIL responder. Thus up to 4 TIL "clonal reactivity patterns" were determined. Pattern 1 recognized P1, P2, and P4. Pattern 2 recognized P3 only (present in TIL 1074 and TIL 1128, but not TIL E92–19.) Pattern 3 recognized P5 only (present in TIL 1128 only). Pattern 4 recognized P6 (present in TIL 1128 and TIL 392–19, but not TIL 1074). The pattern of P1–P6 expression by individual melanomas suggest that P1, P2, and P4 are coordinately expressed by all four HLA-A2$^+$ melanoma cell lines examined, including the HLA-A2$^+$ transfectant Mel 397.A2. When this observation is combined with the "clonotype 1" pattern of reactivity in 3 out of 3 oligoclonal TIL cell lines shown in Table 6, it is strongly indicated that P1, P2, and P4 represent shared HLA-A2-presented melanoma determinants. P3, P5 and P6 displayed more heterogeneous expression whereas P3 and P5 were expressed only by Mel 526. P6 was expressed by Mel 526 and WM35, but not Mel 397.A2 or Mel 624 cell lines.

These results indicate that P1, P2, and P4 may potentially be developed for vaccines as they appear to constitute immunodominant, shared melanoma peptides.

In the next example P1–P6 were analyzed for their ability to be presented in the context of diverse class I allotypes.

EXAMPLE 14

Figure 8A:
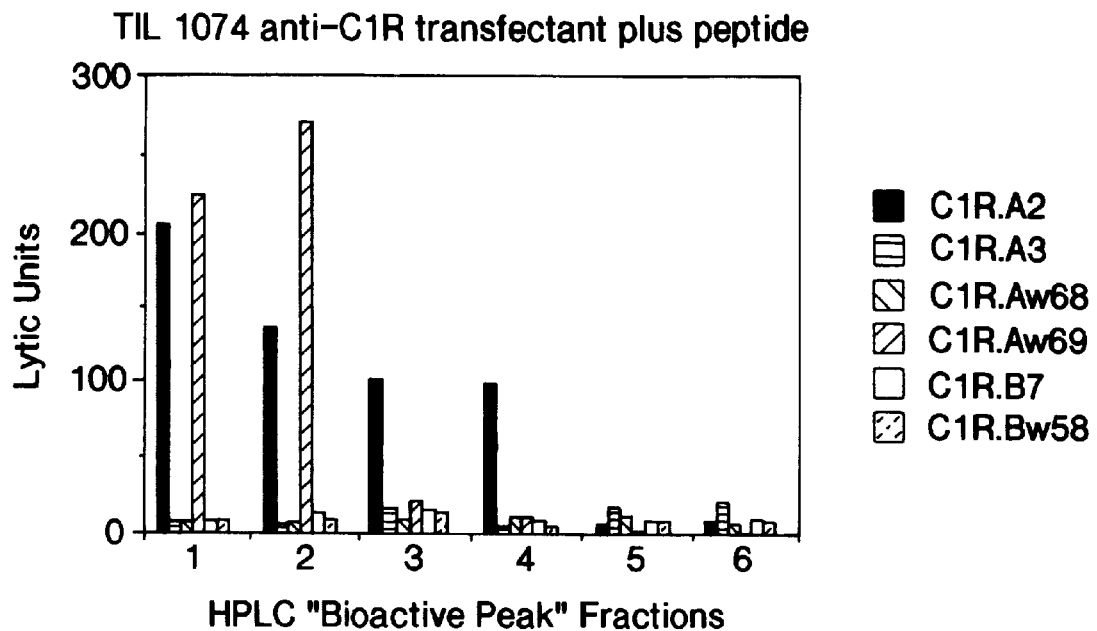
FIGS. 8A and 8B are graphs showing the ability of diverse class I allotypes (HLA-A2, -A3, -Aw68, -Aw69, -B7 and -Bw58) to present the six HPLC bioactive peak fractions (P1–P6) that were eluted from Mel 526 as measured by TIL 1074 (FIG. 8A) or TIL 1128 (FIG. 8B) mediated cytolysis of targets (C1R transfectants expressing various class I molecules (C1R.A2, C1R.A3, C1R.Aw68, C1R.A269, C1R.B7 and C1R.Bw58)). The lysis of each type of target cell is shown in lytic units for the peptides of each of the six HPLC fractions that were loaded onto each of the target cell types.
Figure 8B:
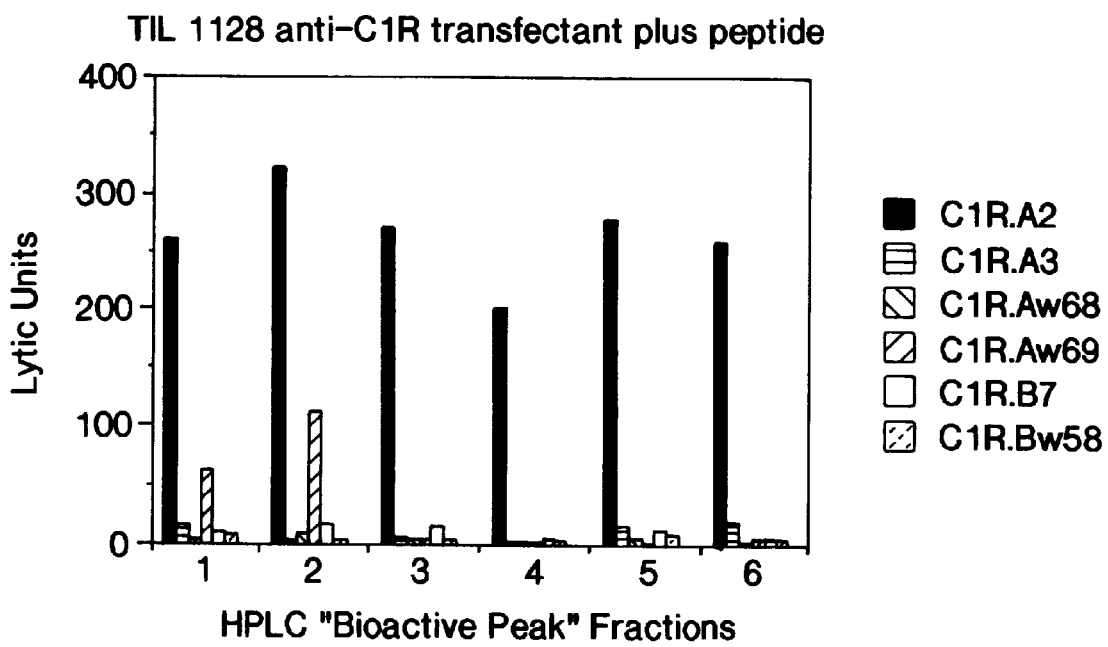

The HPLC fractions that were derived from Mel 526 that contained the six HPLC bioactive peak fractions P1–P6 (fractions 25, 30, 35, 40, 42, and 44, respectively) were pulsed at 37° C. for 1 hour onto $10^4$ $^{51}$Cr-labeled C1R transfectants that expressed essentially homogeneous populations of HLA-A2, -A3, -Aw68, -Aw69, -B7, or -Bw58 class I trans gene products. The peptide-pulsed target cells were then examined for sensitivity to TIL 1074- or TIL 1128-mediated cytolysis in 5 hour cytolytic assays. The results are shown in FIGS. 8A and 8B as Lytic Units ($LU_{20}/10^7$ EC).

It is seen that both P1 and P2 were efficiently presented by HLA-A2 (expressed by C1R.A2 targets) and HLA-Aw69 (expressed by C1R.Aw69 targets) to both TIL 1074 and TIL 1128. P3 and P4 were presented only by HLA-A2 cells to both TIL 1074 and TIL 1128. P5 and P6 were recognized by TIL 1128, but only in the context of HLA-A2. Other HLA class I molecules, HLA-A3 (expressed by C1R.A3), HLA-Aw68 (expressed by C1R.AW68), HLA-B7 (expressed by C1R.B7), and HLA-Bw58 (expressed by C1R.Bw58, were ineffective at presenting P1–P6 to either TIL line.

It has been shown in the art that synthetic peptide sequences corresponding to class I-presented, CD8$^+$ T cell-recognized peptides (T cell epitopes) are capable of both priming and restimulating CD8$^+$ cytotoxic T cells in vitro. See, for example, Wolfel, T., et al., *Immunogenet.* 26:178 (1987), the disclosure of which is incorporated herein by reference. Further, the length of peptide has been shown to be critical in determining the immunogenic potential of peptides in vitro and in vivo. Peptides 8 to 12 amino acids in length have been identified as the biologically relevant CD8$^+$ T cell recognized species and have been shown in the art to represent the optimal immunogen. See, for example, Rotzschke, O., et al., *Nature* 348:252 (1990), the disclosure of which is incorporated herein by reference.

In view of the above findings that melanoma-specific cytotoxic T lymphocytes define a minimum of six Class I-presented peptide epitopes common to most HLA-A2$^+$ melanomas, the following examples were carried out to further identify melanoma-associated epitopes that are presented by the HLA-A2 allele to T cells.

III. Methods—Identification of Melanoma T Cell Epitopes

Cell Lines

Two melanoma cell lines were used throughout this study. Mel 624 (HLA-A2, -A3, -B7, -B14; -Cw7; was obtained as identified above and Mel 9742 (HLA-A2; -A24; -B13, -B18; -Cw6, -Cw7; was obtained from the Instituto Nazionale Tumori, Milan, Italy), a gift, and available on request(Mel 9742 cell line was deposited with the American Type Culture Collection of 10801 University Blvd., Manassas, Va. 20110-2209 on Jan. 15, 1999 under ATCC accession number CRL-12641. Both cell lines were cultured in TCM consisting of RPMI-1640 media that was supplemented with 10% heat-inactivated fetal bovine serum, 100 IU/ml penicillin, and 100 µg/ml streptomycin (all reagents from Gibco BRL, Gaithersburg, Md.) and were otherwise cultured as described in Example 1.

The following CTL lines and clones that were derived from five different melanoma patients were also used in this study. The CTL clone A83 (autologous to Mel 9742) (kindly provided by Dr. G. Parmiani of Instituto Nazionale Tumori, Milan, Italy and available upon request) recognizes a common melanoma antigen and is restricted by HLA-A2 as reported by Anichini, A., et al., *J. Exp. Med.* 177:989 (1993), the disclosure of which is incorporated herein by reference. The tumor infiltrating (TIL) 1235 line and TIL 501.A42 clone were kindly provided by Dr. Y. Kawakami (National Institutes of Health, Bethesda, Md.), and available upon request. TILs 5403 and 6970 were isolated from metastatic melanoma lesions of HLA-A2$^+$ patients as described by Whiteside, T. L., et al., *J. Immunol Methods* 90:221 (1986), the disclosure of which is incorporated herein by reference. TILs 5403 and 6970 were cultured for 7 days in the presence of autologous tumor and were used directly as effector cells in cytotoxicity experiments. All of the TIL lines and clones were cultured in AIM-V media (Gibco BRL) that was supplemented with 10% heat-inactivated human AB serum (Gibco), and 300 IU/ml rhIL-2 (Cetus Corp., Emeryville, Calif.).

Acid Elution of MHC Class 1-Presented Melanoma Peptides (T Cell Epitopes)

Acid elution of, and reverse-phase high performance liquid chromatography (RP-HPLC) resolution of, melanoma peptides was performed as described above in Examples 1 and 6. Individual HPLC fractions that were obtained were lyophilized and reconstituted in 200 μl of Hank's buffered saline (Gibco BRL) and stored at −20° C. for use in the cytolytic assays. Alternatively, for mass spectrometric analyses, the eluted and fractionated peptides were lyophilized and reconstituted in 50 μl of 50% water and were then stored at −70° C. until they were used.

Reconstitution of T Cell Epitopes

In peptide-pulsing assays, 10 μl of peptides (in buffer) were added to microculture wells containing $10^4$ $^{51}$Cr-labeled T2 target cells (T2 cells were kindly provided by Peter Cresswell, Yale University, and are available upon request), 0.2 μg human β-microglobulin ($β_2$-m; Sigma Chemical Co., St. Louis, Mo.), and 0.2 μg MA2.1 (anti-HLA-A2.1 available from American Type Culture Collection, Rockville, Md. and described in McMichael, A. J., et al., *Hum. Immunol.* 1:121 (1980) the disclosure of which is incorporated herein by reference) monoclonal antibody in a total of 125 μl. Peptide loading was facilitated by the presence of the $β_2$-m and MA2.1 reagents as described by Zeh, H. J., et al., *Hum. Immunol.* 39:79 (1994), the disclosure of which is incorporated herein by reference. The cells were then incubated for 2 hours at room temperature. Effector T cells were then added at a 10:1 effector-to-target cell ratio (unless otherwise stated) and standard 4 hour cytolytic assays were performed as described in Example 5.

HLA-A2 Stabilization Assay

Various concentrations of synthetic peptides as noted below were incubated for 18 hours at room temperature with $10^6$ T2 cells (Salter, R. D., et al., *Immunogenetics* 21:235 (1985), the disclosure of which is incorporated herein by reference) 1 μg $β_2$-m, and 2 μg MA2.1 monoclonal antibody. The cells were then washed twice with buffered saline and stained with FITC-conjugated F(ab')$_2$ goat anti-mouse Ig (Organon Teknika, Durham, N.C.) for 30 minutes at 4° C. After two additional washes with buffered saline, the cells then were fixed with 4% formalin (Fisher Scientific Co., Pittsburgh, Pa.). The assays were monitored by flow cytometry that was performed on a FACScan flow cytometer (Becton Dickinson, Mountain View, Calif.) as described above with reactivity expressed in mean fluorescence channel (MFC) units. The results are reported as the percentage of increase over control of MA2.1 MFC number reactivity. Controls are represented by T2 cells cultured with $β_2$-m and MA2.1 monoclonal antibody, in the absence of synthetic peptide.

Mass Spectrometric Analysis

Mel 9742 HPLC fractions 47 and 48, obtained as described above, were pooled, lyophilized, and then reconstituted in 50 μl of 50% acetonitrile, 50% double distilled H$_2$O, and stored at −70° C. A 10 μl aliquot of this material was then introduced into an API III tandem mass spectrometer (PE-Sciex, Ontario, Canada) via the articulated ion-spray interface. The sprayer needle was held at 4,500 V with a coaxial sheath of nebulizing gas (compressed air) flow. Profile mass spectrums were obtained for peptide samples by scanning the first quadrupole from mass-to-charge (m/z) 500 to 1,600 in 3.37 seconds. The final spectrum was averaged from 10 scans. A mass spectra/mass spectra (MS/MS) product ion spectrum was obtained for the peptide species exhibiting m/z=941, hereinafter referred to as p939, by scanning the fragment ions resulting from collision with argon gas. The sequence was assigned as XXTVXXGVX (SEQ ID NOS: 6–37), where X=isoleucine or leucine, each with residue mass of 113.

Synthetic Peptides

The peptides used for these studies were synthesized using FMOC chemistry by the Peptide Synthesis Facility (Shared Resource) of the Pittsburgh Cancer Institute. Each synthesized peptide was purified to >95% homogeneity by reverse-phase (RP) HPLC. The identity of each peptide was confirmed by MS/MS. The following peptides were synthesized: p939/MART-1 32–40:ILTVILGVL (Ile-Leu-Thr-Val-Ile-Leu-Gly-Val-Leu) (SEQ ID NO: 38); gp100 280–288:YLEPGPVTA (Tyr-Leu-Glu-Pro-Gly-Pro-Val-Thr-Ala) (SEQ ID NO: 39) as described by Cox, A. L., et al., *Science (Wash. DC)* 264:716 (1994), the disclosure of which is incorporated herein by reference; HIV-nef 73–82:QVPL-RPMTYK (Gln-Val-Pro-Leu-Arg-Pro-Met-Thr-Tyr-Lys) (SEQ ID NO: 40) as described by Culmann, B. E., et al., *Eur. J. Immunol* 19:2383 (1989), the disclosure of which is incorporated herein by reference; influenza A matrix, Flu M1 58–66:GILGFVFTL (Gly-Ile-Leu-Gly-Phe-Val-Phe-Thr-Leu) (residues of 2–10 SEQ ID NO: 1); p53 186–196:DGLAPPQHLIR (Asp-Gly-Leu-Ala-Pro-Pro-Gln-His-Leu-Ile-Arg) (SEQ ID NO: 41) as described by Zeh, H. J., et al., *Hum. Immunol.* 39:79 (1994), the disclosure of which is incorporated herein by reference; and p53 264–272:LLGRNSFEV (Leu-Leu-Gly-Arg-Asn-Ser-Phe-Glu-Val) (SEQ ID NO: 42) also described by Zeh, H. J., et al.

In the following example, the specific recognition of HLA-A2-presented melanoma peptides by CTL Clone A83 is shown.

EXAMPLE 15

Melanoma 9742 (Mel 9742) and melanoma 624 (Mel 624) cells were treated as in Example 1 with peptide elution buffer (iso-osmotic, citrate-phosphate buffer at ph 3.3). Peptides were extracted from approximately 5×10$^9$ cell equivalents of each cell type. Specifically, 3 sequential daily treatments were used to obtain each of the particular peptides in this case with the cells being allowed to regenerate their class I-peptide complexes between peptide elution buffer treatments. These peptides were then resolved by RP-HPLC as described above. The respective peptides were lyophilized and each fraction was then reconstituted in 200 μl of buffered saline. 10 μl aliquots of the individual fractions were then pulsed onto the HL-A2$^+$ T2 cell line that had been labeled with $^{51}$Cr, in the presence of human $β_2$-m and the anti-HLA-A2 monoclonal antibody MA2.1. CTL were then added at an effector-to-target cell ratio of 2:1 for Clone A83 or 10:1 for TIL 1235 and Clone A42 and standard 4-hour cytotoxicity assays were then carried out. The results of these assays are shown in FIGS. 9A-1, 9A-2, 9B-1, 9B-2, 9C-1, and 9C-2 with % specific cytotoxity of the CTL shown as a function of the RP-HPLC fractions of Mel 624 (top panels) (FIGS. 9A-1, 9B-1, and 9C-1) and Mel 9742 (bottom panels)(FIGS. 9A-2, 9B-2, and 9C-2) -derived peptides. HPLC fractions 1–38 pulsed onto the T2 cell line were not recognized by any of the CTL.

Figures 1, 9A:
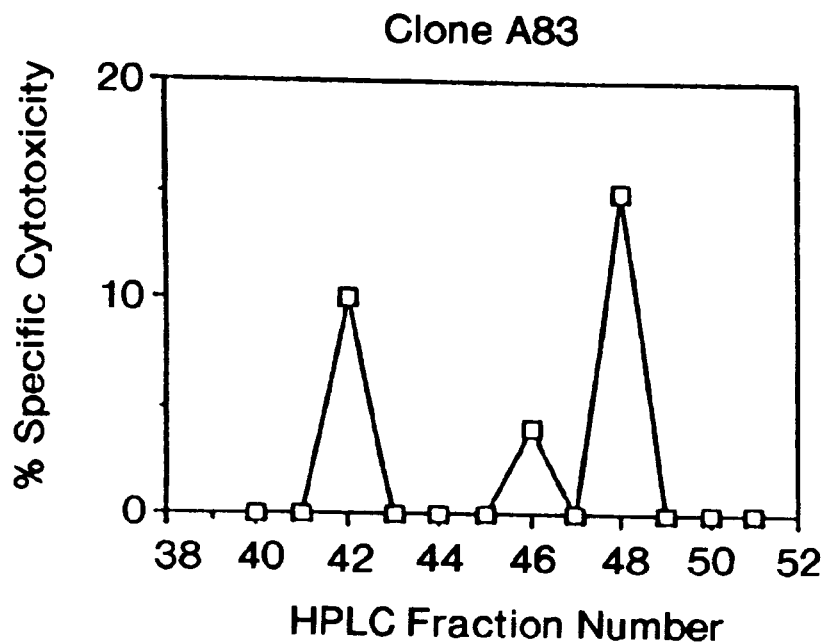
FIGS. 9A–9C are graphs showing the presence or absence of individual T cell epitopes that were eluted from two melanoma cell lines and then recognized by Clone A83 (FIGS. 9A-1 and 9A-2); TIL 1235 (FIGS. 9B-1 and 9B-2); or Clone A42 (FIGS. 9C-1 and 9C-2)—mediated cytolysis of T2 target cells. The percent of specific cytotoxicity is shown as a function of the individual HPLC fractions eluted from Mel 624 (top panels) or Mel 9742 (bottom panels) human melanoma cell lines according to the present invention.
Figures 2, 9A:
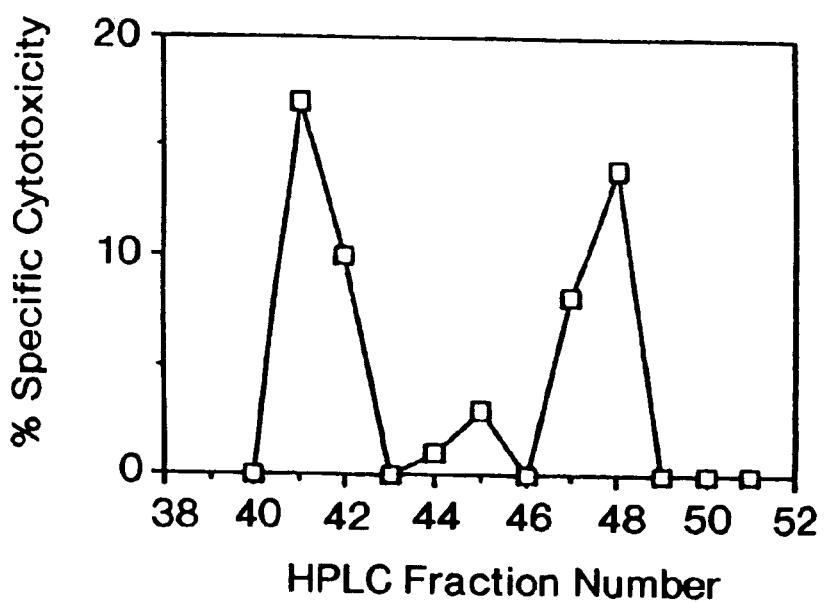
Figures 1, 9B:
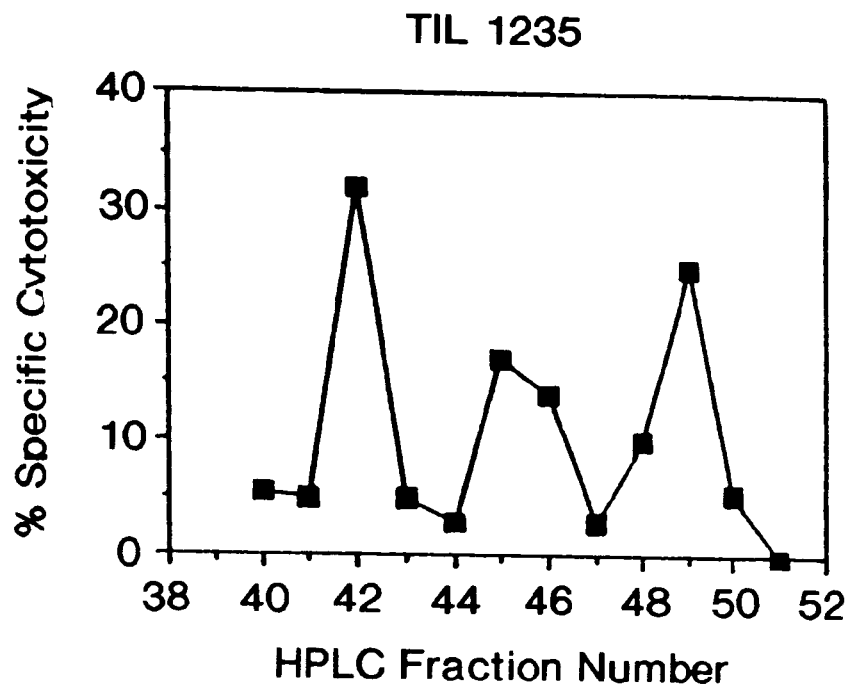
Figures 2, 9B:
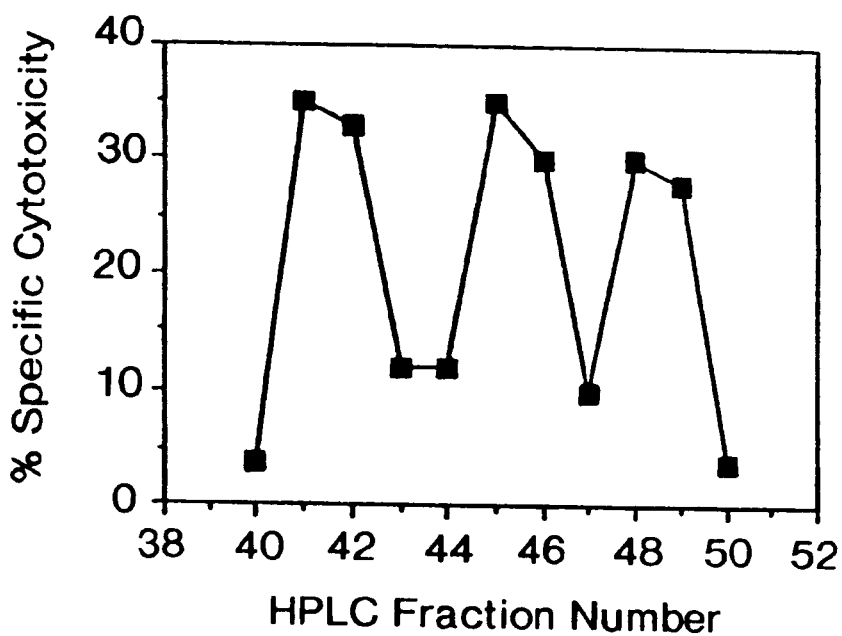
Figures 1, 9C:
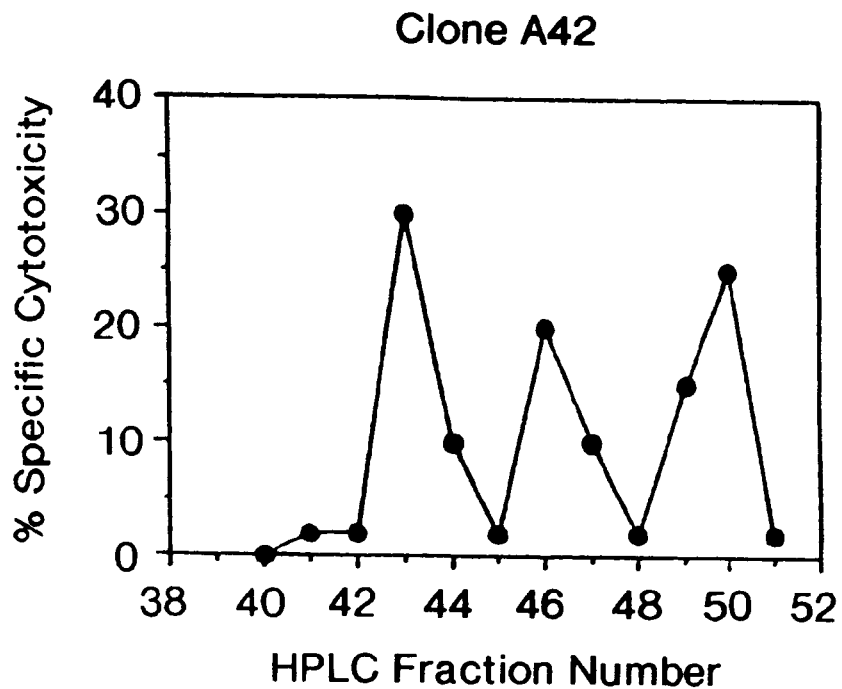
Figures 2, 9C:
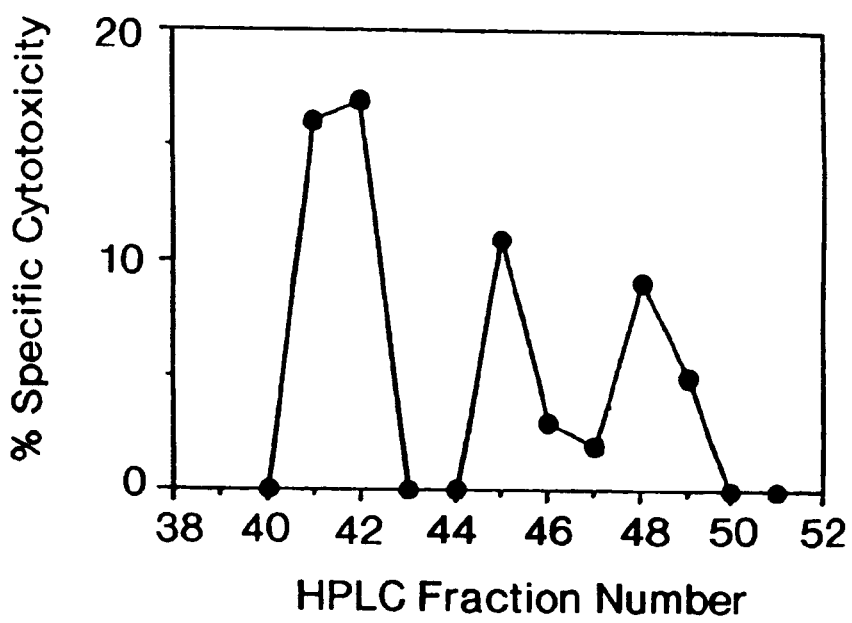

With respect to CTL Clone A83, three of the total of six bioactive peaks were identified for autologous Mel 9742 peptides, resolving in HPLC fractions 42–43, 45, and 47–48 as shown in FIG. 9A-2. A similar pattern of bioactive peaks was identified for allogeneic HLA-A2+ Mel 624 fractionated peptides as also seen in FIG. 9A-1. Peak 1 (HPLC fraction 42–43) and peak 3 (HPLC fractions 47–48) exhibited comparable efficacy in sensitizing the T2 target cell to lysis by CTL clone A83, with peak 2 (HPLC fraction 45) displaying a somewhat lesser capacity to do so.

HLA-A2 restricted, melanoma-specific TIL 1235 (FIGS. 9B-1 and 9B-2) and CTL clone A42 (FIGS. 9C-1 and 9C-2) also recognized these same A83-identified bioactive peaks as detected by cytolysis of T2 peptide-pulsed target cells, with peak 2 reactivity approximating that of peaks 1 and 3.

Thus, the foregoing shows that these melanoma TIL lines (Lines 1235 and 6970) and clones (Clones A83 and A42) coordinately recognize three predominant T cell epitopes as resolved by RP-HPLC. In the following examples, one of these three naturally processed melanoma peptides/T cell epitopes was identified.

EXAMPLE 16

Mel 9742 HPLC fractions 47 and 48 (peak 3 shown in FIGS. 9A-2, 9B-2, and 9C-2 were pooled and analyzed using tandem mass spectroscopy. 10 µl of fractionated material, corresponding to 20% of the pooled fractions acid eluted from $5 \times 10^9$ Mel 9742 cells, were injected into the triple quadrupole mass spectrometers electrospray ionizing source as described above. The summation of mass spectra for peptides with m/z=500–1,600 is shown in FIG. 10A. As can be seen, at least 39 different peptides were detected, with one peptide (m/z=941) representing the predominant species. Collision-induced dissociation (CID) was performed on the peptide where m/z=941 (p939) which yielded the daughter ion spectrum shown in FIG. 10B. The spectra was interpreted as defining a nine-amino acid peptide of $M_r$=939 with the sequence XXTVXXGVX (SEQ ID NOS: 6–37), where X=isoleucine or leucine (single letter amino acid designations). Since isoleucine and leucine exhibit identical masses ($M_r$=113), 32 potential variants of this peptide sequence are possible. The ultimately deduced and biologically relevant peptide p939 appears to derive from a recently cloned melanoma-associated gene Melan A according to the results of a search of the GenBank database that yielded a complete homology for one of these sequences, ILTVILGVL (Ile-Leu-Thr-Val-Ile-Leu-Gly-Val-Leu) (SEQ ID NO: 38). The complete Melan-A gene (accession number HSU06654) also known as MART-1, is described by Kawakami, Y., et al., *Proc. Nat. Acad. Sci. USA* 91:3515 (1994), the disclosure of which is incorporated herein by reference.

In the following example the binding affinity of p939 to HLA-A2 was determined.

EXAMPLE 17

The p939 deduced sequence ILTVILGVL (SEQ ID NO: 38) was synthesized and eluted in HPLC fractions 48/49, approximating the naturally processed bioactive form of p939 that was eluted from Mel 9742 as described above in the section on HLA-A2 stabilization assay. This peptide was then analyzed for its ability to bind to HLA-A2 using an HLA-A2-specific stabilization assay implementing the T2 cell line, as described by Zeh, H. J., et al., *Hum. Immunol.* 39:79 (1994) and Nijman, H. W., et al., *Eur. J. Immunol* 23:1215 (1993), the disclosures of which are incorporated herein by reference. The T2 cell line exhibits severely depressed cell surface class I expression resulting from a genetic lesion affecting peptide transport into the endoplasmic reticulum, as described by Salter, R. D., et al., *Immunogenetics* 21:235 (1985), the disclosure of which is incorporated herein by reference. T2 expression of class I molecules, in particular HLA-A2, at the cell surface can be enhanced by incubation of T2 cells at a reduced temperature in the presence of exogenous $\beta_2$-m and peptides that are capable of binding to the HLA-A2 allele as reported by Zeh, H. J., et al., Boyd, L. F., et al., *Proc. Natl. Acad. Sci. USA* 89:2242 (1992) and Bodmer, H. G., et al., *Nature (Land.)* 342:443 (1989), the disclosures of which are incorporated herein by reference.

Figure 11:
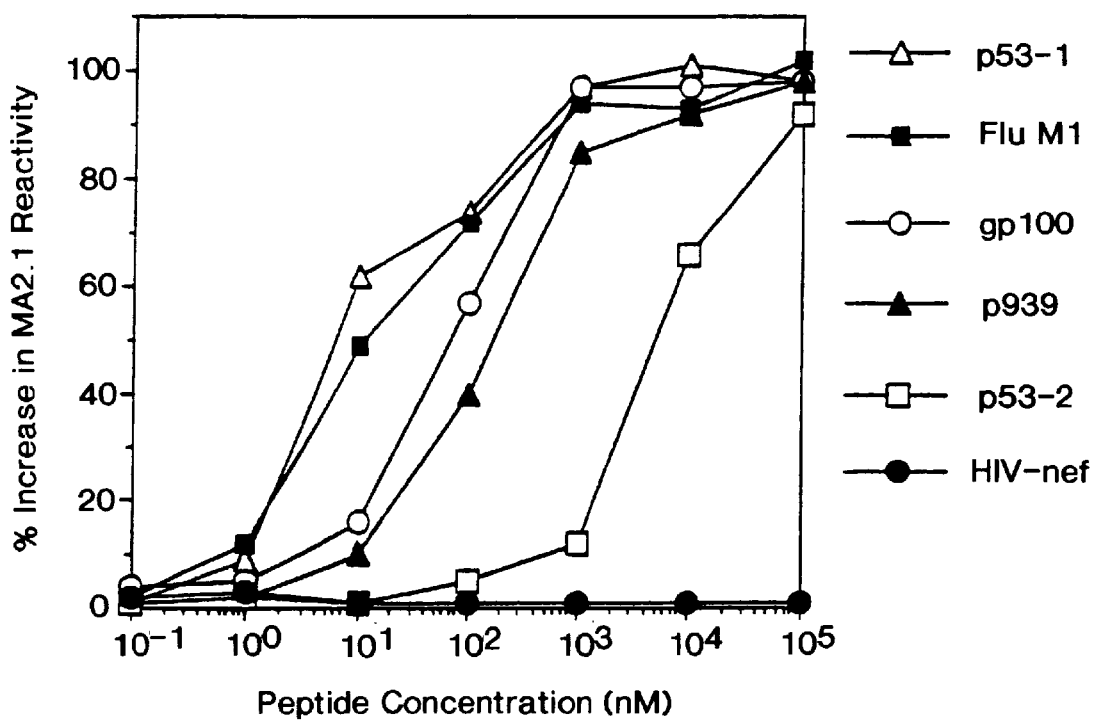
FIG. 11 is a graph showing the binding of peptide p939 to HLA-A2. HLA-A2 expression on the T2 cell line in the presence of increasing concentrations of various exogenous synthetic peptides including p939 was evaluated using MAb 2.1 (anti-HLA-A2 monoclonal antibody) in indirect immunoflourescent assays monitored by flow cytometry. ∆=p53-1; ■=Flu M1; ○=gp100; ▲=p939; □=p53-2; and ●=HIV-nef.

A panel of synthetic peptides, including p939, (p53-1; Flu M1 ; gp100; p939; p53-2; and NIV-nef) was incubated with the T2 cell line at room temperature (23° C.) for 18 hours and their capacity to stabilize HLA-A2 expression on the cell surface of T2 cells was evaluated using the MA2.1 (anti-HLA-A2 monoclonal antibody) in indirect immunofluorescence assays monitored by flow cytometry as described above (stabilization assay). Those peptides binding to HLA-A2 yielded an elevated reactivity with the MA2.1 (anti-HLA-A2) monoclonal antibody compared with non-peptide-treated or irrelevant peptide-treated T2 cells. By performing a peptide dose titration analysis (as described by Zeh, H. J., et al., *Hum. Immunol.* 39:79 (1994), the disclosure of which is incorporated herein by reference), a qualitative assessment of the relative binding capacity of each peptide for HLA-A2 was obtained. The results shown in FIG. 11 show that the Flu M1 58–66 (■) and p53 274–282 peptides (□) were quite effective in stabilizing HLA-A2 expression on the T2 cell line (half-maximal activity at ~5 nM), while the p939 peptide (▲) was less effective (half-maximal activity at ~200 nM). The efficacy of the p939 peptide was comparable to that observed for the gp100 280–288 peptide (○) which was recently identified by Cox, A. L., et al., *Science (Wash. DC)* 264:716 (1994), the disclosure of which is incorporated herein by reference, as a melanoma-associated, HLA-A2-presented T cell epitope. The gp100 280–288 peptide was similarly reported by Cox, A. L., et al., to bind HLA-A2 with intermediate-to-low affinity. As controls, the p53 186–196 (Δ) stabilized HLA-A2 very poorly and the HLA-A3 binding HIV-nef 73–82 peptide (●) did not stabilize HLA-A2, as previously reported by Zeh, H. J., et al., *Hum. Immunol.* 39:79 (1994).

A T cell epitope was generated by pulsing HLA-2+ cells with p939 in the following example.

EXAMPLE 18

Epitope reconstitution experiments using peptide p939 (SEQ ID NO: 38) were performed as described above in the section on reconstitution of T cell epitopes. Sensitization of T2 cells to lysis by antimelanoma CTL was evaluated over a wide range of peptide concentrations (250 nM-2.5 pM) as shown in FIGS. 12A–12D. Four different HLA-A2 restricted, antimelanoma CTL were evaluated in these studies: the bulk cultured TIL 1235 line (FIG. 12A), two CTL clones (A83 and A42) (FIGS. 12B and 12C, respectively), and the fresh TIL 6970 line. These melanoma-specific CTL were assayed in 4 hours cytotoxicity assays as described above at effector-to-target ratios of 10:1 against $^{51}$Cr-labeled T2 cells that were pulsed with p939 at the indicated concentrations. The lysis of T2 cells not pulsed with p939 was <5%.

Despite the apparent low affinity of p939 for HLA-A2, each of these four CTL recognized peptide-pulsed T2 targets. Interestingly, while half-maximal sensitization for lysis mediated by TIL 1235, clone A83, and TIL 6970 were reached at approximately 10 pM of peptide, the A42-clone required approximately 3,000 pM of peptide for half-maximal sensitization. TIL 1235 and CTL clone A42 recognition of p939-pulsed T2 targets also resulted in peptide-specific release of interferon-γ at p939 doses as low as 1 pM (data not shown). An additional HLA-A2-restricted fresh melanoma TIL 5403 was also able to recognize and lyse T2 cells pulsed with p939 peptide (data not shown). Evidence to support the presentation of p939 by HLA-2 was documented by the ability of the anti-HLA-A2 monoclonal antibody CR11-351 to inhibit cytolysis of T2 cells pulsed with p939 (data not shown).

As shown by the foregoing, the methods of the present invention have yielded identification of a naturally processed, melanoma-associated T cell epitope that is recognized by five district HLA-A2-restricted, tumor-specific CTL lines and clones. The p939 epitope is one of three epitopes coordinately recognized by two distinct antimelanoma CTL clones, A83 and A42 (derived from two different HLA-A2$^+$ patients).

One of the aspects of the present invention as demonstrated by the forgoing is that p939 identified herein possesses low affinity for HLA-2 and therefore appears to have more stringent requirements for presentation to T cells. As shown above in Example 18, epitope reconstitution was carried out in the presence of exogenous human $\beta_2$-m and MA2.1 (anti-HLA-A2 monoclonal antibody). These additions generally have been found to enhance peptide loading of various peptides into HLA-A2 complexes by 100–1000 fold. See, generally, Wolfel, T., et al., *Eur. J. Immunol* 24:759 (1994), Zeh, H. J., et al., *Hum. Immunol.* 39:79 (1994), Boyd, L. F., et al., *Proc. Natl. Acad. Sci. USA* 89:2242 (1992), and Bodmer, H., et al., *Nature (Lond.)* 342:443 (1989), the disclosures of which are incorporated herein by reference. Without these additions, there is only marginal CTL reactivity (5–10% over background) against p939-loaded T2 target cells. This requirement for $\beta_2$-m and MA2.1 appears to reflect the apparent low affinity of p939 for HLA-A2 in the assay system of the present invention. Currently this enhancement function appears to be unique to the MA2.1 antibody, but it is likely that other antibodies will have similar properties and will be within the scope of the present invention.

Despite this low affinity, enough p939 peptide was presented in HLA-A2 complexes on the cell surface of Mel 9742 cells to allow for CTL reactivity as well as to allow for p939 identification. p939 peptide appears to be efficiently processed and loaded into HLA-A2 molecules via the endogenous pathway in melanoma cells. p939 derived according to the present invention may therefore serve as an effective immunogen for cancer patients as a component of a peptide-based vaccine. ps IV. Methods—Therapy of Tumors with Tumor Peptide-Pulsed Dendritic Cells In the following section unfractionated, acid-eluted tumor peptides derived from tumors grown in vivo, preferably in conjunction with autologous dendritic cells ("DC") grown in recombinant IL-4$^+$ recombinant granulocyte macrophage-colony stimulating factor ("rIL-4+rGM-CSF") serve as a vaccine therapy for established tumors.

Despite the fact that some genes encoding specific melanoma-associated antigens recognized by CD8$^+$ T cells have been recently cloned and the relevant antigenic peptides have been identified, the vast majority of histologic subtypes of cancer express as yet undefined tumor epitopes. Further, an optimal host antitumor T cell response may require coordinate oligoclonal effector populations for the recognition of a broad spectrum of tumor epitopes rather than responses restricted to a single tumor-associated determinant. Recent data suggest that tumors can evade immune response directed against single T cell epitopes. Given such complexities, the following examples form an evaluation of unfractionated tumor-acid eluted peptides (containing multiple presumptive T cell epitopes) derived from autologous tumors of different histology and mouse strains presented in vivo by syngeneic bone marrow-derived DC ("BM-DC"). As will be demonstrated below, autologous/sygeneic DC loaded with acid-eluted tumor peptides can drive cellular immune responses in vitro and in vivo, leading to the suppression of growth or eradication of established tumors. In particular, a strength of the present invention allows one of skill in the art to design clinical protocols in which cancer patients may be treated with a vaccine comprising a composition of an immunologically effective amount of T cell epitopes derived from allogeneic but HLA-matched tumor of the same histologic type present in the patient by acid elution of the T cell epitopes from the tumor tissue.

Figure 16A:
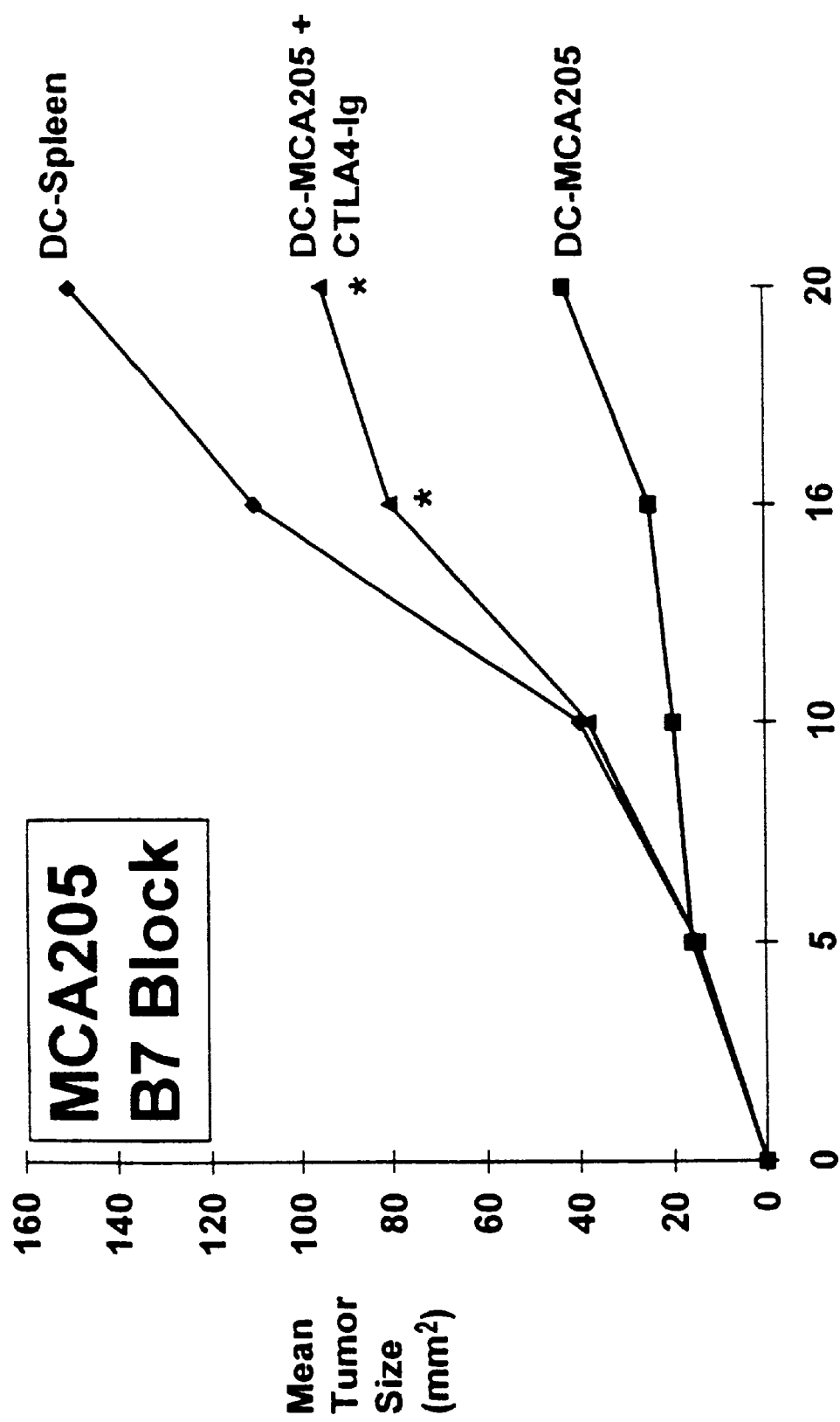
FIGS. 16A-16D show that the induction of an effective anti-tumor immune response by vaccines consisting of tumor peptide-pulsed DC requires both CD4+ and CD8+ T cells, functional costimulation of T cells mediated by the B7 molecule expressed by DC, and the cytokines IL-12, interferon-gamma and tumor necrosis factor-alpha. For the four figures, the mean tumor size±SE (five mice per treatment group) is depicted over time. The data depicted are representative of two experiments performed. Significant results compared to DC-MCA205 vaccine control group at 95% confidence (Fisher's exact test) are indicated with an asterisk (*).

Although the present method for eluting tumor-derived epitopes effectively extracts MHC class I-bound peptides from the tumor cells, it is likely that MHC class II-bound tumor peptides or cell-associated proteins may also be eluted. Indeed, each of the tumor cell lines evaluated expressed low to moderate levels of MHC class II when grown in vivo (data not shown). DC priming of class II-restricted antitumor immune responses appears to be supported by the ability to significantly reduce the therapeutic efficacy of DC-MCA205 in tumor-bearing animals by depletion of CD4$^+$ T cells as seen in FIG. 16D. CD4$^+$ T cells recognize MHC class II-presented peptides.

DC Isolation and Peptide Pulsing

Culture of BM-DC has been described by Zorina, T., et al., *J. Immunother.* 16:247 (1994) and Mayordomo, J. I., et al., *Nature Med.* 1:1297 (1995), the disclosures of which are incorporated herein by reference. Briefly, lymphocyte-depleted mouse bone marrow suspensions that were supplemented with two recombinant mouse cytokines, rmGM-CSF and rmIL-4 (1,000 IU/ml each) (Shering Plough Instit., Kenilworth, N.J.) ("DC media") for 5–8 days leads to the generation of large numbers (~10$^7$/mouse) of functional DC as defined by morphology, ultrastructure, phenotype, and strong mixed lymphocyte reaction-stimulating activity. The phenotype of BM-DC typically included high-frequency expression (60–95%) of CD45, CD44, CD11b, CD18, CD80, and CD86, as well as MHC class I and class II antigens.

Before being used in vaccines, DC were pulsed overnight with crude, unfractionated, acid-eluted peptides derived from relevant tumors or control syngeneic spleens. Peptide-pulsed DC were extensively washed and then irradiated (3,000 rads) before i.v. injection in the tail vein of tumor-bearing animals. In the fibrocarcinoma MCA205 and mammary adenocarcinoma TS/A tumor models, animals were injected three to four times, starting at day 4 or day 8 after tumor establishment and subsequently, every 4 days, with 3–5×10$^5$ DC pulsed with peptides. Alternatively, in the C3 tumor model, animals were injected on days 14, 21, and 28 after initial intradermal (i.d.) tumor inoculation.

Progressively growing tumors (MCA205 and C3 in C57BL/6 mice [B6, H-2$^b$] or TS/A in BALB/c [H-2$^d$] mice were surgically resected at day 20–25 (~150–250 mm$^2$ in size), and a single-cell suspension was obtained after brief enzymatic digestion (60 minutes) with DNase I (0.1 mg/ml; #776785; Boehringer Mannheim Corp., Indianapolis, Ind.), collagenase (1 mg/ml, 173 U/mg) in AIMV media (GIBCO-BRL, Gaithersburg, Md.). Viable cells (~1–5×10$^9$/cells)

were washed three times in HBSS (Gibco/BRL Laboratories, Gaithersburg, Md.), and the cell pellet was treated with mild acid buffer to allow for rapid isolation of tumor-associated peptides, as described above. Briefly, 10 ml of citrate-phosphate buffer, pH=3.3, was added at room temperature, and cell pellets were immediately resuspended by pipetting and then centrifuged for 5 minutes at 1,000 g. The cell-free supernatant was harvested, and peptides in acid-extracted supernatants were concentrated on activated SepPak C18 cartridges (Millipore Corp., Bedford, Mass.). The bound material was eluted with 2–3 ml of 60% acetontrile in water and lyophilized to near complete dryness (i.e., 20–50 µl). The peptides were then reconstituted in 1 ml HBSS (GIBCO-BRL) and stored frozen at −20° C. until used in DC-pulsing experiments. 1 million BM-DC were pulsed with peptides derived from $10^8$ to $10^9$ cells (tumor or spleen) in a total volume of 1–2 ml of DC media overnight at 37° C., 55 $CO_2$. Splenocytes freshly harvested from B6 animals were used as a cellular source of irrelevant peptides.

Tumor Cell Lines and Mouse Strains

Female 6–8-week old C57BL/6 [B6] and BALB/c [$H-2^d$] mice were purchased from The Jackson Laboratory (Bar Harbor, Me.). MCA205 ($H-2^b$), a gift, provided by S. A. Rosenberg (National Cancer Institute ("NCI"), Bethesda, Md.) and available on request, is a methylcholanthrene-induced fibrosarcoma established in B6 mice. TS/A ($H-2^d$) is a tumor cell line established by P. Nanni (University of Bologna, Bologna, Italy) from the first in vivo transplant of a moderately differentiated mammary adenocarcinoma spontaneously arising in a 20-month-old female BALB/c mouse (as reported by Nanni, P., et al., *Clin. ExP. Metastis* 1:373 (1983), the disclosure of which is incorporated herein by reference) and kindly provided as a gift by G. Forni, and available upon request (Immunogenetic and Histocompatibility Center, Turin, Italy). The meth A sarcoma is a methylcholanthrene-induced tumor established in $H-2^d$ mice, as described by Frassanito, M. A., et al., *Cancer Res.* 55:124 (1995), the disclosure of which is incorporated herein by reference. C3 is a tumor cell line obtained by transfecting C57BL/6 mouse embryonal fibroblasts with a plasmid containing the entire genome of the human papilloma virus type 16, as described by Porgador, A., et al., *J. Exp. Med.* 182:255 (1995), and Mayordomo, J. I., et al., *Nature Med.* 1:1297 (1995), the disclosures of which are incorporated herein by reference. All tumor cell lines were maintained in RPMI-1640 supplemented with 00% fetal bovine serum (Life Technologies, Inc., Grand Island, N.Y.), 2 mM L-glutamine, 100 U/ml penicillin, and 100 µg/ml streptomycin (Whitaker Bioproducts, Walkersville, Md.), referred to henceforth as "CM" (culture medium).

In Vivo Tumor Therapy Models

Twice the minimal tumorigenic dose of tumor cells ($2\times10^5$ MCA205, $10^5$ TS/A, or $2\times10^6$ C3) were injected intradermally ("i.d.") in the right flank of mice. Animals bearing day 4- to 8-established MCA205 or TS/A tumors were treated with three to four biweekly (every 4 days) intravenous ("i.v.") injections of $3-5\times10^5$ syngeneic BM-DC prepared as described above. Animals bearing day 14-established C3 tumors were treated weekly with syngeneic BM-DC ($3-5\times10^5$) pulsed with peptide. The mean tumor size was monitored biweekly. All experiments were performed two to three times using individual treatment groups of five mice. Mice were killed when tumors became ulcerated or when they reached a size greater than 250 $mm^2$.

Depletion Studies with Blocking Antibodies

CTLA4-Ig, a soluble fusion protein composed of the extracellular domain of the human CTLA4 receptor and the Fc portion of a human IgGI$C_x$chain has been previously described (Linsley, P. S., et al., *Science* (*Wash. DC*) 257:792 (1992), the disclosure of which is incorporated herein by reference) and was kindly provided as a gift by G. Davis, and is available upon request (Repligen Corp., Cambridge, Mass.). 50 µg of CTLA4-IgG1 was admixed with DC-MCA205 or DC-TS/A in vitro, and the mixture was then administered in the tail vein of tumor-bearing animals (three to four injections every 4 days). Mice treated with human IgG (Gamimmune, N. Miles Laboratories, Inc., Elkhart, Ind.) were used as controls. Hamster mAbs to mIFN-γ (H22) and mTNF-α(TN3 19.12) were prepared as reported by Sheehan, K. C. F., et al., *J. Immunol* 142:3884 (1989), the disclosure of which is incorporated herein by reference. The C17.8 (Wysocka, M., et al., *Eur. J. Immunol.* 25:672 (1995), the disclosure of which is incorporated herein by reference), a gift provided by M. Wysocka, The Wistar Institute, Philadelphia, Pa., and available on request, is an anti-mp40-IL-12-neutralizing mAb (rat IgG2a), which was administered i.p. (1 mg/mouse) 1 hour before the first two DC injections. The 11B11 (rat IgG2a) (Finkelman, F. D., et al., *P.N.A.S. USA* 83:9675 (1986), the disclosure of which is incorporated herein by reference) (hybridoma kindly provided, as a gift, by G. Shearer, NCI) is a neutralizing anti-mIL-4 mAb administered by i.p. injections of 300 µg/mouse 4 hours before and then 24, 48, and 72 hours after each of the first two DC injections. Anti-CD4 (clone GK1.5, rat IgG2b) (Wilde, D. B., et al.,*J. Immunol* 131:2178 (1978), the disclosure of which is incorporated herein by reference) and anti-CD8 (clone 2.43, rat IgG2b) (Sarmiento, M., et al., *J. Immunol* 125:2665 (1980), the disclosure of which is incorporated herein by reference) mAb (provided as a gift by M. Brunda, Hoffman-La Roche, Nutley, N.J., and available upon request) were injected i.p. on days 2 and 10 (1 mg/mouse/injection) after tumor inoculation. Depletion of $CD4^+$ and $CD8^+$ T cells was monitored by flow cytometry. Normal rat IgG was administered in negative control groups of animals.

In Vitro Cytokine Release Assays

Retroperitoneal lymph nodes (ipsi- and contralateral from the tumor) and the spleens of two mice per group, in two different experiments, were collected after three to four therapeutic applications (days 16–20). The cells were harvested after mechanical disruption of tissue in a culture dish, counted, and resuspended in CM+50 IU/ml rhIL-2 (Chiron, Emeryille, Calif.) at a final concentration of $1.5\times10^6$/ml. 200 µl of cells/well were cocultured with $10^5$ irradiated MCA205 (5,000 rads) in 96-well flat-bottomed plates. The plates were incubated for 24 hours (for C57BL/6 mice) or 36 hours (for BALB/c mice) at 37° C., 5% $CO_2$. The supernatants (100 µl) were harvested and assessed in commercial ELISAs for production of mIFN-γ and mIL-4 (Genzyme Corp., Cambridge, Mass.). The lower limit of sensitivity for each assay was 47 and 30 pg/ml, respectively.

Cytotoxicity Assays

YAC-1 (a gift of W. Chambers, University of Pittsburgh, Pittsburgh, Pa. and available on request), or the TAP-deficient T lymphoma RMA-S (kindly provided as a gift by H. G. Ljunngren, Massachusetts Institute of Technology, Cambridge, Mass., and available upon request) were pulsed with 10 µl of splenic or MCA205-derived peptides and labeled in CM containing $Na_2^{51}CrO_4$ (150 µCi/million cells) for 1–2 hours at 37° C., washed twice, and resuspended in CM at $2\times10^5$ cells/ml. MCA205 target cells were labeled in the same way. Equal volumes (100 µl) of target (admixed 1:10 with YAC-1 cold target provided to diminish nonspecific LAK activity) and effector cells (i.e., splenic cells after 5-day in vitro restimulation at effector-to-$^{51}$Cr-labeled-target ratios of 40:1 and 10:1) were plated in triplicate round-bottomed microtiter wells for 4 hours at 37° C., 5% $CO_2$. After a 4-hour incubation, 100 μl of supernatant was collected, and the percentage of specific $^{51}$Cr release was calculated using the following formula: percent $^{51}$Cr release=100×(cpm experiment−cpm spontaneous release)/(cpm maximum release−cpm spontaneous release), where spontaneous release was that obtained from target cells incubated with medium alone, and maximum release was obtained from target cells incubated in 5% Triton X-100 (Sigma Chemical co., St. Louis, Mo.). The specificity of tumor-directed cytotoxicity was evaluated by the addition of mAb specific for H-2K$^b$ (28-13- 35; American Type Culture Collection, Rockville, Md. ("ATCC")), H-2D$^b$ (28- 11-55; ATCC), and anti-mCD3 (29B; GIBCO-BRL).

Immunohistochemistry

Mice were killed by asphyxiation with $CO_2$ gas. Tissue from tumor sites was removed and placed in a cryomold filled with OCT-embedding medium (Miles Laboratories Inc.). Tissues were then snap-frozen by placing the mold on dry ice. Thin sections (5–7 μm) were cut by cryostat and placed on slides. Slides were stored at −80° C. or were immediately stained. Routine hematoxylin-eosin staining was performed on all tissues. Cryostat sections were fixed in cold acetone, hydrated in PBS, and incubated in protein-blocking solution (Immunon; Shandon-Lipshaw, Pittsburgh, Pa.) for 8 minutes. They were then incubated overnight at 40° C. with rat mAbs directed against mouse CD4 (TIB207; ATCC) and CD (TIB210; ATCC). Isotype-matched rat IgG was used as a negative control. Positive tissue controls consisted of frozen sections of spleens from BALE/c and B6 mice. After buffer washes, endogenous peroxidase activity was quenched with 0.6% $H_2O_2$ in methanol. Species-absorbed biotinylated mouse anti-rat F(ab')$_2$ (Jackson ImmunoResearch Laboratories, Inc., West Grove, Pa.) was applied to sections incubated with unlabeled primary Ab followed by treatment with streptavidin-peroxidase (Boehringer Mannheim Corp.) and 3'-amino-9-ethylcarbazole (Biomeda Corp., Foster City, Calif.). Sections were counterstained with hematoxylin and mounted in CrystalMount (Biomeda Corp.).

Statistical Analyses

Fisher's exact method was performed to interpret the significance of differences between experimental groups (presented as mean±SEM). Significance at 95% confidence limits are presented for individual experiments.

In the following example, autologous/syngeneic DC pulsed with acid-eluted peptides derived from syngeneic tumors markedly inhibited or erradicated tumor progression in mice bearing tumors.

EXAMPLE 19

Figure 13A:
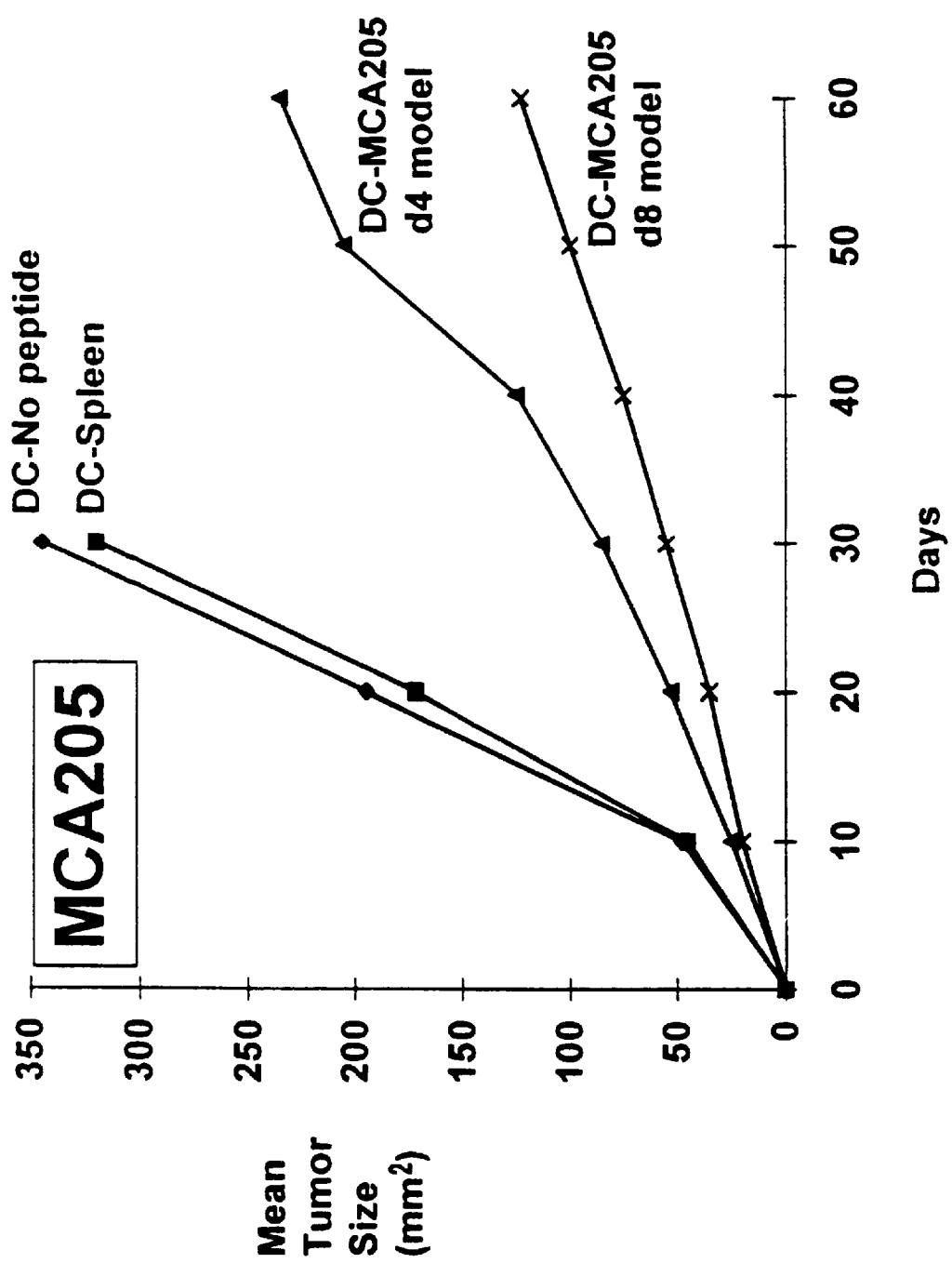
FIGS. 13A–13C show the effects of vaccines consisting of BM-DC pulsed overnight with unfractionated, acid-eluted peptides derived from either tumors or syngeneic spleen cells on tumor progression in mice. The tumor systems evaluated were the day 4–8 MCA205 fibrosarcoma (FIG. 13A), the day 5 TS/A mammary adenocarcinoma (FIG. 13B), and the day 14 C3 sarcoma (FIG. 13C) sub-cutaneous models. Tumor-bearing mice were given i.v. immunizations with syngeneic 5×10$^5$ BM-DC, beginning on the indicated days cited above, with repeat injections every 4 days, for a total of 3–4 immunizations in the MCA205 and TS/A models. Mice bearing day 14 C3 tumors were immunized every 7 days through day 35. Vaccines were prepared just prior to each vaccination by incubating syngeneic BM-DC with either relevant acid-eluted tumor peptides (DC-MCA205, DC-TS/A, or DC-C3, respectively, and are referred to in FIGS. 13A–13C as "DM-MCA205 d4 model"; "DC-TS/A" or "DC-C3", respectively) or control peptides obtained by acid-elution of normal syngeneic splenocytes ("DC-Spleen").
Figure 13B:
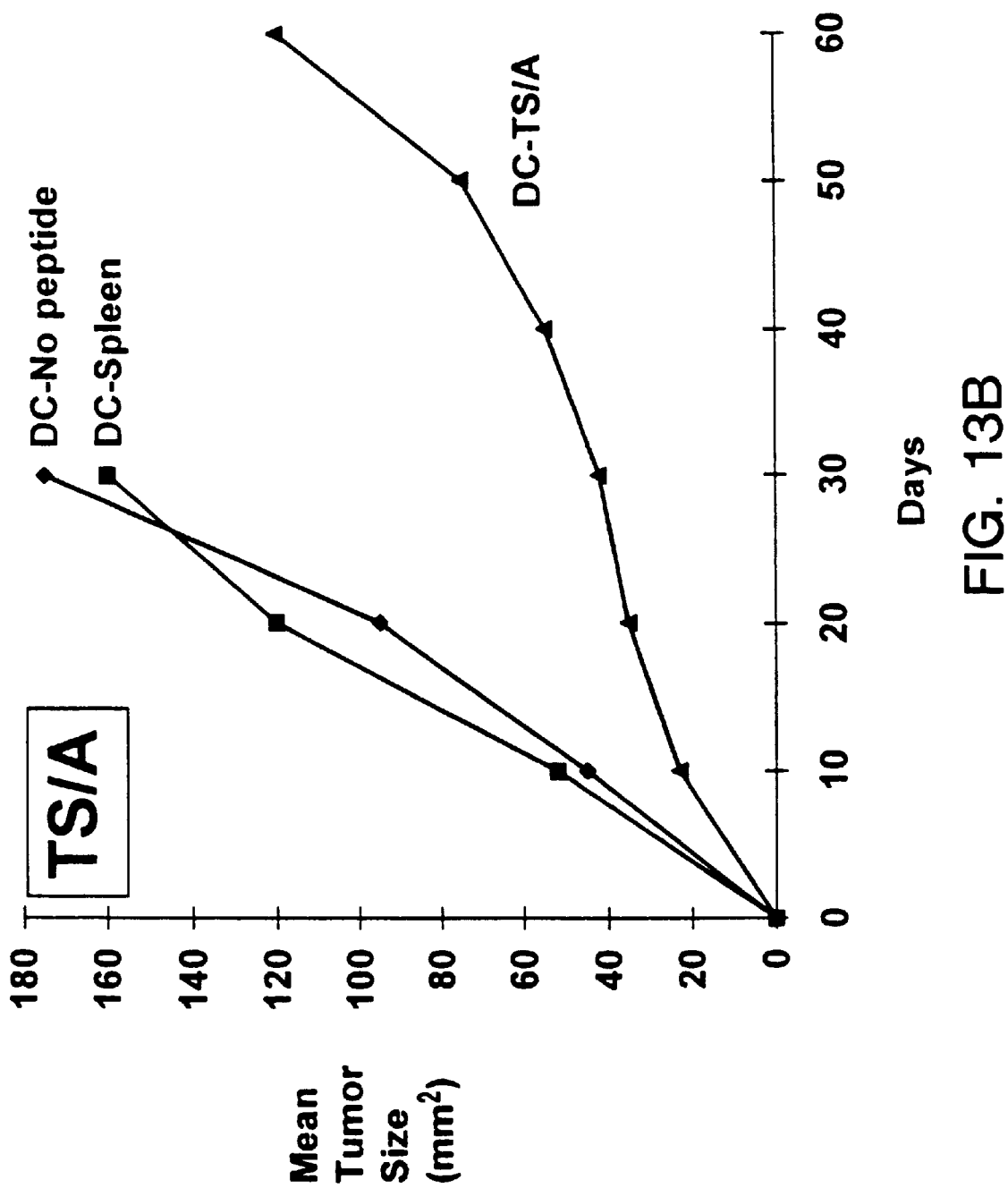
Figure 13C:
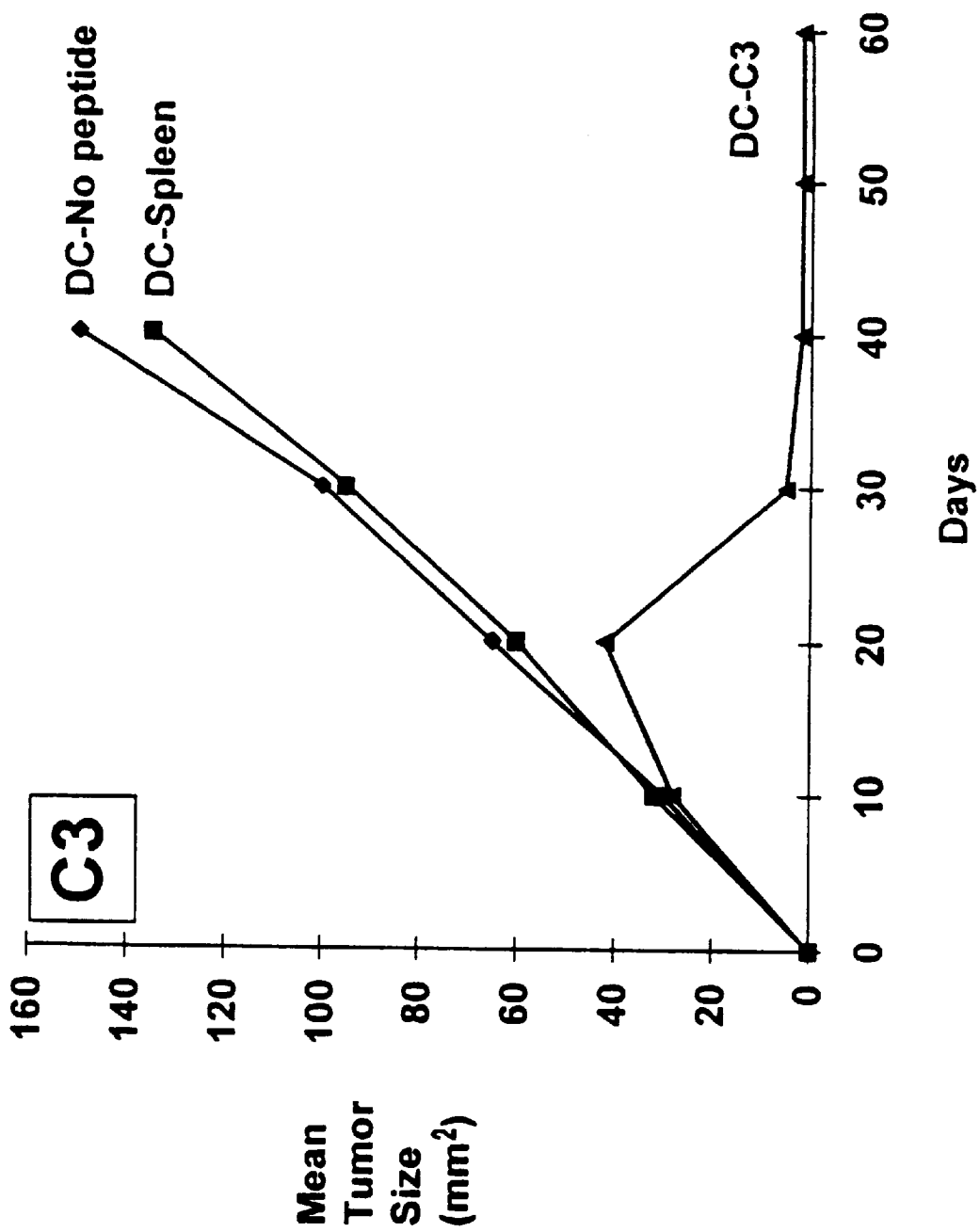

Twice the minimal tumorigenic dose of tumor cells MCA205 were injected i.d. in the flank of syngeneic C57BL/6 mice on day 0 as described above. 4–8 days later, animals bearing established tumors (~10–15 mm to 35 mm in size, respectively) were treated three to four times with biweekly i.v. administration of 3–5×10 irradiated BM-DC prepulsed with either unfractionated MCA205 tumor- or unfractionated B6 spleen-derived acid-eluted peptides as described above. As depicted in FIG. 13A, the mean tumor size in the day 4 established tumor group injected with DC pulsed with the relevant MCA205-derived peptides is significantly smaller than the control groups ("DC-No peptide"), or DC pulsed with splenic peptides ("DC-Spleen") at all therapeutic time points. Whereas no animals were tumor free after three immunizations, in most cases, the tumor growth was suppressed within 7 days after the first immunization. Indeed, the tumor size remained static for more than 6 weeks. Whereas control animals were sacrificed at day 20, animals receiving DC-tumor peptides therapy survived for 8–10 weeks. Most of these antitumor effects can be attributed to the first two DC immunizations (data not shown). MCA205 tumor growth was also markedly reduced when the first therapeutic injection of DC-MCA205 was started on day 8 as seen in FIG. 13A ("DC-MCA205 d8 model") and in FIG. 14B. Essentially identical results were achieved in the TS/A (H-2$^d$) established tumor model (mammary adenocarcinoma) in BALB/c mice as seen in FIG. 13B. In a sarcoma model (i.e., C3), shown in FIG. 13C, tumors established for 14 days were successfully treated with DC pulsed with unfractionated acid-eluted peptides administered on days 14, 21, 28, and 35. All DC-tumor peptide-treated animals exhibited complete and sustained tumor regressions.

In the following example, coadministration of low doses of systemic rmIL-12 modulated DC-mediated antitumor effects by enhancing the antitumor memory T cell response.

EXAMPLE 20

Figure 14A:
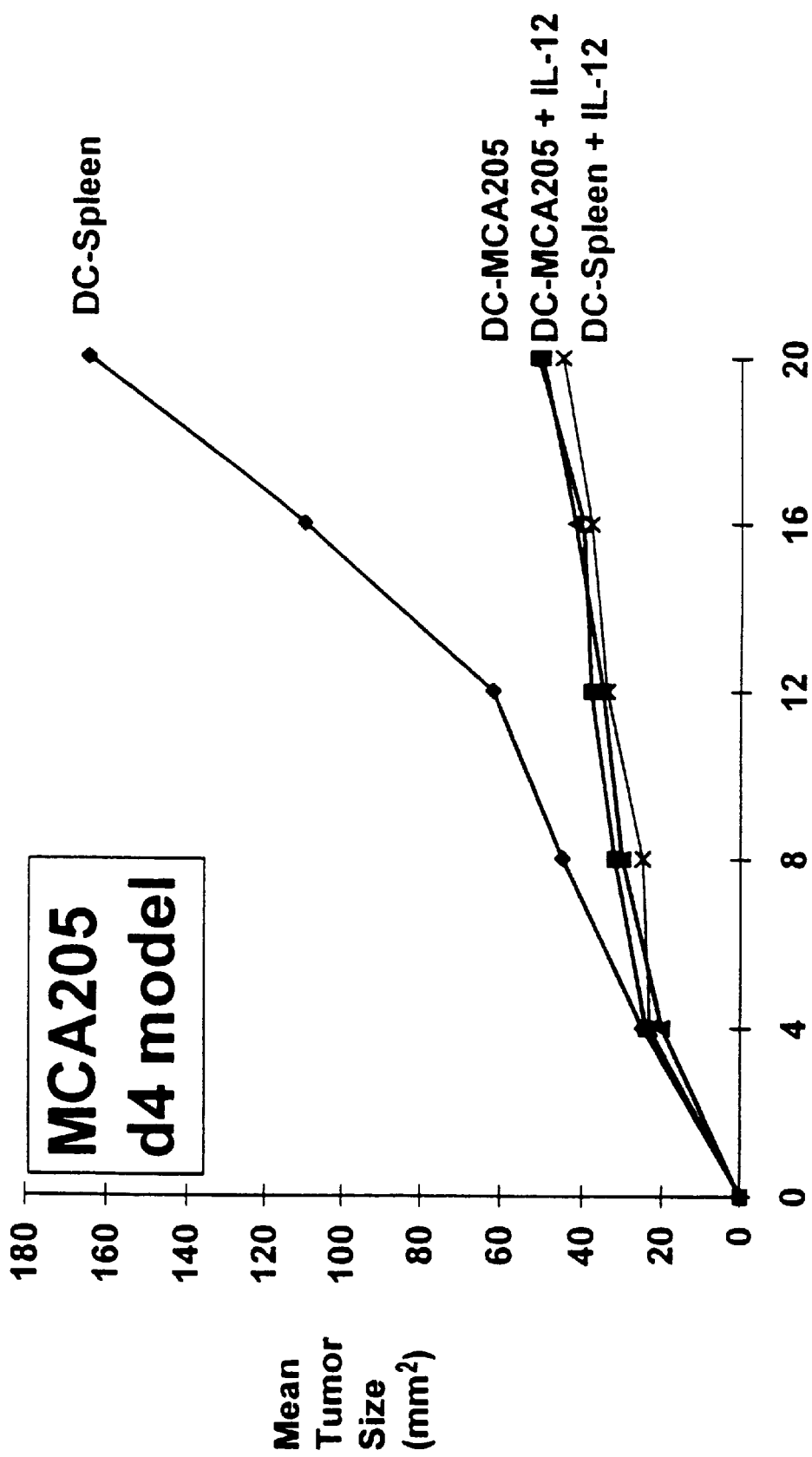
Figure 14B:
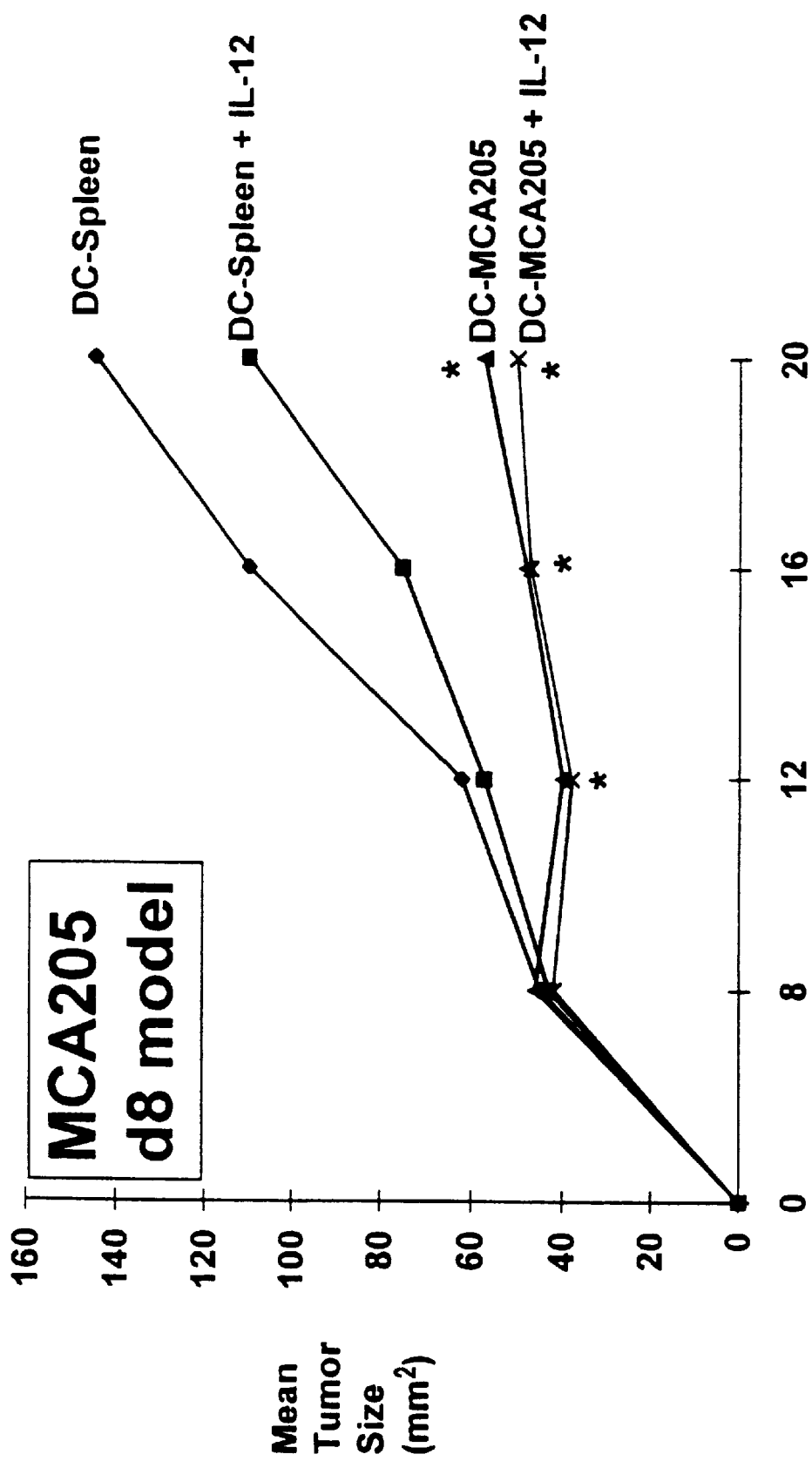

Macatonia, S. E., et al., *J. Immunol* 154:5071 (1995), the disclosure of which is incorporated herein by reference, recently reported that DC produce IL-12 and that DC direct the development of Th1 cells from naive CD4$^+$ T cells in vitro. This finding led to evaluation of whether concomitant systemic administration of low doses of rmIL-12 (100 ng provided i.p. every 4 days) would augment the efficacy of DC-tumor peptide therapy in the present in vivo models using poorly immunogenic tumors. As shown in FIGS. 14A and 14B, despite a beneficial therapeutic effect of rmIL-12 alone in day 4 (but not day 8) tumor models, the coadministration of IL-12 and DC-MCA205 did not result in a statistically significant improvement over groups of mice treated with DC-MCA205 alone, although the tumor growth curves were reproducibly slower for the DC-MCA205+rmIL-12 group in three independent experiments. However, DC-MCA205+rmIL-12 is significantly superior to administration of IL-12 alone±DC or DC pulsed with irrelevant splenic peptides for the treatment of established day 8 tumors as seen in FIG. 14B.

Figure 14D:
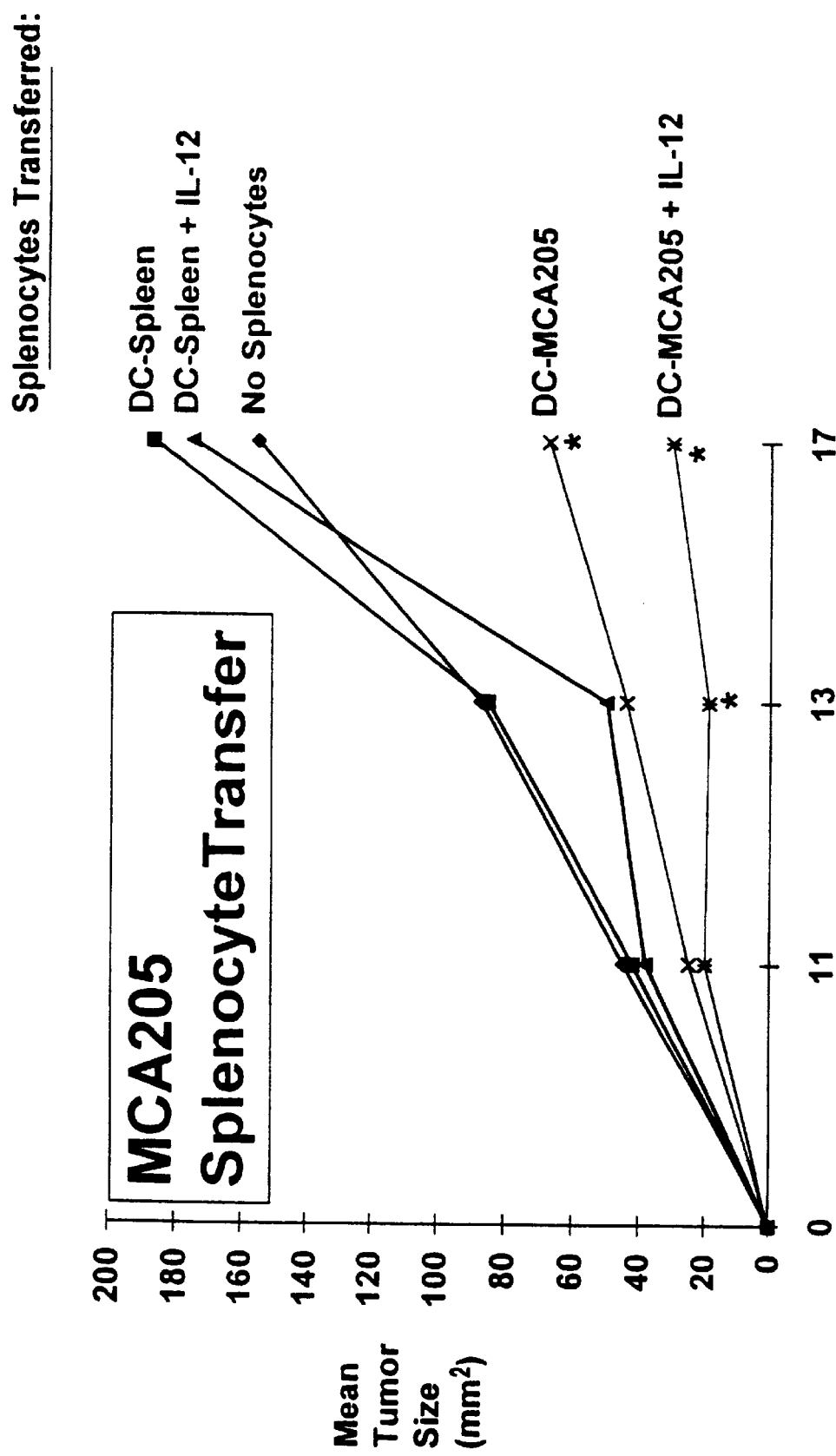

To verify that DC-MCA205-induced antitumor effects stem from the activation of the host immune system and to further evaluate the effects of combined IL-12 administration on the in vivo priming of T cells, adoptive transfer experiments were performed. Sera and/or spleens were obtained from day 16–18 treatment groups and injected into sublethally irradiated naive litter mates. As shown in FIG. 14C, neither pooled sera from mice immunized with DC alone or DC pulsed with splenic peptides (control groups), nor sera pooled from mice immunized with DC-MCA205 on day 4 or day 8 (from mice depicted in FIGS. 14A and 14B) were capable of transferring significant protective antitumor immunity. All mice were killed at day 15 with primary tumors greater than 250 mm$^2$ and demonstrable metastatic disease. Conversely, the transfer of 10$^7$ pooled, cryopreserved splenocytes derived from DC-MCA205 day 4 or 8 treatment groups was reproducibly capable of significantly slowing tumor growth in these naive syngeneic mice (FIG. 14D) compared with control groups. Interestingly, the survival was even more prolonged in the groups receiving splenocytes derived from tumor-bearing mice immunized with DC-MCA205 day 4/8+rmIL-12 compared with those mice immunized with DC-MCA205 on day 4 or 8 alone. There was no additional protective advantage of cotransferring sera along with splenocytes in these groups (data not shown).

It is concluded that DC pulsed with acid-eluted tumor peptides promote efficient cellular-mediated antitumor immunity and that coadministration of low doses of rmIL-12 may favor the priming of tumor-specific T cells. Analogous results were achieved in the TS/A model in BALB/c mice (data not shown). To test the specificity of the immune response elicited by the DC-TS/A, vaccine immunized animals were challenged with subcutaneous injections of $10^5$ TS/A (vaccine relevant) and $10^5$ meth A sarcoma cells (vaccine irrelevant). Tumor injections were applied to the opposite flank (to the vaccine site) of sublethally irradiated BALB/c mice. Whereas the growth of TS/A was inhibited by the adoptive transfer of cells derived from mice immunized with DC-TS/A, there was no impact of this treatment on the growth of the "irrelevant" meth A sarcoma (data not shown).

Figure 15A:
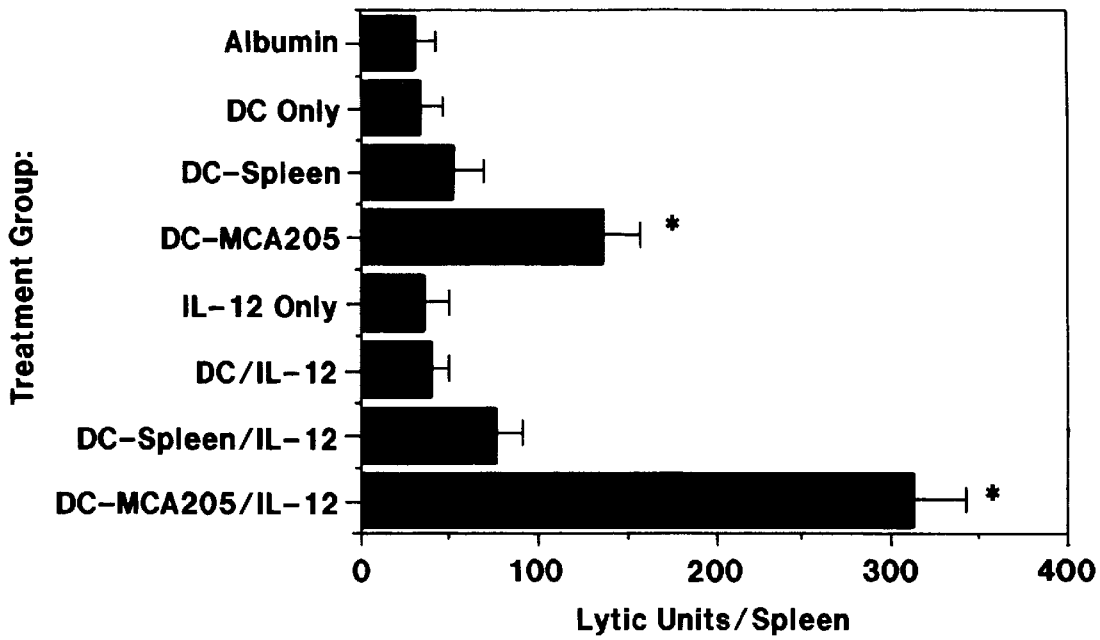
FIGS. 15A and 15B are graphs showing, respectively, the results of two studies evaluating the induction of tumor-specific cytotoxic T cells in mice immunized 3 times (FIG. 15A) or 4 times (FIG. 15B) with DC pulsed with MCA205 tumor-derived peptides DC-MCA205±rmIL-12 ("DC-MCA205/IL-12"; "DC-MCA205"), pulsed with normal spleen peptides (DC-Spleen)±rmIL-12 ("DC-Spleen/IL-12"; "DC-Spleen"), or pulsed with no peptides±rmIL-12 ("DC/IL-12"; "DC Only"). "Albumin" is a protein control that was injected alone. "IL-12 only" was injected alone. Two spleens per vaccine group were harvested and re-stimulated for 4–5 days with irradiated (10,000 rad) MCA205 tumor cells, before use as effector cells in 4-hour cytotoxicity assays against MCA205 tumor target cells. Significant results at 95% confidence levels (Fisher's exact test) are indicated by an asterisk (*).
Figure 15B:
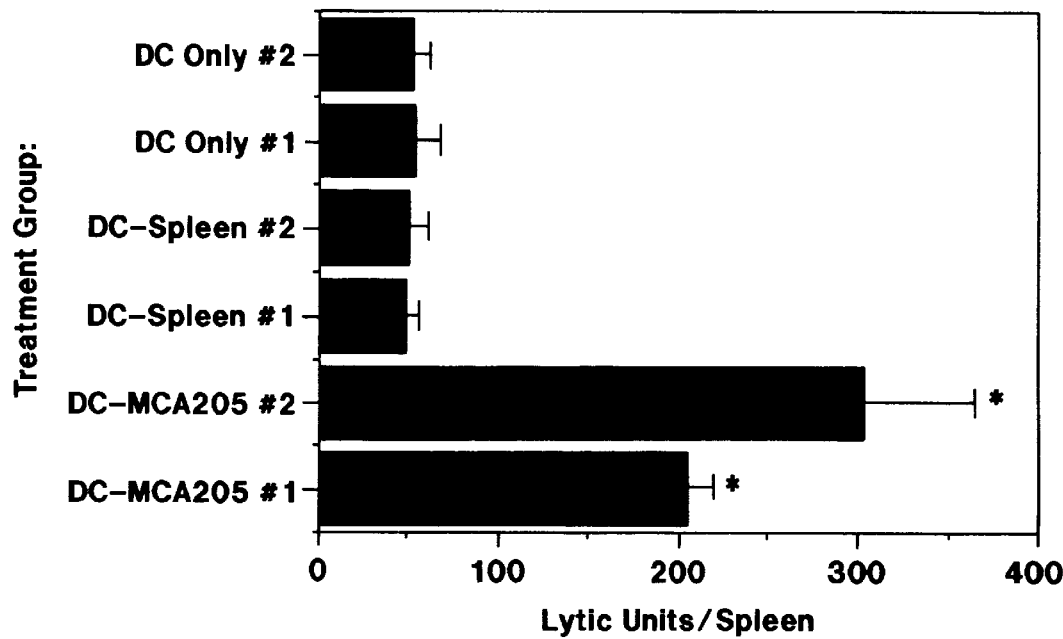

These in vivo results were reflected in in vitro studies quantifying the specific cytolytic activity of in vivo primed CTL present in the spleens of mice immunized three times with DC-MCA205 or DC-spleen+rmIL-12. Splenocytes were restimulated for 5 days in vitro with irradiated MCA205 tumors. After this restimulation, the splenocytes from mice immunized with DC-MCA205 and DC-MCA205+rmIL-12 displayed significantly elevated cytolytic reactivity against MCA205 (FIGS. 13A and 13B) that was inhibited 50–60% by anti-H-$2K^b$ and H-$2D^b$ antibodies or by anti-CD3 (data not shown). These effector cells did not lyse the murine LAK-sensitive target RMA-S. Splenocytes derived from mice receiving DC-MCA205+rmIL-12 typically displayed greater cytolytic reactivity than splenocytes from DC-MCA205 alone (FIGS. 15A and 15B).

In the following example, immunizations with DC pulsed with acid-eluted peptides enhanced cytokine release from the tumor-draining lymph nodes and in the spleen in response to tumor.

EXAMPLE 21

Since cellular immunity appeared to be critical in mediating antitumor effects, the pattern of cytokines released in an in vitro recall response to MCA205 tumor by cells derived from the retroperitoneal draining lymph nodes and from the spleens of DC-treated tumor-bearing mice was analyzed. The results are shown in Table 7 below. Freshly isolated mononuclear cells were cultured for 24 hours in vitro in the presence of MCA205 tumor. The culture supernatant was then analyzed by ELISA for levels of mIL-4 and mIFN-γ production. As expected, a Th1-associated response was observed, with a significant enhancement of mIFN-γ production in the DC-MCA205 treatment groups. It is also seen that levels of the Th2-associated cytokine IL-4 were also dramatically elevated in the same groups. In vivo administration of IL-12 did not significantly alter these in vitro results. Similar results were observed for lymphoid cells derived from TS/A tumor-bearing BALB/c mice. These results are shown in Table 8 below.

TABLE 7

| Groups | Mean Tumor size (mm$_2$) D23 | Nodes | | Spleens | |
|---|---|---|---|---|---|
| | | mIL-4* | mIFN-γ | mIL-4* | mIFN-γ |
| DC or DC-spleen | 145 ± 19 | 5 ± 1 | 0 ± 0 | 6 ± 1 | 643 ± 460 |
| DC or DC Spleen + IL-12 | 70 ± 20 | 10 ± 5 | 17 ± 12 | 6 ± 1 | 194 ± 90 |
| DC-MCA205 | 65 ± 10** | 162 ± 78** | 379 ± 226** | 79 ± 21** | 1,515 ± 143 |
| DC-MCA205 ± IL-12 | 48 ± 5§ | 24 ± 9§ | 1,1229 ± 702§ | 38 ± 5§ | 6,666 ± 760§ |

*pg/ml/2 × $10^6$ cells/24 hours in ELISA ± SE.
**Significant at 95% (Fisher's exact method) versus DC/DC spleen.
§Significant at 95% (Fisher's exact method) versus DC/DC spleen ± IL-12.
Retroperitoneal lymph nodes (ipsi- and contralateral from the tumor) and spleens of two mice per group, in two different experiments, were collected after three to four therapeutic applications (days 16–20). Cells were harvested and cocultured with $10^5$ irradiated MCA205 (5,000 rads) in 96-well flat-bottomed plates. Plates were incubated for 24 hours at 37° C., 5% CO$_2$. The supernatants were harvested and assessed in commercial ELISAs for production of mIFN-γ and mIL-4. Mice bearing day 4 MCA205 tumors were treated with either DC, DC pulsed with normal splenic acid-eluted peptides, or DC pulsed with acid-eluted MCA205 peptides. Identical treatment groups were also provided systemic rmIL-12 as indicated above. Due to lack of statistical difference between groups treated with DC alone and DC pulsed with acid-eluted splenic peptides (DC-spleen), and the same groups provided systemic rIL-12, their data were combined and mean SE are reported in this table.

TABLE 8

| Groups | Mean Tumor size (mm$_2$) D23 | Nodes | | Spleens | |
|---|---|---|---|---|---|
| | | mIL-4* | mIFN-γ | mIL-4* | mIFN-γ |
| DC or DC-spleen | 124 ± 45 | 32 ± 15 | 182 ± 106 | 224 ± 25 | 5,485 ± 1,502 |
| DC or DC Spleen ± IL-12 | 79 ± 20 | 31 ± 23 | 651 ± 432 | 237 ± 55 | 7,563 ± 468 |
| DC-TS/A | 27 ± 10** | 268 ± 104** | 5,000 ± 120** | 412 ± 80** | 15,000 ± 376** |
| DC-TS/A ± IL-12 | 0 | 316** | 9,000** | 273 | 15,000** |

*pg/ml/2 × $10^6$ cells/36 hours in ELISA ± SE.
**Significant at 95% (Fisher's exact method) versus DC/DC spleen/± IL-12.
Retroperitoneal lymph nodes (ipsi- and contralateral from the tumor) and spleens of two mice per group, in two different experiments, were collected after three to four therapeutic applications (days 16–20). Cells were harvested and cocultured with $10^5$ irradiated MCA205 (5,000 rads) in 96-well flat-bottomed plates. Plates were incubated for 36 h at 37° C., 5-% CO$_2$. The supernatants were harvested and assessed in commercial ELISAs for production of mIFN-γ and mIL-4. Mice bearing day 5 TS/A tumors were treated with DC-based therapies as outlined and reported in Table 1.

Semiquantitative reverse transcription PCR performed on snap-frozen specimens suggested that DC-MCA205 therapy results in upregulation of messages encoding mIL-4, mIL-5, mIL-10, mIFN-γ, and mp40-IL-12 in situ in the nodes of treated mice (data not shown). No discernible qualitative differences in cytokine production were noted between the ipsilateral nodes and their contralateral counterparts. In contrast to the modulation of cytokine messages in the lymphoid organs of DC-MCA205-treated animals, there was no marked difference in cytokines produced in situ within tumor lesions in mice derived from any of the treatment groups.

In the following example, costimulatory pathways and Th1-associated cytokines were evaluated for their involvement in the DC-mediated antitumor effects.

EXAMPLE 22

BM-DC cultures (5–8 days in IL-4+GM-CSF) express high levels of the costimulatory molecules CD80 and CD86 (Mayordomo, J. I., et al., Nature Med. 1:1297 (1995), the disclosure of which is incorporated herein by reference. Since costimulation of T cell-mediated antitumor immunity is critical for tumor rejection in vivo (Zitvogel, L., et al., Eur. J. Immunol 26:1335 (1996), the disclosure of which is incorporated herein by reference), the role of these costimulatory molecules in the DC-MCA205-mediated antitumor effects was investigated by admixing and coinjecting DC-MCA205 with the chimeric fusion protein CTLA4-Ig i.v., which functionally blocks CD28/CTLA4-mediated T cell costimulation. As depicted in FIG. 16A, CTLA4-Ig administration markedly reduced the antitumor therapeutic impact of DC-MCA205 treatment, such that it was no longer statistically significant versus control groups.

Figure 16B:
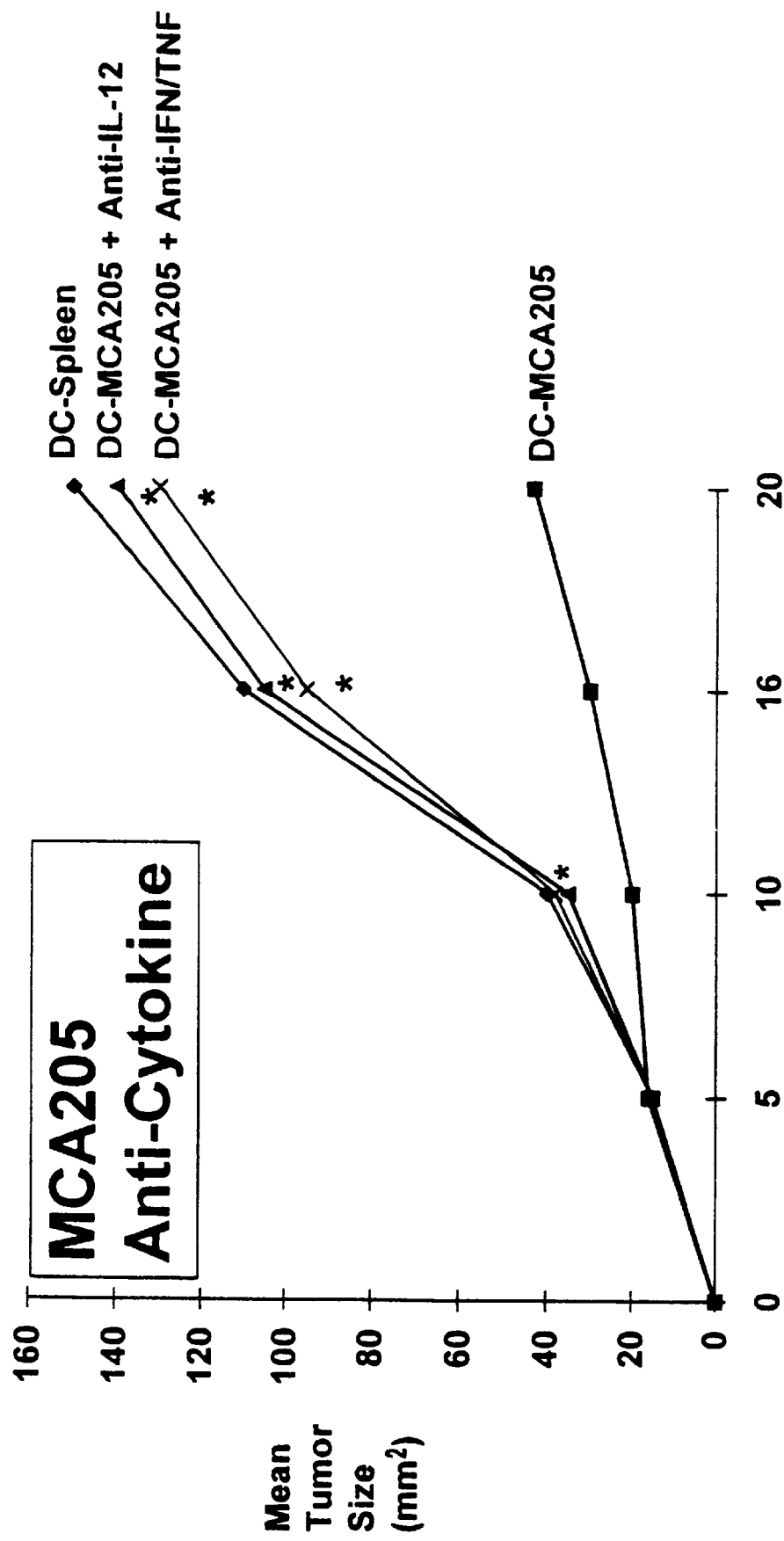
Figure 16C:
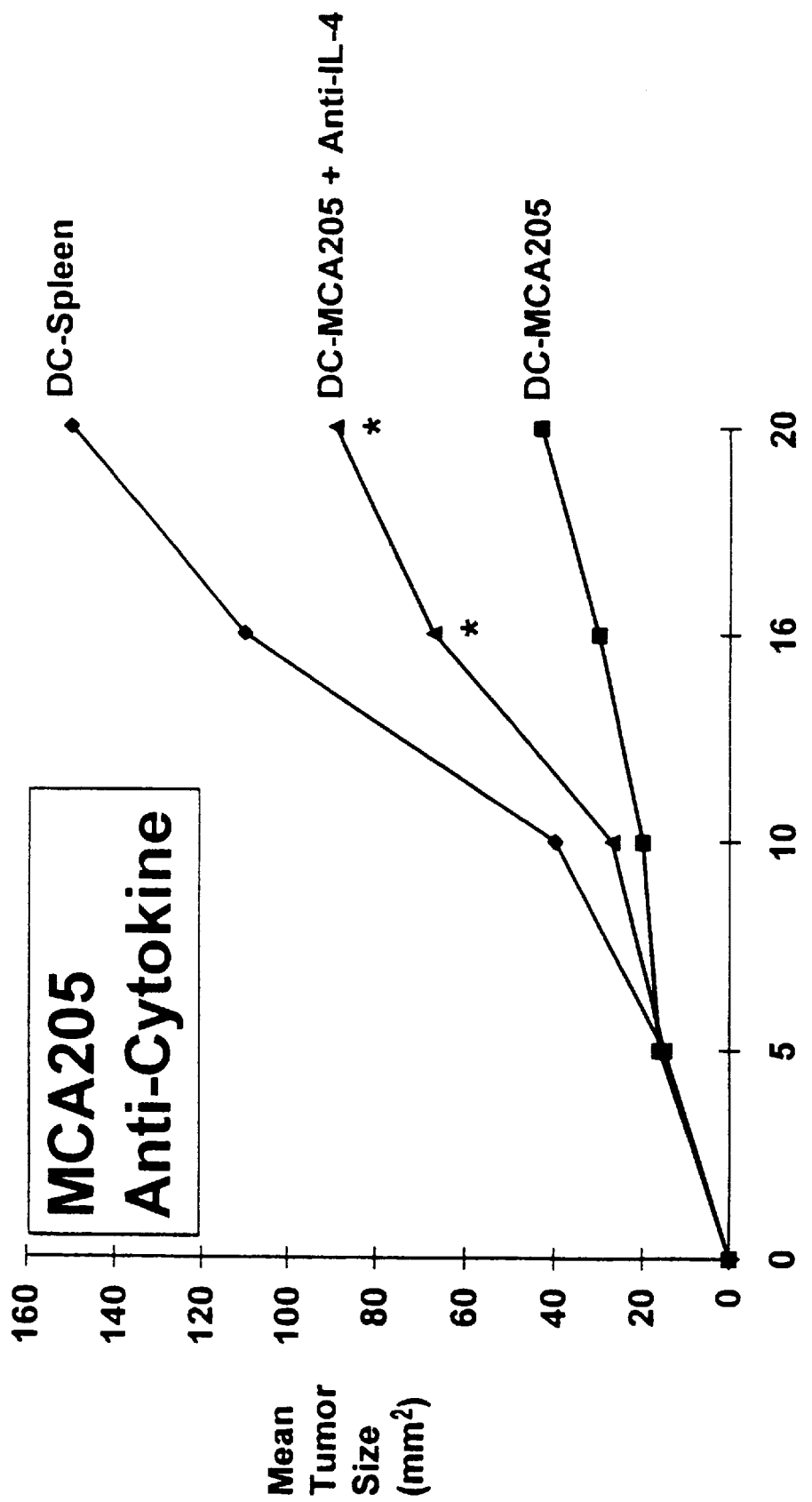
Figure 16D:
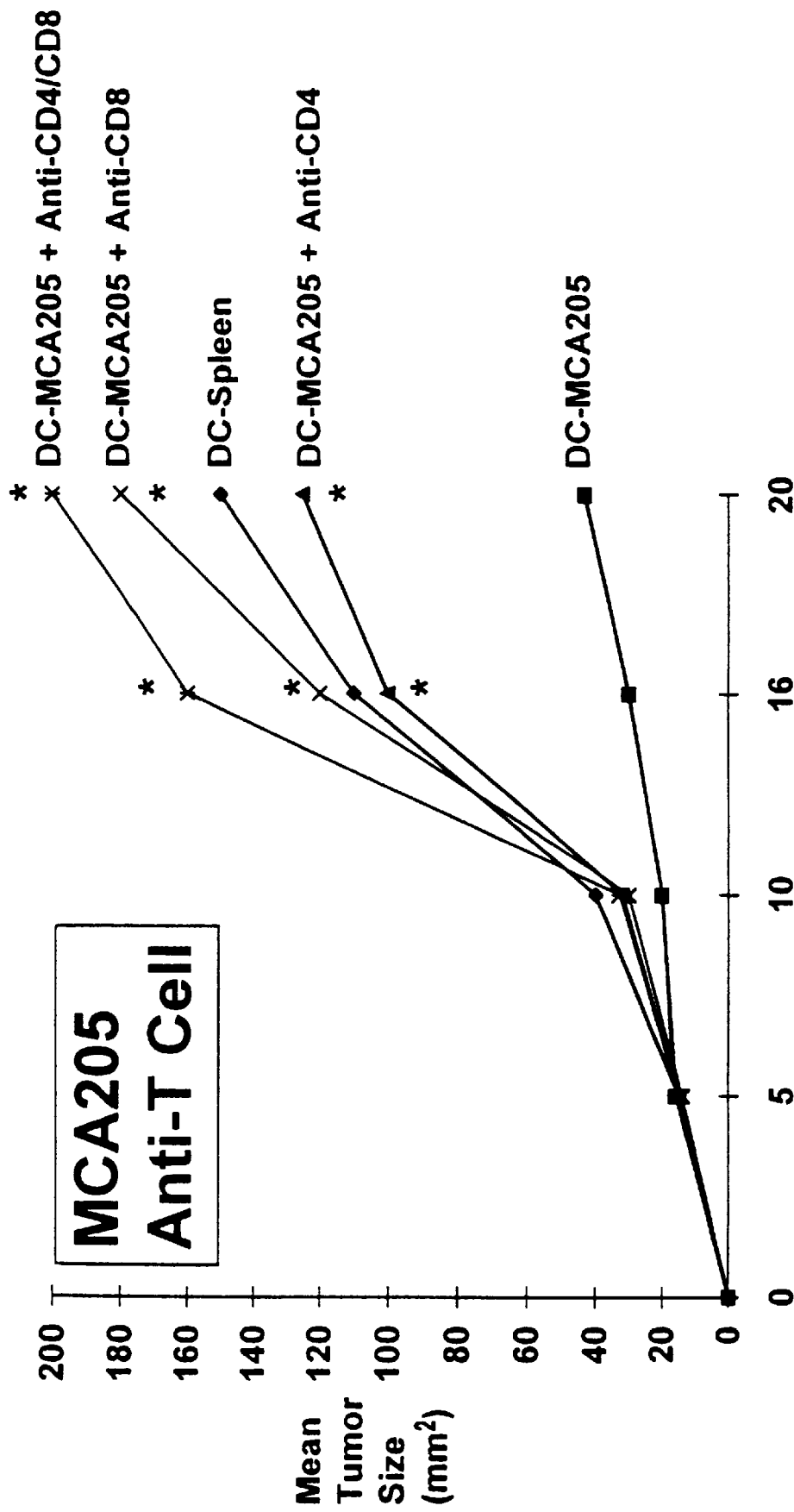

To assess the relevance of the in vitro cytokine data (Tables 7 and 8) in the therapy-induced antitumor immune response in vivo, the animals were treated with neutralizing antibodies reactive with Th1-derived cytokines (FIG. 16B). The coadministration of mAb anti-TNF-α and anti-mIFN-γ, or anti-mIL-12, completely abrogated DC-MCA205-mediated antitumor effects. However, when the first injection of blocking anti-mIL-12 antibodies was injected after the first immunization with DC-MCA205 was performed, the inhibition of therapeutic effects was not significant, stressing the importance of the first vaccination for priming antitumor CTL. Further immunizations may not be critical to amplify the recruitment of additional prime T cells, but perhaps to maintain or expand memory T cells, which are not critically dependent on antigen-specific costimulation. Since high levels of mIL-4 production were measured in the draining lymph nodes and the spleens of the mice treated with and responding to three to four DC-MCA205 or DC-TS/A peptide immunizations, whether this Th2-associated cytokine affected the observed antitumor therapeutic response in vivo was investigated. The 11B11 (anti-mIL-4) mAb was injected before the first DC-MCA205 injection and on a daily basis thereafter for 8 days. Although tumor volumes were greater in 11B11-treated mice, the difference did not appear significant at day 10 after tumor inoculation, compared with the control group receiving DC-MCA205 therapy and injected with normal rat serum (FIG. 16C). However, by day 16, the difference started to appear significant at 95% (Fisher's exact method). This suggests that therapy-induced IL-4 may not play a dominant role in the priming of a specific antitumor immune response by the DC-MCA205, but that it may be implicated in maintaining and/or amplifying the induced antitumor immune responses (Tables 7 and 8). As previously shown by Kennedy, M. K., et al., Eur. J. Immunol 24:2271 (1994), the disclosure of which is incorporated herein by reference, IL-4 can synergize with IL-12 in enhancing the proliferation of antigen-specific Th1 clones. In the present models, IL-4 may cooperate with coinduced Th1-associated cytokines in promoting antitumor immunity.

The following example shows that $CD8^+$ T cells as well as $CD4^+$ T cells are required for the priming and/or the effector phase of the DC-mediated antitumor immune response in vivo.

EXAMPLE 23

It was shown above in the present adoptive transfer experiments (FIG. 14D) that DC-MCA205 induced cell-mediated immune response, protecting naive animals from a subsequent MCA205 challenge. Further, DC elicited potent antitumor CTL responses (FIGS. 15A and 15B) in the in vitro studies. In vivo depletion studies with neutralizing anti-CD4 and/or anti-CD8 antibodies, were next performed early after tumor inoculation, in order to assess the relative contribution of $CD4^+$ and $CD8^+$ T cells in the observed therapeutic effects. Both T cell subsets are implicated in DC-MCA205-induced antitumor immunity since both anti-CD4 or anti-CD8 antibodies, which delete $CD4^+$ T cells or $CD8^+$ T cells in vivo, abrogated the antitumor therapeutic response (FIG. 16D). The inhibition was significantly greater (Fisher's exact method, at 95%) by day 16, when both anti-CD4 and anti-CD8 antibodies were added, compared with that achieved with either one alone, suggesting a cooperativity between both subsets of T cells in the DC-MCA205-mediated antitumor effects.

Immunohistochemistry analysis documented a marked perilesional and intratumoral infiltration of $CD8^+$ T cells (and to a lesser extent of $CD4^+$ T cells) at day 16 in the groups treated with DC-MCA205 (data not shown), but not in those treated with DC pulsed with irrelevant peptides.

In the following example, the acid-eluted peptides of the present invention, which does not result in significant cellular lysis, yielded a superior source of immunogenic epitopes than peptides extracted from tumor cells by 3 repeated cycles of freeze-thaw lysis.

EXAMPLE 24

Figure 17:
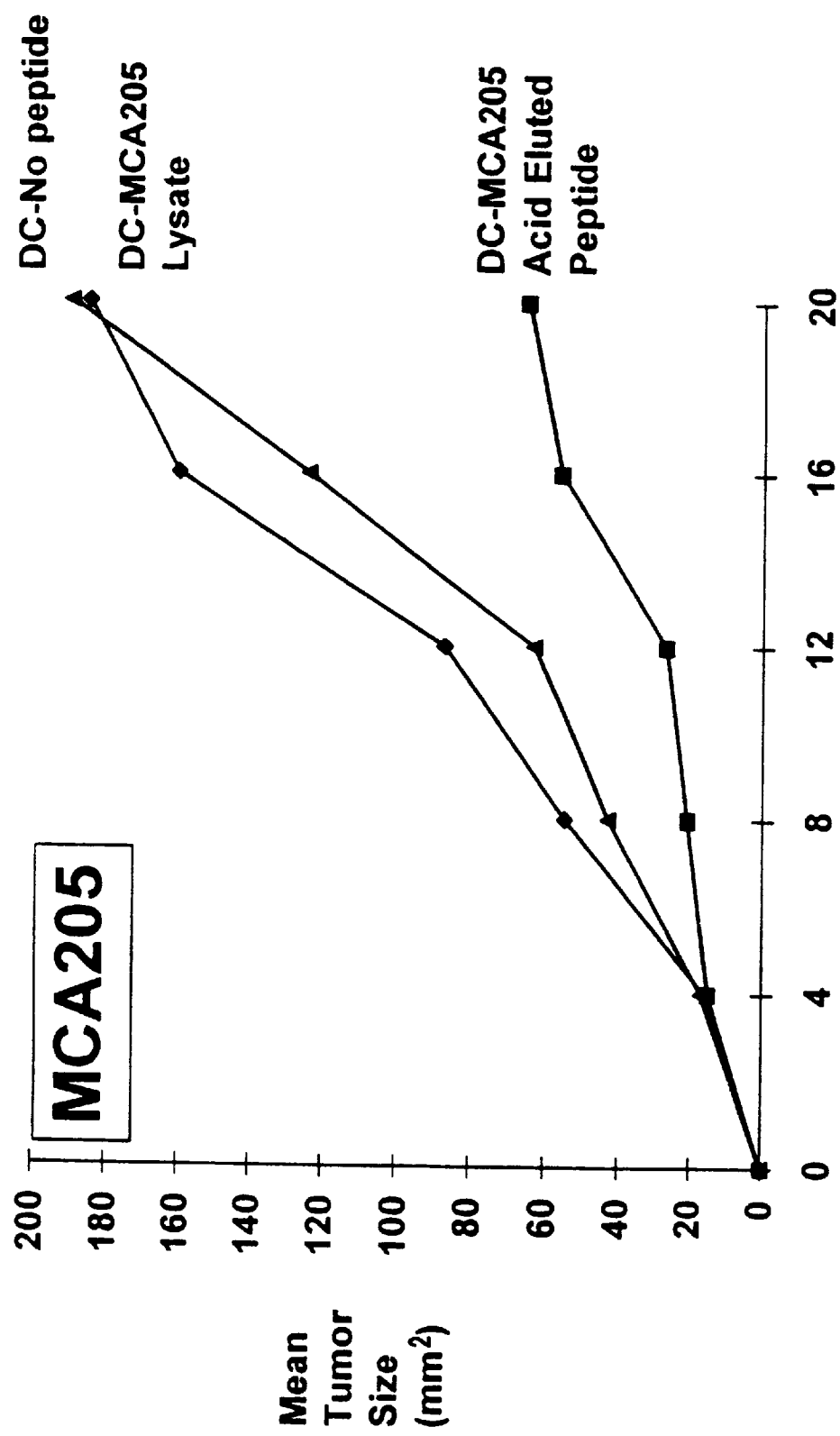
FIG. 17 shows that vaccines comprising DC pulsed with acid-eluted MCA205 peptides ("DC-MCA205 Acid Eluted Peptide") are far superior to vaccines consisting of DC pulsed with lysates of MCA205 (obtained by lysing MCA205 cells by 3 repeated freeze-thaw cycles) ("DC-MCA205 Lysate") in inducing anti-tumor immunity in tumor-bearing mice. Mice with established day 4 s.c. MCA205 tumors were vaccinated with DC-MCA205 acid-eluted peptides or DC-MCA205 lysates on days 0, 5, and 10 and tumor size monitored. "DC-No peptide" is a control. Only animals receiving DC-MCA205 acid-eluted peptide vaccines displayed statistically significant retardation in tumor growth (95% confidence level in Fisher exact test).

As shown in FIG. 17, vaccines consisting of DC pulsed with acid-eluted MCA205 peptides are far superior than vaccines consisting of DC pulsed with lysates of MCA205 in inducing anti-tumor immunity in tumor-bearing mice. Tumor lysates were obtained by 3 sequential freeze (samples placed in a dry ice-methanol bath, −90 degrees celsius)-thaw (samples allowed to thaw at room-temperature, 23 degrees celsius) cycles of 1 billion MCA205 cells in 1 ml of saline buffer. Soluble lysate proteins were obtained by centrifuging the lysate at 14,000×g for 30 minutes and recovery of the supernatant material. DC-MCA205 lysate was generated by culturing 1 million DC with 100 microliters of lysate material overnight at 37 degrees celsius. Mice with established day 4.s.c. MCA205 tumors were inoculated with DC-MCA205 acid-eluted peptide or 0.5 million DC-MCA205 lysate vaccines (0.5 million DC in each vaccine per animal) on days 0, 5, and 10 and tumor size monitored. only animals receiving DC-MCA205 acid-eluted peptide vaccines displayed statistically significant retardation in tumor growth (95% confidence level in Fisher exact test).

The freeze-thaw method presumably results in an unsuitably complex mixture of peptides that may be further complicated by the release of intracellular proteases. Such peptide complexity would also be likely to dilute the effective loading of a sufficient threshold density of relevant T cell epitopes into MHC molecules expressed by DC.

EXAMPLE 25

Generation of DC from Blood

Alternatively, DC can be generated from a patient's blood rather than from their bone marrow and may be advantageous since collection of blood is much less invasive than collection of bone marrow.

Methods

Cell Lines and Media

The Mel 624 melanoma cell line (HLA-A2$^+$, MART-1/Melan-A$^+$, gp100$^+$, tyrosinase+, MAGE-3$^+$) and the EBV-B cell line C1R.A2 were maintained in RPMI-1640 media supplemented with 100 U/ml penicillin, 100 $\mu$g/ml streptomycin, and 10% heat-inactivated fetal bovine serum (all reagents GIBCO-BRL Gaithersberg, Md.). The melanoma cell lines were passaged after a brief treatment (2–4 minutes) with trypsin-EDTA solution (GIBCO-BRL). All cells were cultured in a humidified incubator under 5 $CO_2$ tension and were determined to be free of mycoplasma contamination by GeneProbe kit screening (Fisher, Pittsburgh, Pa.).

Dendritic Cell Generation

Heparinized peripheral blood was obtained by venipuncture from 15 HLA-A2$^+$normal donors and 10 HLA-A2$^+$ donors with AJCC Stage III or IV melanoma treated at the University of Pittsburgh Cancer Institute/University of Pittsburgh School of Medicine. Peripheral blood mononuclear cells ("PBMC") were obtained after density centrifugation on Ficoll-Hypaque gradients per the manufacturer's protocol (LSM, Organon-Teknika, Durham, N.C.). After 4–5 washes in Hank's Buffered Saline (HBSS from GIBCO-BRL, Gaithersburg, Md.), $10^8$ cells/10 ml of serum-free AIM-V medium (GIBCO-BRL) were placed in T75 flasks (COSTAR, Cambridge, Mass.) and incubated for 1–1.5 hours at 37° C., 5% $CO_2$ to allow for cell attachment. Non-adherent cells were frozen in liquid nitrogen in 90% fetal bovine serum/10% DMSO and were retained as T cell enriched responder populations. Plastic adherent cells were cultured for 5–7 days in AIM-V medium supplemented with 1000 U rIL-4/ml+1000 U rGM-CSF/ml at 37° C., 5% $CO_2$ and served as the source of autologous dendritic cells. No medium was added or removed during this culture period. Non-adherent cells were harvested and DCs were purified further by discontinuous density centrifugation on a layer of Nycoprep 1.064 (GIBCO-BRL):LSM (9:1), 800 g×15 minutes. Gradient interface cells were harvested, washed with HBSS, and used in phenotypic and functional assays, as outlined below. Cells generated in this way were determined to be greater than 90% DC based on morphology and the expression of a CD1a+, CD1b+, CD1c+, CD3-, CD14-, CD16-, CD20-, CD40+, CD80+, CD83+, CD86+, MHC class II+phenotype assessed by flow cytometry. Day 7 DC yields were approximately 8–15% of the starting normal donor PBMC numbers, and 7–12% of starting melanoma patient starting PBMC numbers.

Peptides

Peptides were synthesized by standard fmoc chemistries by the University of Pittsburgh Cancer Institutes Peptide Synthesis Facility (Shared Resource) and were purified to >90% using reverse-phase chromatography. The identity of each peptide was validated by mass spectrometry (University of Pittsburgh Biotechnology Center, Mass Spectrometry Facility) for molecular weight and by MS/MS fragmentation providing unambiguous sequencing data. The following sequences were synthesized: MART-1/Melan-A$_{27-35}$ (AAGIGILTV) (SEQ ID NO: 43); MART-1/Melan-A$_{32-40}$ (ILTVILGVL) (also referred to in preceding sections as "p939") (SEQ ID NO: 38); gp100$_{280-288}$ (YLEPGPVTA) (SEQ ID NO: 39); gp100$_{457-466}$ (LLDGTATLRL) (SEQ ID NO: 44); tyrosinase$_{1-9}$ (MLLAVLYCL) (SEQ ID NO: 45); tyrosinase$_{368-376}$ (YMDGTMSQV) (SEQ ID NO: 46); MAGE-3$_{271-279}$ (FLWGPRALV) (SEQ ID NO: 47).

Induction of CTL Using Autologous DC Stimulators Pulsed With Melanoma-Associated Peptide Epitopes Plastic non-adherent DC (1–2×10$^6$) were harvested from IL-4+GM-CSF cultures on days 7, 14, 21, and 28, and washed twice with HBSS. Cells were resuspended in AIM-V media containing no peptide, or 10 $\mu$M of the following HLA-A2-binding melanoma-associated peptides (MART-1/Melan-A$_{27-35}$, MART-1/Melan-A$_{32-40}$, gp100$_{280-288}$, gp100$_{457-466}$, tyrosinase$_{1-9}$, tyrosinase$_{368-376}$, MAGE-3$_{271-279}$, peptide stocks were made at 10 mg/ml in DMSO and stored at −20° C.). Peptide-pulsing (10 $\mu$M final peptide concentration) was allowed to proceed for 2 hours at 37° C., at which time, the cells were washed twice with HBSS, resuspended in 1 ml of AIM-V and irradiated (2500 rad) using a cesium source. Day 7 peptide-pulsed DC were used to "prime" freshly-thawed, autologous PBMC (plastic adherent depleted) responders at a 20:1 responder-to-stimulator ratio. Responding T cells were restimulated weekly (for 4 weeks) using irradiated, peptide-pulsed autologous DC at a 20:1 responder-to-restimulator ratio in AIM-V medium containing 60 IU/ml rhIL-2 (Chiron, Emeryville, Calif.). Each week a portion of the cultured T cells were harvested and evaluated for their ability to mediate cytolysis of the allogeneic HLA-A2+Mel 624 target cell in 4 h $^{51}$Chromium ($^{51}$Cr)-release assays.

Antibodies and Flow Cytometry

Cells were phenotyped using a panel of antibodies obtained commercially or through participation in the 5th International Leukocyte Typing Workshop. Cells were stained using standard procedures (Storkus, W. J., et al., *J. Immunol* 15:3719 (1993), fixed in 4% formalin (SIGMA Chemical Co., St. Louis, Mo.) and analyzed by flow cytometry (FACScan, Becton-Dickinson, Mountainview, Calif.). Intracellular staining for MART-1/Melan-A and gp100 was performed using paraformaldehyde fixation and saponin permeabilization, prior to addition of specific monoclonal antibodies as outlined by Jung, T., et al., *J. Immunol Meth.* 159:197 (1993), the disclosure of which is incorporated herein by reference. The anti-MART-1 mAb was kindly provided by Dr. S. A. Rosenberg (NIH, NCI) as a gift, and is available on request, while the HMB-45 (anti-gp100) mAb was purchased from Enzo Diagnostics Inc. (Farmingdale, N.Y.).

Cytotoxicity Assays

Four hour chromium release assays were performed as described previously. Target cells were labeled with 100 $\mu$Ci (Na$_2$$^{51}$CrO$_4$, Dupont-New England Nuclear, Bedford, Mass.) at 37° C. for 1–2 hours prior to being washed three times with HBSS. 10$^4$ $^{51}$Cr-labeled cells were added to each target well±effector cells for 4 h, 37° C., 5% $CO_2$ in a total volume of 200 $\mu$l. In some wells, the anti-HLA-A2 mAb BB7.2 (20 $\mu$g/well, antibody derived from hybridoma culture supernatants, American Tissue Culture Collection, Rockville, Md.) was added to target cells, prior to the addition of effector cells in order to assess the HLA-A2 restricted nature of T cell-mediated cytotoxicity.

Results

Dendritic Cells May be Effectively Generated From Both Normal Donor and Melanoma Patient Peripheral Blood Mononuclear Cells in Cultures Containing rIL-4+rGM-CSF Initially plastic-adherent "DC" cultures were established in serum-free AIM-V media containing 1000 U/ml rhIL-4+ 1000 rhU/ml GM-CSF from the peripheral blood of more than 50 normal donors and from 12 patients with AJCC stage III or IV metastatic melanoma. As previously noted by other investigators, loosely-adherent DC clusters could be macroscopically observed by days 3–4. The majority of bulk cultured cells (60–80%) were large, with each cell displaying a number of dynamic pseudopods. The smaller lymphocyte contaminants were readily removed by density centrifugation on a Nycoprep/LSM gradient, yielding DC preparations that were typically >90% pure based on morphology. These purified cells were then analyzed for their expression of a panel of markers using flow cytometry. It is to be noted, the cultured DC expressed high levels of MHC class I and class II molecules, high levels of the CD40 and CD86 costimulatory molecules, moderate-to-low levels of the CD80 costimulatory molecule and uniformly high levels of a series of adhesion molecules including CD11a/CD18 (LFA-1), CD44, CD50 (ICAM-2), CD54 (ICAM-1), CD58 (LFA-3), CD102 (ICAM-3). While the majority of day 7 DC expressed CD1a, CD1b, and CD1c, there was clearly always also a CD1-negative subpopulation. These cultured DC expressed only low levels of the putative DC marker CD83. DC populations expressed <3% of the CD3, CD14, CD16, or CD20 markers. As expected, these cells were more potent stimulators of both allospecific proliferative T cell responses in 5 day primary mixed lymphocyte reactions and primary allospecific CTL in 7 day cultures than either freshly isolated B cells or macrophages (data not shown).

Melanoma-Peptide Pulsed Autologous DC Promote the Generation of Anti-Tumor CTL in Vitro from Normal Donor PBMC PBMC responder T cells derived from normal donors (n=12) were repetitively stimulated weekly for 1–4 weeks with irradiated, autologous cultured dendritic cells pre-pulsed with either no peptide or individually pulsed with the previously identified, HLA-A2-presented melanoma peptides listed in Table 9, below.

TABLE 9

| Peptide | Normal PBL Response | Patient PBL Response |
| --- | --- | --- |
| MART-1 27–35 | 11/12 (wk 3–4) | 9/10 (wk 3–4) |
| MART-1 32–40 | 9/12 (wk 3–4) | 9/10 (wk 3–4) |
| gp100 280–288 | 9/12 (wk 3–4) | 8/10 (wk 3–4) |
| gp100 457–466 | 0/12 | 0/10 |
| Tyrosinase 1–9 | 1/12 | 0/10 |
| Tyrosinase 368–376 | 7/12 (wk 3–4) | 6/10 (wk 30–4) |
| MAGE-3 | 0/4 | 1/3 (wk 3) |

Autologous, cultured d7 IL-4+GM-CSF PB-DC were pulsed with the indicated peptides for 2h at room temperature prior to washing and use as stimulators for CTL induction in vitro. T cell cultures were restimulated weekly with identical antigen presenting cells and cytolytic response monitored against the HLA-A2+melanoma 624 in standard 4h chromium release assays. 12 HLA-A2+ normal donors and 10 HLA-A2+ patients with metastatic melanoma were screened. T cell responses are reported as positive if killing of Mel 624 exceeded 20% lysis at an effector/target ratio of 10:1 and if cytolysis was inhibited >80% by the HLA-A2 reactive monoclonal antibody BB7.2. Peak week of CTL reactivity is noted in parentheses.

Figure 18:
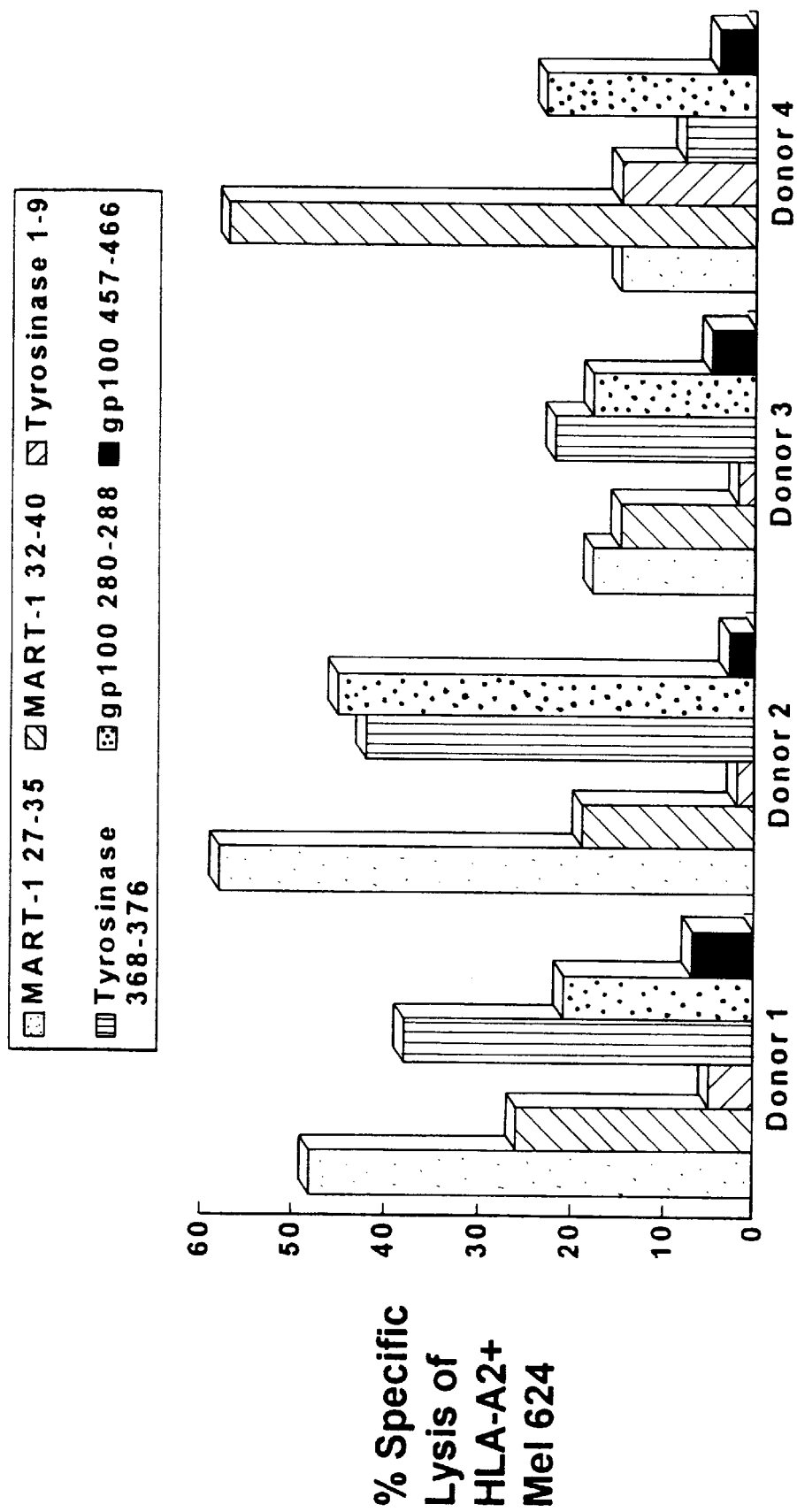
FIG. 18 is a graph showing that anti-melanoma cytolytic effector cells are generated in vitro from normal donor peripheral blood lymphocytes stimulated with autologous DC pulsed with the indicated synthetic melanoma peptides. Results are shown as percent specific lysis of HLA-A2+ Mel 624, which naturally expresses the naturally processed T cell epitopes. For each donor represented bar 1 is MART-1 27–35; bar 2 is MART-1 32–40; bar 3 is Tyrosinase 1–9; bar 4 is Tyrosinase 368–376; bar 5 is gp100 280–288; and bar 6 is gp100 457–466.

Five days after the most recent restimulation, T cell responders were assessed for their ability to lyse the HLA-A2+ melanoma Mel 624 which constitutively expresses each of the MART-1/Melan-A, gp100, tyrosinase, and MAGE-3 antigens. The specificity of T cell reactivity was assessed by addition of the blocking anti-HLA-A2 mAb BB7.2. Data are presented for 4 normal donors in FIG. 18 and Table 9. Reproducible induction of anti-melanoma CTL (greater than 20% lysis at an effector-to-target ratios of 10:1) was obtained within 2–3 stimulations in vitro if the stimulator DC were pre-pulsed with either of the MART-1/Melan-A epitopes, the $gp100_{280-288}$ epitope, or the $tyrosinase_{368-376}$ peptide. In a limited number of normal donor responders, 0/4 responded to the $MAGE-3_{271-279}$ peptide (Table 9). Further, 0/12 of the normal donors responded to the $gp100_{457-466}$ peptide and only 1/12 responded to the $tyrosinase_{1-9}$ peptide (FIG. 18, Table 9). Specific lysis of Mel 624 was inhibited by >80% by addition of BB7.2 mAb (data not shown).

Melanoma-Peptide Pulsed DC Promote Anti-Tumor CTL in Vitro from PBMC Derived From Melanoma Patients In parallel experiments, PBMC derived from 10 patients diagnosed with AJCC stage III or IV melanoma were stimulated with autologous DC pulsed with these same series of peptides. While some patient-to-patient variation was noted for the apparent preference of a given melanoma-associated epitope (FIGS. 19A and 19B), the efficacy of peptide-pulsed DC to promote the expansion of tumor-reactive CTL in vitro did not diverge significantly from that observed in a similar number of normal donors (Table 9). Of note, the $MART-1_{27-35}$ and $gp100_{280-288}$ (position 3 is aspartic acid the naturally-occurring, post-translational modification associated with this epitope) epitopes seemed to represent immunodominant epitopes, based on the rapid kinetics and magnitude of response.

In sum, the foregoing shows that autologous peripheral blood-derived DC pulsed with T cell epitopes can serve as a vaccine for treatment of human cancers, particularly melanoma, in addition to bone marrow-derived DC.

It is clear from the foregoing that T cell epitopes identified by the present invention can be produced synthetically and used to produce peptide vaccines (peptide alone, or any agent incorporating the peptide). However, it is particularly advantageous in the face of treating tumors expressing as yet uncharacterized epitopes to employ unfractionated autologous acid-eluted tumor peptides as demonstrated herein with a suitable adjuvant such as bone marrow- or peripheral blood-derived DC.

The foregoing clearly shows that DC derived from bone marrow or blood, pulsed with acid-eluted peptides derived from autologous tumors can be used as a treatment for established, weakly immunogenic tumors. In this respect the DC serve as an adjuvant for the vaccines of the present invention. Other suitable adjuvants include, but are not limited to, mycobacterial-containing adjuvants, bacillus calmette guerin ("BCG"), and cytokines such as IL-2, IL-12, IL-7 and IL-15, interferons ($\alpha$, $\beta$, $\gamma$), and tumor necrosis factor ($\alpha$).

Alternatively, DNA sequences encoding relevant T cell epitopes identified according to the present invention may be transfected into appropriate antigen presenting cells and administered to patients as a form of gene therapy resulting in the expression of these T cell epitopes in transfected cells which may be administered to patients as a form of gene therapy. It is to be noted that peptides derived by the present invention, and in particular those having low affinities for HLA and which have special loading requirements such as p939 described herein may best be incorporated into patient therapies in the form of ex vivo pulsed autologous antigen presenting cells (i.e., dendritic cells) or moderate-to-high dose intradermal immunization in addition to use as a vaccine. Alternatively, T cell epitopes derived according to the present invention such as p939 may be used to expand antimelanoma CTL in vitro for subsequent adoptive immunotherapy.

Clinical Protocol

The vaccines of the present invention are useful for treatment of patients with advanced malignancies. An IRB- and FDA-approved protocol for the treatment of HLA-A2+ patients with AJCC stage III or IV melanoma has been developed using autologous DC generated from the peripheral blood of patients by culture in AIM-V media supplemented with rhIL-4+ rhGM-CSF for one week. The protocol is for patients with all types of advanced malignancies, but particularly is directed to high risk sarcomas and advanced colorectal cancer.

In order to treat such patients they must have fresh tumor or prior banked tumor. Such patients must also have at least $10^8$ tumor cells in single cell suspension. Patients must not have received any chemotherapy or immunotherapy within the preceding four weeks.

Autologous DC cells will be generated weekly from the peripheral blood of the patients, in AIM-V medium containing 1000 IU rhIL-4 and 1000 IU/ml rhGM-CSF. A yield of approximately 5–20×10$^6$ DC/100ml of the peripheral blood can be anticipated after 5–7 days of culture. DC preparation should be >90% CD80/CD86+, DR+, CD14-, for purposes of use in the vaccine protocol. Autologous DC are prepared at week 0 for week 1 injection and week 1 for week 2 injections and so forth for a course of 4 injections.

A single cell suspension of fresh resected tumor/cryopreserved tumor will be obtained after digestion. Cells will be pelleted and treated with an acid buffer (25.2 G/L Citric acid, 9.37G/L Na$_2$HP04; pH 3.3) and admixed. Treated cells are centrifuged and the supernatant is collected, passed through the activated Sep-Pak columns, and the peptides are eluted from the column with 60% acetonitrile. Eluted peptides are lyophilized to remove the organic solvent and resuspended in 100–200 μl of HBSS for pulsing autologous dendritic cells. The acid elution may be repeated every 24 hours×2 times. The optical density (280 nm) and mass spectrometry of the eluted peptide are measured, after each elution step.

Acid-eluted natural peptides in saline will be added to the DC cultures and cultured for 24 hours at 37° C. DC's are harvested after 24 hours. Excess peptides are removed by washing, and the cells are then prepared for vaccination.

Patients will be administered the peptide pulsed autologous dendritic cells, i.v. over 10 minutes every week for four weeks. Patients will be administered lo of the dose of cultured peptide pulsed DC's on the forearm prior to i.v. injection to monitor for any untoward reaction. If no untoward response occurs, the patient can receive the full dose of autologous dendritic cells i.v.

Recombinant hGM-CSF will be administered at a dose of 125 μg/m sc daily for two weeks along with autologous dendritic cell therapy. Patients will be randomly selected for GM-CSF administration either for the first two week or for the last two weeks of therapy schedule. Patients will be trained to self administer the drug sc at home for the duration of therapy.

Three dose tiers of DC's administered iv will be evaluated; 6 patients each with $10^6$ cells, 3×$10^6$ cells and $10^7$ cells.

All toxicity will be graded using the NCI common toxicity criteria. Previously unknown or severe toxicity will be reported to the NCI as an adverse drug reaction.

Although the invention has been described in detail for the purpose of illustration, it is to be understood that such detail is solely for that purpose and that variations can be made therein by those skilled in the art without departing from the spirit and scope of the invention except as it may be limited by the claims.

We claim:

1. A vaccine for treating a cancer patient who has at least one resectable tumor, comprising:

a composition of an immunologically effective amount of T cell epitopes recovered through acid elution of said T cell epitopes from said patient's resected tumor tissue such that the cells of said tissue remain viable; and a pharmaceutically acceptable adjuvant, wherein said adjuvant is selected from the group consisting of dendritic cells and cytokines or any combination thereof.

2. The vaccine of claim 1, wherein said adjuvant comprises autologous dendritic cells.

3. The vaccine of claim 2, wherein said dendritic cells are cultured with GM-CSF.

4. The vaccine of claim 3, wherein said dendritic cells are further cultured with IL-4.

5. The vaccine of claim 2, wherein said dendritic cells are derived from bone marrow.

6. The vaccine of claim 2, wherein said dendritic cells are derived from peripheral blood.

7. The vaccine of claim 1, wherein said cytokines are selected from the group consisting of interleukins, interferons, and tumor necrosis factors or any combination thereof.

8. The vaccine of claim 7, wherein said cytokines are selected from the group consisting of IL-2, IL-7, IL-12, IL-15, IFN-α, IFN-β, IFN-γ, and TNF-α or any combination thereof.

9. The vaccine of claim 1, wherein said patient is human.

10. A vaccine for treating a cancer patient, comprising:

a composition of an immunologically effective amount of T cell epitopes derived from allogeneic but HLA-matched tumor of the same histologic type present in said patient by acid elution of said T cell epitopes from said tumor tissue such that the cells of said tissue remain viable; and a pharmaceutically acceptable adjuvant, wherein said adjuvant is selected from the group consisting of dendritic cells and cytokines or any combination thereof.

11. The vaccine of claim 10, wherein said adjuvant comprises autologous dendritic cells.

12. The vaccine of claim 11, wherein said dendritic cells are cultured with GM-CSF.

13. The vaccine of claim 12, wherein said dendritic cells are further cultured with IL-4.

14. The vaccine of claim 11, wherein said dendritic cells are derived from bone marrow.

15. The vaccine of claim 11, wherein said dendritic cells are derived from peripheral blood.

16. The vaccine of claim 10, wherein said cytokines are selected from the group consisting of interleukins, interferons, and tumor necrosis factors or any combination thereof.

17. The vaccine of claim 16, wherein said cytokines are selected from the group consisting of IL-2, IL-7, IL-12, IL-15, IFN-α, IFN-β, IFN-γ, and TNF-α or any combination thereof.

18. The vaccine of claim 10, wherein said patient is human.

19. A pharmaceutical composition to elicit an immune response against a cancer patient's tumor in a patient who has at least one resectable tumor, comprising:

a composition of a pharmaceutically effective amount of T cell epitopes recovered through acid elution of said T cells from said patient's resected tumor tissue such that the cells of said tissue remain viable; and a pharmaceutically acceptable adjuvant, wherein said adjuvant is selected from the group consisting of dendritic cells and cytokines or any combination thereof.

20. The pharmaceutical composition of claim 19, wherein said adjuvant comprises autologous dendritic cells.

21. The pharmaceutical composition of claim 19, wherein said cytokines are selected from the group consisting of interleukins, interferons, and tumor necrosis factors or any combination thereof.

22. A pharmaceutical composition to elicit an immune response against a cancer patient's tumor, comprising:

a composition of an immunologically effective amount of T cell epitopes derived from allogeneic but HLA-matched tumor of the same histologic type present in said patient by acid elution of said T cell epitopes from said tumor tissue such that the cells of said tissue remain viable; and a pharmaceutically acceptable adjuvant, wherein said adjuvant is selected from the group consisting of dendritic cells and cytokines or any combination thereof.

23. The pharmaceutical composition of claim 22, wherein said adjuvant comprises autologous dendritic cells.

24. The pharmaceutical composition of claim 22, wherein said cytokines are selected from the group consisting of interleukins, interferons, and tumor necrosis factors or any combination thereof.

* * * * *

SEQUENCE LISTING (1) GENERAL INFORMATION:

(iii) NUMBER OF SEQUENCES:   47

(2) INFORMATION FOR SEQ ID NO:1:

(i) SEQUENCE CHARACTERISTICS:
      (A) LENGTH:        12 amino acids
      (B) TYPE:          amino acid
      (D) TOPOLOGY:      linear (ii) MOLECULE TYPE:     peptide (iii) HYPOTHETICAL:     no (ix) FEATURE:
      (A) NAME/KEY:            Flu M1 57-68
      (D) OTHER INFORMATION:   synthetic peptide (xi) SEQUENCE DESCRIPTION:   SEQ ID NO: 1:

Lys Gly Ile Leu Gly Phe Val Phe Thr Leu Thr Val
1               5                   10

(2) INFORMATION FOR SEQ ID NO:2:

```
        (i) SEQUENCE CHARACTERISTICS:
              (A) LENGTH:         9 amino acids
              (B) TYPE:           amino acid
              (C) TOPOLOGY:       linear (ii) MOLECULE TYPE:        peptide (iii) HYPOTHETICAL:         yes (ix) FEATURE:
              (A) NAME/KEY:       Flu M1 58-66
              (B) OTHER INFORMATION: synthetic peptide (xi) SEQUENCE DESCRIPTION:  SEQ ID NO: 2:

Gly Ile Ile Gly Phe Val Phe Thr Ile
1               5

(2) INFORMATION FOR SEQ ID NO:3:

(i) SEQUENCE CHARACTERISTICS:
              (A) LENGTH:         9 amino acids
              (B) TYPE:           amino acid
              (C) TOPOLOGY:       linear (ii) MOLECULE TYPE:        peptide (iii) HYPOTHETICAL:         yes (ix) FEATURE:
              (A) NAME/KEY:       Flu M1 58-66
              (B) OTHER INFORMATION: synthetic peptide (xi) SEQUENCE DESCRIPTION:  SEQ ID NO: 3:

Gly Ile Ile Gly Phe Val Phe Thr Leu
1               5

(2) INFORMATION FOR SEQ ID NO:4:

(i) SEQUENCE CHARACTERISTICS:
              (A) LENGTH:         9 amino acids
              (B) TYPE:           amino acid
              (C) TOPOLOGY:       linear (ii) MOLECULE TYPE:        peptide (iii) HYPOTHETICAL:         yes (ix) FEATURE:
              (A) NAME/KEY:       Flu M1 58-66
              (B) OTHER INFORMATION: synthetic peptide (xi) SEQUENCE DESCRIPTION:  SEQ ID NO: 4:

Gly Ile Leu Gly Phe Val Phe Thr Leu
1               5

(2) INFORMATION FOR SEQ ID NO:5:

(i) SEQUENCE CHARACTERISTICS:
              (A) LENGTH:         9 amino acids
              (B) TYPE:           amino acid
              (C) TOPOLOGY:       linear (ii) MOLECULE TYPE:        peptide (iii) HYPOTHETICAL:         yes (ix) FEATURE:
              (A) NAME/KEY:       Flu M1 58-66
              (B) OTHER INFORMATION: synthetic peptide (xi) SEQUENCE DESCRIPTION:  SEQ ID NO: 5:
```

```
Gly Leu Leu Gly Phe Val Phe Thr Leu
1               5

(2) INFORMATION FOR SEQ ID NO:6:

(i) SEQUENCE CHARACTERISTICS:
        (A) LENGTH:        9 amino acids
        (B) TYPE:          amino acid
        (D) TOPOLOGY:      linear (ii) MOLECULE TYPE:    peptide (iii) HYPOTHETICAL:    yes (ix) FEATURE:
        (A) NAME/KEY:          p939
        (D) OTHER INFORMATION: synthetic peptide (xi) SEQUENCE DESCRIPTION:  SEQ ID NO: 6:

Ile Ile Thr Val Ile Ile Gly Val Ile
1               5

(2) INFORMATION FOR SEQ ID NO:7:

(i) SEQUENCE CHARACTERISTICS:
        (A) LENGTH:        9 amino acids
        (B) TYPE:          amino acid
        (C) TOPOLOGY:      linear (ii) MOLECULE TYPE:    peptide (iii) HYPOTHETICAL:    yes (ix) FEATURE:
        (A) NAME/KEY:          p939
        (B) OTHER INFORMATION: synthetic peptide (xi) SEQUENCE DESCRIPTION:  SEQ ID NO: 7:

Ile Leu Thr Val Ile Ile Gly Val Ile
1               5

(2) INFORMATION FOR SEQ ID NO:8:

(i) SEQUENCE CHARACTERISTICS:
        (A) LENGTH:        9 amino acids
        (B) TYPE:          amino acid
        (C) TOPOLOGY:      linear (ii) MOLECULE TYPE:    peptide (iii) HYPOTHETICAL:    yes (ix) FEATURE:
        (A) NAME/KEY:          p939
        (B) OTHER INFORMATION: synthetic peptide (xi) SEQUENCE DESCRIPTION:  SEQ ID NO: 8:

Ile Ile Thr Val Leu Ile Gly Val Ile
1               5

(2) INFORMATION FOR SEQ ID NO:9:

(i) SEQUENCE CHARACTERISTICS:
        (A) LENGTH:        9 amino acids
        (B) TYPE:          amino acid
        (C) TOPOLOGY:      linear (ii) MOLECULE TYPE:    peptide (iii) HYPOTHETICAL:    yes (ix) FEATURE:
```

(A) NAME/KEY:          p939
            (B) OTHER INFORMATION: synthetic peptide (xi) SEQUENCE DESCRIPTION:    SEQ ID NO: 9:

Ile Ile Thr Val Ile Leu Gly Val Ile
1               5

(2) INFORMATION FOR SEQ ID NO:10:

(i) SEQUENCE CHARACTERISTICS:
            (A) LENGTH:     9 amino acids
            (B) TYPE:       amino acid
            (C) TOPOLOGY:   linear (ii) MOLECULE TYPE:     peptide (iii) HYPOTHETICAL:      yes (ix) FEATURE:
            (A) NAME/KEY:          p939
            (B) OTHER INFORMATION: synthetic peptide (xi) SEQUENCE DESCRIPTION:    SEQ ID NO: 10:

Ile Ile Thr Val Ile Ile Gly Val Leu
1               5

(2) INFORMATION FOR SEQ ID NO:11:

(i) SEQUENCE CHARACTERISTICS:
            (A) LENGTH:     9 amino acids
            (B) TYPE:       amino acid
            (D) TOPOLOGY:   linear (ii) MOLECULE TYPE:     peptide (iii) HYPOTHETICAL:      yes (ix) FEATURE:
            (A) NAME/KEY:          p939
            (D) OTHER INFORMATION: synthetic peptide (xi) SEQUENCE DESCRIPTION:    SEQ ID NO: 11:

Leu Ile Thr Val Ile Ile Gly Val Ile
1               5

(2) INFORMATION FOR SEQ ID NO:12:

(i) SEQUENCE CHARACTERISTICS:
            (A) LENGTH:     9 amino acids
            (B) TYPE:       amino acid
            (C) TOPOLOGY:   linear (ii) MOLECULE TYPE:     peptide (iii) HYPOTHETICAL:      yes (ix) FEATURE:
            (A) NAME/KEY:          p939
            (B) OTHER INFORMATION: synthetic peptide (xi) SEQUENCE DESCRIPTION:    SEQ ID NO: 12:

Leu Leu Thr Val Ile Ile Gly Val Ile
1               5

(2) INFORMATION FOR SEQ ID NO:13:

(i) SEQUENCE CHARACTERISTICS:
            (A) LENGTH:     9 amino acids
            (B) TYPE:       amino acid
            (C) TOPOLOGY:   linear (ii) MOLECULE TYPE:      peptide (iii) HYPOTHETICAL:       yes (ix) FEATURE:
            (A) NAME/KEY:       p939
            (B) OTHER INFORMATION: synthetic peptide (xi) SEQUENCE DESCRIPTION: SEQ ID NO: 13:

Leu Ile Thr Val Leu Ile Gly Val Ile
 1               5

(2) INFORMATION FOR SEQ ID NO:14:

(i) SEQUENCE CHARACTERISTICS:
            (A) LENGTH:         9 amino acids
            (B) TYPE:           amino acid
            (C) TOPOLOGY:       linear (ii) MOLECULE TYPE:      peptide (iii) HYPOTHETICAL:       yes (ix) FEATURE:
            (A) NAME/KEY:       p939
            (B) OTHER INFORMATION: synthetic peptide (xi) SEQUENCE DESCRIPTION: SEQ ID NO: 14:

Leu Ile Thr Val Ile Leu Gly Val Ile
 1               5

(2) INFORMATION FOR SEQ ID NO:15:

(i) SEQUENCE CHARACTERISTICS:
            (A) LENGTH:         9 amino acids
            (B) TYPE:           amino acid
            (C) TOPOLOGY:       linear (ii) MOLECULE TYPE:      peptide (iii) HYPOTHETICAL:       yes (ix) FEATURE:
            (A) NAME/KEY:       p939
            (B) OTHER INFORMATION: synthetic peptide (xi) SEQUENCE DESCRIPTION: SEQ ID NO: 15:

Leu Ile Thr Val Ile Ile Gly Val Leu
 1               5

(2) INFORMATION FOR SEQ ID NO:16:

(i) SEQUENCE CHARACTERISTICS:
            (A) LENGTH:         9 amino acids
            (B) TYPE:           amino acid
            (D) TOPOLOGY:       linear (ii) MOLECULE TYPE:      peptide (iii) HYPOTHETICAL:       yes (ix) FEATURE:
            (A) NAME/KEY:       p939
            (D) OTHER INFORMATION: synthetic peptide (xi) SEQUENCE DESCRIPTION: SEQ ID NO: 16:

Ile Leu Thr Val Leu Ile Gly Val Ile
 1               5

(2) INFORMATION FOR SEQ ID NO:17:

```
    (i) SEQUENCE CHARACTERISTICS:
        (A) LENGTH:         9 amino acids
        (B) TYPE:           amino acid
        (C) TOPOLOGY:       linear (ii) MOLECULE TYPE:      peptide (iii) HYPOTHETICAL:       yes (ix) FEATURE:
        (A) NAME/KEY:           p939
        (B) OTHER INFORMATION:  synthetic peptide (xi) SEQUENCE DESCRIPTION:   SEQ ID NO: 17:

Ile Leu Thr Val Ile Leu Gly Val Ile
1               5

(2) INFORMATION FOR SEQ ID NO:18:

(i) SEQUENCE CHARACTERISTICS:
        (A) LENGTH:         9 amino acids
        (B) TYPE:           amino acid
        (C) TOPOLOGY:       linear (ii) MOLECULE TYPE:      peptide (iii) HYPOTHETICAL:       yes (ix) FEATURE:
        (A) NAME/KEY:           p939
        (B) OTHER INFORMATION:  synthetic peptide (xi) SEQUENCE DESCRIPTION:   SEQ ID NO: 18:

Ile Leu Thr Val Ile Ile Gly Val Leu
1               5

(2) INFORMATION FOR SEQ ID NO:19:

(i) SEQUENCE CHARACTERISTICS:
        (A) LENGTH:         9 amino acids
        (B) TYPE:           amino acid
        (C) TOPOLOGY:       linear (ii) MOLECULE TYPE:      peptide (iii) HYPOTHETICAL:       yes (ix) FEATURE:
        (A) NAME/KEY:           p939
        (B) OTHER INFORMATION:  synthetic peptide (xi) SEQUENCE DESCRIPTION:   SEQ ID NO: 19:

Ile Ile Thr Val Leu Leu Gly Val Ile
1               5

(2) INFORMATION FOR SEQ ID NO:20:

(i) SEQUENCE CHARACTERISTICS:
        (A) LENGTH:         9 amino acids
        (B) TYPE:           amino acid
        (C) TOPOLOGY:       linear (ii) MOLECULE TYPE:      peptide (iii) HYPOTHETICAL:       yes (ix) FEATURE:
        (A) NAME/KEY:           p939
        (B) OTHER INFORMATION:  synthetic peptide (xi) SEQUENCE DESCRIPTION:   SEQ ID NO: 20:

Ile Ile Thr Val Leu Ile Gly Val Leu
```

```
1               5

(2) INFORMATION FOR SEQ ID NO:21:

(i) SEQUENCE CHARACTERISTICS:
        (A) LENGTH:         9 amino acids
        (B) TYPE:           amino acid
        (D) TOPOLOGY:       linear (ii) MOLECULE TYPE:     peptide (iii) HYPOTHETICAL:     yes (ix) FEATURE:
        (A) NAME/KEY:            p939
        (D) OTHER INFORMATION:   synthetic peptide (xi) SEQUENCE DESCRIPTION:   SEQ ID NO: 21:

Ile Ile Thr Val Ile Leu Gly Val Leu
1               5

(2) INFORMATION FOR SEQ ID NO:22:

(i) SEQUENCE CHARACTERISTICS:
        (A) LENGTH:         9 amino acids
        (B) TYPE:           amino acid
        (C) TOPOLOGY:       linear (ii) MOLECULE TYPE:     peptide (iii) HYPOTHETICAL:     yes (ix) FEATURE:
        (A) NAME/KEY:            p939
        (B) OTHER INFORMATION:   synthetic peptide (xi) SEQUENCE DESCRIPTION:   SEQ ID NO: 22:

Leu Leu Thr Val Leu Ile Gly Val Ile
1               5

(2) INFORMATION FOR SEQ ID NO:23:

(i) SEQUENCE CHARACTERISTICS:
        (A) LENGTH:         9 amino acids
        (B) TYPE:           amino acid
        (C) TOPOLOGY:       linear (ii) MOLECULE TYPE:     peptide (iii) HYPOTHETICAL:     yes (ix) FEATURE:
        (A) NAME/KEY:            p939
        (B) OTHER INFORMATION:   synthetic peptide (xi) SEQUENCE DESCRIPTION:   SEQ ID NO: 23:

Leu Leu Thr Val Ile Leu Gly Val Ile
1               5

(2) INFORMATION FOR SEQ ID NO:24:

(i) SEQUENCE CHARACTERISTICS:
        (A) LENGTH:         9 amino acids
        (B) TYPE:           amino acid
        (C) TOPOLOGY:       linear (ii) MOLECULE TYPE:     peptide (iii) HYPOTHETICAL:     yes (ix) FEATURE:
        (A) NAME/KEY:            p939
```

(B) OTHER INFORMATION: synthetic peptide (xi) SEQUENCE DESCRIPTION: SEQ ID NO: 24:

Leu Leu Thr Val Ile Ile Gly Val Leu
1               5

(2) INFORMATION FOR SEQ ID NO:25:

(i) SEQUENCE CHARACTERISTICS:
        (A) LENGTH:        9 amino acids
        (B) TYPE:          amino acid
        (C) TOPOLOGY:      linear (ii) MOLECULE TYPE:    peptide (iii) HYPOTHETICAL:    yes (ix) FEATURE:
        (A) NAME/KEY:      p939
        (B) OTHER INFORMATION: synthetic peptide (xi) SEQUENCE DESCRIPTION: SEQ ID NO: 25:

Ile Leu Thr Val Leu Leu Gly Val Ile
1               5

(2) INFORMATION FOR SEQ ID NO:26:

(i) SEQUENCE CHARACTERISTICS:
        (A) LENGTH:        9 amino acids
        (B) TYPE:          amino acid
        (D) TOPOLOGY:      linear (ii) MOLECULE TYPE:    peptide (iii) HYPOTHETICAL:    yes (ix) FEATURE:
        (A) NAME/KEY:      p939
        (D) OTHER INFORMATION: synthetic peptide (xi) SEQUENCE DESCRIPTION: SEQ ID NO: 26:

Ile Leu Thr Val Leu Ile Gly Val Leu
1               5

(2) INFORMATION FOR SEQ ID NO:27:

(i) SEQUENCE CHARACTERISTICS:
        (A) LENGTH:        9 amino acids
        (B) TYPE:          amino acid
        (C) TOPOLOGY:      linear (ii) MOLECULE TYPE:    peptide (iii) HYPOTHETICAL:    yes (ix) FEATURE:
        (A) NAME/KEY:      p939
        (B) OTHER INFORMATION: synthetic peptide (xi) SEQUENCE DESCRIPTION: SEQ ID NO: 27:

Ile Ile Thr Val Leu Leu Gly Val Leu
1               5

(2) INFORMATION FOR SEQ ID NO:28:

(i) SEQUENCE CHARACTERISTICS:
        (A) LENGTH:        9 amino acids
        (B) TYPE:          amino acid
        (C) TOPOLOGY:      linear (ii) MOLECULE TYPE:    peptide

```
        (iii) HYPOTHETICAL:        yes (ix) FEATURE:
              (A) NAME/KEY:        p939
              (B) OTHER INFORMATION:  synthetic peptide (xi) SEQUENCE DESCRIPTION:   SEQ ID NO: 28:

Leu Ile Thr Val Leu Leu Gly Val Ile
1               5

(2) INFORMATION FOR SEQ ID NO:29:

(i) SEQUENCE CHARACTERISTICS:
              (A) LENGTH:          9 amino acids
              (B) TYPE:            amino acid
              (C) TOPOLOGY:        linear (ii) MOLECULE TYPE:       peptide (iii) HYPOTHETICAL:        yes (ix) FEATURE:
              (A) NAME/KEY:        p939
              (B) OTHER INFORMATION:  synthetic peptide (xi) SEQUENCE DESCRIPTION:   SEQ ID NO: 29:

Leu Ile Thr Val Ile Leu Gly Val Leu
1               5

(2) INFORMATION FOR SEQ ID NO:30:

(i) SEQUENCE CHARACTERISTICS:
              (A) LENGTH:          9 amino acids
              (B) TYPE:            amino acid
              (C) TOPOLOGY:        linear (ii) MOLECULE TYPE:       peptide (iii) HYPOTHETICAL:        yes (ix) FEATURE:
              (A) NAME/KEY:        p939
              (B) OTHER INFORMATION:  synthetic peptide (xi) SEQUENCE DESCRIPTION:   SEQ ID NO: 30:

Leu Ile Thr Val Leu Ile Gly Val Leu
1               5

(2) INFORMATION FOR SEQ ID NO:31:

(i) SEQUENCE CHARACTERISTICS:
              (A) LENGTH:          9 amino acids
              (B) TYPE:            amino acid
              (D) TOPOLOGY:        linear (ii) MOLECULE TYPE:       peptide (iii) HYPOTHETICAL:        yes (ix) FEATURE:
              (A) NAME/KEY:        p939
              (D) OTHER INFORMATION:  synthetic peptide (xi) SEQUENCE DESCRIPTION:   SEQ ID NO: 31:

Ile Leu Thr Val Ile Leu Gly Val Leu
1               5

(2) INFORMATION FOR SEQ ID NO:32:

(i) SEQUENCE CHARACTERISTICS:
```

(A) LENGTH:           9 amino acids
                    (B) TYPE:             amino acid
                    (C) TOPOLOGY:         linear (ii) MOLECULE TYPE:    peptide (iii) HYPOTHETICAL:     yes (ix) FEATURE:
                    (A) NAME/KEY:         p939
                    (B) OTHER INFORMATION: synthetic peptide (xi) SEQUENCE DESCRIPTION:    SEQ ID NO: 32:

Leu Leu Thr Val Leu Leu Gly Val Ile
1               5

(2) INFORMATION FOR SEQ ID NO:33:

(i) SEQUENCE CHARACTERISTICS:
                    (A) LENGTH:           9 amino acids
                    (B) TYPE:             amino acid
                    (C) TOPOLOGY:         linear (ii) MOLECULE TYPE:    peptide (iii) HYPOTHETICAL:     yes (ix) FEATURE:
                    (A) NAME/KEY:         p939
                    (B) OTHER INFORMATION: synthetic peptide (xi) SEQUENCE DESCRIPTION:    SEQ ID NO: 33:

Leu Leu Thr Val Ile Leu Gly Val Leu
1               5

(2) INFORMATION FOR SEQ ID NO:34:

(i) SEQUENCE CHARACTERISTICS:
                    (A) LENGTH:           9 amino acids
                    (B) TYPE:             amino acid
                    (C) TOPOLOGY:         linear (ii) MOLECULE TYPE:    peptide (iii) HYPOTHETICAL:     yes (ix) FEATURE:
                    (A) NAME/KEY:         p939
                    (B) OTHER INFORMATION: synthetic peptide (xi) SEQUENCE DESCRIPTION:    SEQ ID NO: 34:

Ile Leu Thr Val Leu Leu Gly Val Leu
1               5

(2) INFORMATION FOR SEQ ID NO:35:

(i) SEQUENCE CHARACTERISTICS:
                    (A) LENGTH:           9 amino acids
                    (B) TYPE:             amino acid
                    (C) TOPOLOGY:         linear (ii) MOLECULE TYPE:    peptide (iii) HYPOTHETICAL:     yes (ix) FEATURE:
                    (A) NAME/KEY:         p939
                    (B) OTHER INFORMATION: synthetic peptide (xi) SEQUENCE DESCRIPTION:    SEQ ID NO: 35:

Leu Ile Thr Val Leu Leu Gly Val Leu
1               5

(2) INFORMATION FOR SEQ ID NO:36:

(i) SEQUENCE CHARACTERISTICS:
        (A) LENGTH:      9 amino acids
        (B) TYPE:        amino acid
        (D) TOPOLOGY:    linear (ii) MOLECULE TYPE:    peptide (iii) HYPOTHETICAL:    yes (ix) FEATURE:
        (A) NAME/KEY:     p939
        (D) OTHER INFORMATION: synthetic peptide (xi) SEQUENCE DESCRIPTION: SEQ ID NO: 36:

Leu Leu Thr Val Leu Ile Gly Val Leu
1          5

(2) INFORMATION FOR SEQ ID NO:37:

(i) SEQUENCE CHARACTERISTICS:
        (A) LENGTH:      9 amino acids
        (B) TYPE:        amino acid
        (C) TOPOLOGY:    linear (ii) MOLECULE TYPE:    peptide (iii) HYPOTHETICAL:    yes (ix) FEATURE:
        (A) NAME/KEY:     p939
        (B) OTHER INFORMATION: synthetic peptide (xi) SEQUENCE DESCRIPTION: SEQ ID NO: 37:

Leu Leu Thr Val Leu Leu Gly Val Leu
1          5

(2) INFORMATION FOR SEQ ID NO:38:

(i) SEQUENCE CHARACTERISTICS:
        (A) LENGTH:      9 amino acids
        (B) TYPE:        amino acid
        (C) TOPOLOGY:    linear (ii) MOLECULE TYPE:    peptide (iii) HYPOTHETICAL:    no (ix) FEATURE:
        (A) NAME/KEY:         p939/MART-1 32-40
        (B) OTHER INFORMATION: synthetic peptide (xi) SEQUENCE DESCRIPTION: SEQ ID NO: 38:

Ile Leu Thr Val Ile Leu Gly Val Leu
1          5

(2) INFORMATION FOR SEQ ID NO:39:

(i) SEQUENCE CHARACTERISTICS:
        (A) LENGTH:      9 amino acids
        (B) TYPE:        amino acid
        (C) TOPOLOGY:    linear (ii) MOLECULE TYPE:    peptide (iii) HYPOTHETICAL:    no (ix) FEATURE:
        (A) NAME/KEY:         gp100 280-288
        (B) OTHER INFORMATION: synthetic peptide (xi) SEQUENCE DESCRIPTION:     SEQ ID NO: 39:

Tyr Leu Glu Pro Gly Pro Val Thr Ala
1               5

(2) INFORMATION FOR SEQ ID NO:40:

(i) SEQUENCE CHARACTERISTICS:
           (A) LENGTH:        10 amino acids
           (B) TYPE:          amino acid
           (C) TOPOLOGY:      linear (ii) MOLECULE TYPE:     peptide (iii) HYPOTHETICAL:      no (ix) FEATURE:
           (A) NAME/KEY:          HIV-nef 73-82
           (B) OTHER INFORMATION: synthetic peptide (xi) SEQUENCE DESCRIPTION:     SEQ ID NO: 40:

Gln Val Pro Leu Arg Pro Met Thr Tyr Lys
1               5                   10

(2) INFORMATION FOR SEQ ID NO:41:

(i) SEQUENCE CHARACTERISTICS:
           (A) LENGTH:        11 amino acids
           (B) TYPE:          amino acid
           (D) TOPOLOGY:      linear (ii) MOLECULE TYPE:     peptide (iii) HYPOTHETICAL:      no (ix) FEATURE:
           (A) NAME/KEY:          p53 186-196
           (D) OTHER INFORMATION: synthetic peptide (xi) SEQUENCE DESCRIPTION:     SEQ ID NO: 41:

Asp Gly Leu Ala Pro Pro Gln His Leu Ile Arg
1               5                   10

(2) INFORMATION FOR SEQ ID NO:42:

(i) SEQUENCE CHARACTERISTICS:
           (A) LENGTH:        9 amino acids
           (B) TYPE:          amino acid
           (C) TOPOLOGY:      linear (ii) MOLECULE TYPE:     peptide (iii) HYPOTHETICAL:      no (ix) FEATURE:
           (A) NAME/KEY:          p53 264-272
           (B) OTHER INFORMATION: synthetic peptide (xi) SEQUENCE DESCRIPTION:     SEQ ID NO: 42:

Leu Leu Gly Arg Asn Ser Phe Glu Val
1               5

(2) INFORMATION FOR SEQ ID NO:43:

(i) SEQUENCE CHARACTERISTICS:
           (A) LENGTH:        9 amino acids
           (B) TYPE:          amino acid
           (D) TOPOLOGY:      linear (ii) MOLECULE TYPE:     peptide

```
          (iii) HYPOTHETICAL:      no (ix) FEATURE:
                (A) NAME/KEY:      MART-1/Melan-A27-35
                (D) OTHER INFORMATION:  synthetic peptide (xi) SEQUENCE DESCRIPTION: SEQ ID NO: 43:

Ala Ala Gly Ile Gly Ile Leu Thr Val
1               5

(2) INFORMATION FOR SEQ ID NO:44:

(i) SEQUENCE CHARACTERISTICS:
                (A) LENGTH:        10 amino acids
                (B) TYPE:          amino acid
                (D) TOPOLOGY:      linear (ii) MOLECULE TYPE:     peptide (iii) HYPOTHETICAL:      no (ix) FEATURE:
                (A) NAME/KEY:      gp100457-466
                (D) OTHER INFORMATION:  synthetic peptide (xi) SEQUENCE DESCRIPTION: SEQ ID NO: 44:

Leu Leu Asp Gly Thr Ala Thr Leu Arg Leu
1               5                  10

(2) INFORMATION FOR SEQ ID NO:45:

(i) SEQUENCE CHARACTERISTICS:
                (A) LENGTH:        9 amino acids
                (B) TYPE:          amino acid
                (D) TOPOLOGY:      linear (ii) MOLECULE TYPE:     peptide (iii) HYPOTHETICAL:      no (ix) FEATURE:
                (A) NAME/KEY:      tyrosinase1-9
                (D) OTHER INFORMATION:  synthetic peptide (xi) SEQUENCE DESCRIPTION: SEQ ID NO: 45:

Met Leu Leu Ala Val Leu Tyr Cys Leu
1               5

(2) INFORMATION FOR SEQ ID NO:46:

(i) SEQUENCE CHARACTERISTICS:
                (A) LENGTH:        9 amino acids
                (B) TYPE:          amino acid
                (D) TOPOLOGY:      linear (ii) MOLECULE TYPE:     peptide (iii) HYPOTHETICAL:      no (ix) FEATURE:
                (A) NAME/KEY:      tyrosinase368-376
                (D) OTHER INFORMATION:  synthetic peptide (xi) SEQUENCE DESCRIPTION: SEQ ID NO: 46:

Tyr Met Asp Gly Thr Met Ser Gln Val
1               5

(2) INFORMATION FOR SEQ ID NO:47:

(i) SEQUENCE CHARACTERISTICS:
                (A) LENGTH:        9 amino acids
```

```
            (B) TYPE:             amino acid
            (D) TOPOLOGY:         linear (ii) MOLECULE TYPE:          peptide (iii) HYPOTHETICAL:           no (ix) FEATURE:
            (A) NAME/KEY:         MAGE-3271-279
            (D) OTHER INFORMATION: synthetic peptide (xi) SEQUENCE DESCRIPTION:   SEQ ID NO: 47:

Phe Leu Trp Gly Pro Arg Ala Leu Val
1               5
```